US012606603B2

(12) United States Patent
Tampella et al.

(10) Patent No.: US 12,606,603 B2
(45) Date of Patent: Apr. 21, 2026

(54) IL-13 RECEPTOR ALPHA 2 TARGETED, ZETAKINE DIRECTED T CELL IMMUNOTHERAPY

(71) Applicant: Seattle Children's Hospital, Seattle, WA (US)

(72) Inventors: Giacomo Tampella, Seattle, WA (US); Michael C. Jensen, Seattle, WA (US); Adam Johnson, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 1020 days.

(21) Appl. No.: 16/979,475

(22) PCT Filed: Mar. 12, 2019

(86) PCT No.: PCT/US2019/021833
§ 371 (c)(1),
(2) Date: Sep. 9, 2020

(87) PCT Pub. No.: WO2019/178085
PCT Pub. Date: Sep. 19, 2019

(65) Prior Publication Data
US 2021/0017246 A1     Jan. 21, 2021

Related U.S. Application Data

(60) Provisional application No. 62/643,139, filed on Mar. 14, 2018.

(51) Int. Cl.
| | |
|---|---|
| *C12N 15/62* | (2006.01) |
| *C07K 14/54* | (2006.01) |
| *C07K 14/725* | (2006.01) |

(52) U.S. Cl.
CPC ...... *C07K 14/5437* (2013.01); *C07K 14/7051* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 8,822,647 | B2 | 9/2014 | Jensen |
| 2009/0098142 | A1 | 4/2009 | Kasaian et al. |
| 2012/0148552 | A1 | 6/2012 | Jensen |
| 2014/0271635 | A1 | 9/2014 | Brogdon et al. |
| 2015/0030614 | A1 | 1/2015 | Bebbington et al. |
| 2015/0038684 | A1 | 2/2015 | Jensen |
| 2015/0266962 | A1 | 9/2015 | Ma et al. |
| 2015/0299756 | A1 | 10/2015 | Hishiya et al. |
| 2015/0306141 | A1 | 10/2015 | Jensen |
| 2016/0152723 | A1 | 6/2016 | Chen |
| 2016/0175398 | A1 | 6/2016 | Jensen |
| 2016/0340649 | A1 | 11/2016 | Brown et al. |
| 2017/0209543 | A9 | 7/2017 | Jensen |

| | | | |
|---|---|---|---|
| 2017/0224733 | A1 | 8/2017 | Badie |
| 2020/0061114 | A1 | 2/2020 | Abate-Daga |
| 2021/0000875 | A1 | 1/2021 | Tampella et al. |

FOREIGN PATENT DOCUMENTS

| | | |
|---|---|---|
| JP | 2016503295 A | 2/2016 |
| JP | 2016525881 A | 9/2016 |
| JP | 2016195601 A | 11/2016 |
| JP | 2017529081 A | 10/2017 |
| JP | 2017534262 A | 11/2017 |
| WO | WO2014031687 A1 | 2/2014 |
| WO | WO2014072888 A1 | 5/2014 |
| WO | WO2016044811 A1 | 3/2016 |
| WO | WO2016123142 A1 | 8/2016 |
| WO | WO2017015490 A1 | 1/2017 |
| WO | WO2017040930 A2 | 3/2017 |
| WO | WO2017172981 A2 | 10/2017 |
| WO | WO2017214092 A1 | 12/2017 |
| WO | WO2018023093 A1 | 2/2018 |
| WO | WO2019178078 A1 | 9/2019 |

OTHER PUBLICATIONS

Brown, et al., "Bioactivity and Safety of IL13RALPHA2-Redirected Chimeric Antigen Receptor CD8+ T Cells in Patients with Recurrent Glioblastoma," Clinical Cancer Research, vol. 21, No. 18, 2015, pp. 4062-4072.
Brown, et al., "Optimization of IL13RALPHA2-Targeted Chimeric Antigen Receptor T Cells for Improved Anti-tumor Efficacy against Glioblastoma," Molecular Therapy, vol. 26, No. 1, 2018, pp. 31-44.
Brown, et al., "Regression of Glioblastoma after Chimeric Antigen Receptor T-Cell Therapy," The New England Journal of Medicine, vol. 375, No. 26, 2016, pp. 2561-2569.
Debinski, et al., "New Agents for Targeting of IL-13RA2 Expressed in Primary Human and Canine Brain Tumors," PLoS One, vol. 8, No. 10, 15 pages.
Kahlon, et al., "Specific Recognition and Killing of Glioblastoma Multiforme by Interleukin 13-Zetakine Redirected Cytolytic T Cells," Cancer Research, vol. 64, No. 24, 2004, pp. 9160-9166.
Office Action Dated Jan. 18, 2021 for Mexican Application No. MX/a/2020/009463, 3 pages.
Papageorgis, et al., "Targeting IL 13Ralpha2 activates STAT6-TP63 pathway to suppress breast cancer lung metastasis," Breast Cancer Research, vol. 17, No. 98, 2015, 15 pages.

(Continued)

*Primary Examiner* — Michael D Pak
(74) *Attorney, Agent, or Firm* — Lee & Hayes, P.C.

(57) ABSTRACT

Some embodiments of the methods and compositions provided herein include cells having membrane-tethered. IL13 mutein-directed zetakine receptors, such as those which specifically bind to the IL-13 receptor alpha 2 (IL13Ra2) at a 50-fold higher affinity than wild-type IL-13, and methods of cell-based immunotherapy targeting cancer cells, such as cells of solid tumors, using these compositions. In some embodiments, the receptors include spacer regions, such as particular spacer regions designed to provide certain advantages.

15 Claims, 14 Drawing Sheets
Specification includes a Sequence Listing.

(56) References Cited

OTHER PUBLICATIONS

PCT Search Report & Written Opinion for Application No. PCT/US2019/021823, mailed May 17, 2019, 9 pages.

PCT Search Report & Written Opinion for Application No. PCT/US2019/021833, mailed Jun. 10, 2019, 9 pages.

Sengupta, et al., "Interleukin-13 Receptor Alpha 2-Targeted Glioblastoma Immunotherapy," BioMed Research International, vol. 2014, No. 952128, 2014, 8 pages.

Tu, et al., "IL-13 receptor ALPHA2 stimulates human glioma cell growth and metastasis through the Src/PI3K/Akt/mTOR signaling pathway," Tumor Biology, vol. 37, 2016, pp. 14701-14709.

Eurasian Office Action mailed Nov. 14, 2022 for Eurasian Patent Application No. 202091984, a foreign counterpart to U.S. Appl. No. 16/979,475, 5 pages.

Paszkiewicz, "Development of a truncated EGFR marker as a safeguard for adoptive T cell therapy", Jun. 16, 2014, 192 pages.

Wang, et al, "Engineered IL13 variants direct specificity of IL13Ra2-targeted CAR T cell therapy", Jun. 15, 2016, 12 pages.

Office Action Dated Mar. 9, 2023 for European Application No. 19767433.6, 5 pages.

Eurasian Office Action mailed Apr. 19, 2023 for Eurasian patent application No., a foreign counterpart of U.S. Appl. No. 16/979,471, 3 pages.

Eurasian Office Action mailed Apr. 27, 2023 for Eurasian Patent Application No. 202091984, a foreign counterpart to U.S. Appl. No. 16/979,475, 3 pages.

Liu, et al., "Systematic comparison of 2A peptides for cloning multi-genes in a polycistronic vector", Scientific Reports, 7:2193, May 19, 2017, 9 pages.

Hashimoto, "Immunotherapy for Central Nervous System Tumors," J. Kyoto Pref. Univ. Med., 2017, vol. 126, pp. 405-415.

Jonnalagadda, Mahesh, et al. "Efficient selection of genetically modified human T cells using methotrexate-resistant human dihydrofolate reductase." Gene therapy 20.8 (2013): 853-860.

Japanese Office Action mailed Jan. 17, 2023 for Japanese Patent Application No. 2020-548920, a foreign counterpart to U.S. Appl. No. 16/979,471, 11 pages.

Japanese Office Action mailed Jan. 31, 2023 for Japanese Patent Application No. 2020-549002, a foreign counterpart to U.S. Appl. No. 16/979,475, 5 pages.

Australian Office Action mailed Aug. 24, 2023 for Australian Patent Application No. 2019234580, a foreign counterpart to U.S. Appl. No. 16/979,475, 3 pages.

Japanese Office Action mailed Jul. 25, 2023 for Japanese Patent Application No. 2020-548920, a foreign counterpart to U.S. Appl. No. 16/979,471, 7 pages.

Brown, et al, "Regression of Glioblastoma after Chimeric Antigen Receptor T-Cell Therapy", New England Journal of Medicine, vol. 375, No. 26, Dec. 29, 2016, pp. 2561-2569.

Extended European Search Report Dated Nov. 24, 2021 for European Application No. 19768040.8, 11 pages.

Extended European Search Report mailed Dec. 7, 2021 for European Patent Application No. 19767433.6, 9 pages.

Hedge, et al., "Tandem CAR T cells targeting HER2 and IL13Ra2 mitigate tumor antigen escape," The Journal of Clinical Investigation, vol. 126, No. 8, 2016, pp. 3036-3052.

Kacherovsky, et al, "Multiplexed Gene Transfer to a Human T-Cell Line by Combining Sleeping Beauty Transposon System with Methotrexate Selection", Biotechnology and Bioengineering, vol. 112, No. 7, Mar. 23, 2015, pp. 1429-1436.

Krenciute, et al., "Characterization and Functional Analysis of scFv-based Chimeric Antigen Receptors to Redirect T Cells to IL13Ra2-positive Glioma," Molecular Therapy, vol. 24, No. 2, 2016, pp. 354-363.

Migliorini, et al., "CAR T-Cell Therapies in Glioblastoma: A First Look," Clinical Cancer Research, vol. 24, No. 3, 2017, 7 pages.

Pituch, et al., "Neural stem cells secreting bispecific T cell engager to induce selective antiglioma activity," PNAS, vol. 118, No. 9, 2021, 11 pages.

Sengupta, Sadhak et al., "Interleukin-13 Receptor Alpha 2-Targeted Glioblastoma Immunotherapy" BioMed Research International, Aug. 2014, pp. 1-8, vol. 2014, Article ID: 952128.

International Search Report for PCT/US2019/021833 dated Jun. 10, 2019.

Israel Office Action Dated Dec. 12, 2023 for Israeli Application No. 277267, 6 pages.

Office Action for Israeli Application No. 277268, Dated Apr. 2, 2024, 10 pages.

Office Action for Korean Application No. 10-2020-7028966, Dated May 7, 2024, 9 pages.

Office Action Dated Feb. 23, 2024 for U.S. Appl. No. 16/979,471, 9 pages.

Office Action for European Application No. 19767433.6, Dated May 23, 2024, 5 pages.

Hudecek, et al., "Receptor Affinity and Extracellular Domain Modifications Affect Tumor Recognition by ROR1-Specific Chimeric Antigen Receptor T Cells", Clinical Cancer Research, vol. 19, No. 12, 2013, pp. 3153-3164.

Office Action for Japanese Application No. 2023-114641, Dated Jul. 9, 2024, 8 pages.

Knudson, et al., "Recent Advances in IL-13Ra2-Directed Cancer Immunotherapy", Frontiers in Immunology. 13: 2022, pp. 1-10.

Office Action for Japanese Application No. 2023-114641, Dated Oct. 29, 2024, 12 pages.

IL13Rα2

- 2e6 T-cells CD8 Mock
- 2e6 T-cells CD8 IL13-zetakine 2GM
- 1e6 T-cells CD8 IL13-zetakine 2GM
- 2e6 T-cells CD8 IL13-zetakine 2GL
- 1e6 T-cells CD8 IL13-zetakine 2GL Tumor Symptom-free Survival
Target: U251T ffLuc, I.C.
Effector: Bulk CD8 CAR Tcells Percent Survival Dyas Post Tumor Inoculation

SEQUENCE LISTING

<160> NUMBER OF SEQ ID NOS: 27

<210> SEQ ID NO 1
<211> LENGTH: 15
<212> TYPE: PRT
<213> ORGANISM: Artificial Sequence
<220> FEATURE:
<223> OTHER INFORMATION: synthesized human IgG1

<400> SEQUENCE: 1

Glu Pro Lys Ser Cys Asp Lys Thr His Thr Cys Pro Pro Cys Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: synthesized human IgG2

<400> SEQUENCE: 2

Glu Arg Lys Cys Cys Val Glu Cys Pro Pro Cys Pro
1               5                   10

<210> SEQ ID NO 3
<211> LENGTH: 61
<212> TYPE: PRT
<213> ORGANISM: Artificial Sequence
<220> FEATURE:
<223> OTHER INFORMATION: synthesized human IgG3

<400> SEQUENCE: 3

-continued

```
Glu Leu Lys Thr Pro Leu Gly Asp Thr His Thr Cys Pro Arg Cys Pro
1               5               10              15

Glu Pro Lys Ser Cys Asp Thr Pro Pro Cys Pro Arg Cys Pro Glu
            20              25              30

Pro Lys Ser Cys Asp Thr Pro Pro Cys Pro Arg Cys Pro Glu Pro
        35              40              45

Lys Ser Cys Asp Thr Pro Pro Pro Cys Pro Arg Cys Pro
    50              55              60

<210> SEQ ID NO 4
<211> LENGTH: 12
<212> TYPE: PRT
<213> ORGANISM: Artificial Sequence
<220> FEATURE:
<223> OTHER INFORMATION: synthesized human IgG4

<400> SEQUENCE: 4

Glu Ser Lys Tyr Gly Pro Pro Cys Pro Ser Cys Pro
1               5               10

<210> SEQ ID NO 5
<211> LENGTH: 12
<212> TYPE: PRT
<213> ORGANISM: Artificial Sequence
<220> FEATURE:
<223> OTHER INFORMATION: synthesized modified human IgG4

<400> SEQUENCE: 5

Glu Ser Lys Tyr Gly Pro Pro Cys Pro Pro Cys Pro
1               5               10

<210> SEQ ID NO 6
<211> LENGTH: 9
<212> TYPE: PRT
<213> ORGANISM: Artificial Sequence
<220> FEATURE:
<223> OTHER INFORMATION: synthesized modified human IgG4

<400> SEQUENCE: 6

Tyr Gly Pro Pro Cys Pro Pro Cys Pro
1               5

<210> SEQ ID NO 7
<211> LENGTH: 10
<212> TYPE: PRT
<213> ORGANISM: Artificial Sequence
<220> FEATURE:
<223> OTHER INFORMATION: synthesized modified human IgG4

<400> SEQUENCE: 7

Lys Tyr Gly Pro Pro Cys Pro Pro Cys Pro
1               5               10

<210> SEQ ID NO 8
<211> LENGTH: 13
<212> TYPE: PRT
<213> ORGANISM: Artificial Sequence
<220> FEATURE:
<223> OTHER INFORMATION: synthesized modified human IgG4

<400> SEQUENCE: 8

Glu Val Val Lys Tyr Gly Pro Pro Cys Pro Pro Cys Pro
1               5               10
```

```
<210> SEQ ID NO 9
<211> LENGTH: 12
<212> TYPE: PRT
<213> ORGANISM: Artificial Sequence
<220> FEATURE:
<223> OTHER INFORMATION: S spacer

<400> SEQUENCE: 9

Glu Ser Lys Tyr Gly Pro Pro Cys Pro Pro Cys Pro
1               5                   10

<210> SEQ ID NO 10
<211> LENGTH: 119
<212> TYPE: PRT
<213> ORGANISM: Artificial Sequence
<220> FEATURE:
<223> OTHER INFORMATION: M spacer

<400> SEQUENCE: 10

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
            115

<210> SEQ ID NO 11
<211> LENGTH: 229
<212> TYPE: PRT
<213> ORGANISM: Artificial Sequence
<220> FEATURE:
<223> OTHER INFORMATION: L spacer

<400> SEQUENCE: 11

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125
```

-continued

```
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 12
<211> LENGTH: 8740
<212> TYPE: DNA
<213> ORGANISM: Artificial Sequence
<220> FEATURE:
<223> OTHER INFORMATION: Vector sequence including: IL13zetakine-IgG4
      hinge-CH3-CD28tm/4-1BB-zeta-T2A-EGFRt

<400> SEQUENCE: 12
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac cctttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggggaga     360 attagatcga tgggaaaaaa ttcggttaag gccaggggga agaaaaaat ataaattaaa      420 acatatagta tgggcaagca gggagctaga acgattcgca gttaatcctg gcctgttaga     480
aacatcagaa ggctgtagac aaatactggg acagctacaa ccatcccttc agacaggatc     540
agaagaactt agatcattat ataatacagt agcaaccctc tattgtgtgc atcaaaggat     600
agagataaaa gacaccaagg aagctttaga caagatagag gaagagcaaa acaaaagtaa     660
gaaaaaagca cagcaagcag cagctgacac aggacacagc aatcaggtca gccaaaatta     720
ccctatagtg cagaacatcc aggggcaaat ggtacatcag gccatatcac ctagaacttt     780
aaatgcatgg gtaaaagtag tagaagagaa ggctttcagc ccagaagtga tacccatgtt     840
ttcagcatta tcagaaggag ccaccccaca agatttaaac accatgctaa acacagtggg     900
gggacatcaa gcagccatgc aaatgttaaa agagaccatc aatgaggaag ctgcaggcaa     960
agagaagagt ggtgcagaga gaaaaaagag cagtgggaat aggagctttg ttccttgggt    1020
tcttgggagc agcaggaagc actatgggcg cagcgtcaat gacgctgacg gtacaggcca    1080
gacaattatt gtctggtata gtgcagcagc agaacaattt gctgagggct attgaggcgc    1140
aacagcatct gttgcaactc acagtctggg gcatcaagca gctccaggca agaatcctgg    1200
ctgtggaaag atacctaaag gatcaacagc tcctggggat ttggggttgc tctggaaaac    1260
tcatttgcac cactgctgtg ccttggatct acaaatggca gtattcatcc acaatttttaa    1320 aagaaaaggg gggattgggg ggtacagtgc aggggaaaga atagtagaca taatagcaac    1380
```

-continued

```
agacatacaa actaaagaat tacaaaaaca aattacaaaa attcaaaatt ttcgggttta      1440
ttacagggac agcagagatc cagtttgggg atcaattgca tgaagaatct gcttagggtt      1500
aggcgttttg cgctgcttcg cgaggatctg cgatcgctcc ggtgcccgtc agtgggcaga      1560
gcgcacatcg cccacagtcc ccgagaagtt gggggggagg gtcggcaatt gaaccggtgc      1620
ctagagaagg tggcgcgggg taaactggga aagtgatgtc gtgtactggc tccgcctttt      1680
tcccgagggt gggggagaac cgtatataag tgcagtagtc gccgtgaacg ttcttttttcg      1740 caacgggttt gccgccagaa cacagctggg ctagcgttta aacgggccct ctagagccgc      1800
caccatgctt ctcctggtga caagccttct gctctgtgag ttaccacacc cagcattcct      1860
cctgatccca ggccctgtgc ctccctctac agccctcagg tacctcattg aggagctggt      1920
caacatcacc cagaaccaga aggctccgct ctgcaatggc agcatggtat ggagcatcaa      1980
cctgacagct ggcatgtact gtgcagccct ggaatccctg atcaacgtgt caggctgcag      2040
tgccatcgag aagacccaga ggatgctgag cggattctgc ccgcacaagg tctcagctgg      2100
gcagttttcc agcttgcatg tccgagacac caaaatcgag gtggcccagt ttgtaaagga      2160
cctgctctta catttaaaga aactttttcg cgagggacgg ttcaagaatc taagtaccgg      2220
accgccctgc cccccttgcc ctggccagcc tagagaaccc caggtgtaca ccctgcctcc      2280
cagccaggaa gagatgacca agaaccaggt gtccctgacc tgcctggtca aaggcttcta      2340
ccccagcgat atcgccgtgg aatgggagag caacggccag cccgagaaca actacaagac      2400 cacccccccct gtgctggaca gcgacggcag cttcttcctg tactcccggc tgaccgtgga      2460
caagagccgg tggcaggaag gcaacgtctt cagctgcagc gtgatgcacg aggccctgca      2520
caaccactac acccagaagt ccctgagcct gagcctgggc aagatgttct gggtgctggt      2580
ggtggtcgga ggcgtgctgg cctgctacag cctgctggtc accgtggcct tcatcatctt      2640
ttgggtgaaa cggggcagaa agaaactcct gtatatattc aaacaaccat ttatgagacc      2700
agtacaaact actcaagagg aagatggctg tagctgccga tttccagaag aagaagaagg      2760
aggatgtgaa ctgcgggtga agttcagcag aagcgccgac gcccctgcct accagcaggg      2820
ccagaatcag ctgtacaacg agctgaacct gggcagaagg gaagagtacg acgtcctgga      2880
taagcggaga ggccgggacc ctgagatggg cggcaagcct cggcggaaga accccccagga      2940 aggcctgtat aacgaactgc agaaagacaa gatggccgag gcctacagcg agatcggcat      3000
gaagggcgag cggaggcggg gcaagggcca cgacggcctg tatcagggcc tgtccaccgc      3060
caccaaggat acctacgacg ccctgcacat gcaggccctg ccccccaaggc tcgagggcgg      3120 cggagagggc agaggaagtc ttctaacatg cggtgacgtg gaggagaatc ccggccctag      3180
gatgcttctc ctggtgacaa gccttctgct ctgtgagtta ccacacccag cattcctcct      3240
gatcccacgc aaagtgtgta acggaatagg tattggtgaa tttaaagact cactctccat      3300
aaatgctacg aatattaaac acttcaaaaa ctgcacctcc atcagtggcg atctccacat      3360
cctgccggtg gcatttaggg gtgactcctt cacacatact cctcctctgg atccacagga      3420
actggatatt ctgaaaaccg taaaggaaat cacagggttt ttgctgattc aggcttggcc      3480
tgaaaacagg acgacctcc atgcctttga gaacctagaa atcatacgcg gcaggaccaa      3540
gcaacatggt cagttttctc ttgcagtcgt cagcctgaac ataacatcct tgggattacg      3600
ctccctcaag gagataagtg atggagatgt gataatttca ggaaacaaaa atttgtgcta      3660
tgcaaataca ataaactgga aaaaactgtt tgggacctcc ggtcagaaaa ccaaaaattat      3720 aagcaacaga ggtgaaaaca gctgcaaggc cacaggccag gtctgccatg ccttgtgctc      3780
```

-continued

```
ccccgagggc tgctgggggcc cggagcccag ggactgcgtc tcttgccgga atgtcagccg   3840
aggcagggaa tgcgtggaca agtgcaacct tctggagggt gagccaaggg agtttgtgga   3900
gaactctgag tgcatacagt gccacccaga gtgcctgcct caggccatga acatcacctg   3960
cacaggacgg ggaccagaca actgtatcca gtgtgcccac tacattgacg cccccactg    4020 cgtcaagacc tgcccggcag gagtcatggg agaaaacaac accctggtct ggaagtacgc   4080
agacgccggc catgtgtgcc acctgtgcca tccaaactgc acctacggat gcactgggcc   4140
aggtcttgaa ggctgtccaa cgaatgggcc taagatcccg tccatcgcca ctgggatggt   4200 gggggcccctc ctcttgctgc tggtggtggc cctggggatc ggcctcttca tgtgagcggc   4260
cgctctagac ccgggctgca ggaattcgat atcaagctta tcgataatca acctctggat   4320
tacaaaattt gtgaaagatt gactggtatt cttaactatg ttgctccttt tacgctatgt   4380
ggatacgctg ctttaatgcc tttgtatcat gctattgctt cccgtatggc tttcattttc   4440
tcctccttgt ataaatcctg gttgctgtct ctttatgagg agttgtggcc cgttgtcagg   4500
caacgtggcg tggtgtgcac tgtgtttgct gacgcaaccc ccactggttg gggcattgcc   4560
accacctgtc agctcctttc cgggactttc gctttccccc tccctattgc cacggcggaa   4620
ctcatcgccg cctgccttgc ccgctgctgg acaggggctc ggctgttggg cactgacaat   4680
tccgtggtgt tgtcggggaa atcatcgtcc tttccttggc tgctcgcctg tgttgccacc   4740
tggattctgc gcgggacgtc cttctgctac gtcccttcgg ccctcaatcc agcggacctt   4800
ccttcccgcg cctgctgcc ggctctgcgg cctcttccgc gtcttcgcct tcgccctcag   4860
acgagtcgga tctccctttg gccgcctcc ccgcatcgat accgtcgact agccgtacct   4920
ttaagaccaa tgacttacaa ggcagctgta gatcttagcc acttttaaa agaaaagggg   4980 ggactggaag ggctaattca ctcccaaaga agacaagatc tgcttttgc ctgtactggg   5040 tctctctggt tagaccagat ctgagcctgg gagctctctg gctaactagg gaacccactg   5100
cttaagcctc aataaagctt gccttgagtg cttcaagtag tgtgtgcccg tctgttgtgt   5160
gactctggta actagagatc cctcagaccc ttttagtcag tgtggaaaat ctctagcaga   5220
attcgatatc aagcttatcg ataccgtcga cctcgagggg gggcccggta ccgagctcgg   5280
atccactagt ccagtgtggt ggaattctgc agatatccag cacagtggcg gccactcaag   5340
tctggagggc acgttaaaac ccgctgatca gcctcgactg tgccttctag ttgccagcca   5400
tctgttgttt gcccctcccc cgtgccttcc ttgaccctgg aaggtgccac tcccactgtc   5460
ctttcctaat aaaatgagga aattgcatcg cattgtctga gtaggtgtca ttctattctg   5520
gggggtgggg tggggcagga cagcaagggg gaggattggg aagacaatag caggcatgct   5580
ggggatgcgg tgggctctat ggcttctact gggcggtttt atggacagca agcgaaccgg   5640
aattgccagc tggggcgccc tctggtaagg ttgggaagcc ctgcaaagta aactggatgg   5700
ctttctcgcc gccaaggatc tgatggcgca ggggatcaag ctctgatcaa gagacaggat   5760
gaggatcgtt tcgcatgatt gaacaagatg gattgcacgc aggttctccg gccgcttggg   5820
tggagaggct attcggctat gactgggcac aacagacaat cggctgctct gatgccgccg   5880
tgttccggct gtcagcgcag gggcgcccgg ttctttttgt caagaccgac ctgtccggtg   5940
ccctgaatga actgcaagac gaggcagcgc ggctatcgtg gctggccacg acgggcgttc   6000
cttgcgcagc tgtgctcgac gttgtcactg aagcgggaag ggactggctg ctattgggcg   6060
aagtgccggg gcaggatctc ctgtcatctc accttgctcc tgccgagaaa gtatccatca   6120
```

```
tggctgatgc aatgcggcgg ctgcatacgc ttgatccggc tacctgccca ttcgaccacc      6180
aagcgaaaca tcgcatcgag cgagcacgta ctcggatgga agccggtctt gtcgatcagg      6240
atgatctgga cgaagagcat caggggctcg cgccagccga actgttcgcc aggctcaagg      6300
cgagcatgcc cgacggcgag gatctcgtcg tgacccatgg cgatgcctgc ttgccgaata      6360
tcatggtgga aaatggccgc ttttctggat tcatcgactg tggccggctg ggtgtggcag      6420
accgctatca ggacatagcg ttggctaccc gtgatattgc tgaagagctt ggcggcgaat      6480
gggctgaccg cttcctcgtg ctttacggta tcgccgctcc cgattcgcag cgcatcgcct      6540
tctatcgcct tcttgacgag ttcttctgaa ttattaacgc ttacaatttc ctgatgcggt      6600
attttctcct tacgcatctg tgcggtattt cacaccgcat acaggtggca cttttcgggg      6660
aaatgtgcgc ggaacccta tttgtttatt tttctaaata cattcaaata tgtatccgct      6720
catgaccaaa atcccttaac gtgagttttc gttccactga gcgtcagacc ccgtagaaaa      6780
gatcaaagga tcttcttgag atcctttttt tctgcgcgta atctgctgct tgcaaacaaa      6840
aaaaccaccg ctaccagcgg tggtttgttt gccggatcaa gagctaccaa ctcttttccc      6900
gaaggtaact ggcttcagca gagcgcagat accaaatact gttcttctag tgtagccgta      6960
gttaggccac cacttcaaga actctgtagc accgcctaca tacctcgctc tgctaatcct      7020
gttaccagtg gctgctgcca gtggcgataa gtcgtgtctt accgggttgg actcaagacg      7080
atagttaccg gataaggcgc agcggtcggg ctgaacgggg ggttcgtgca cacagcccag      7140
cttggagcga acgacctaca ccgaactgag atacctacag cgtgagctat gagaaagcgc      7200
cacgcttccc gaagggagaa aggcggacag gtatccggta agcggcaggg tcggaacagg      7260
agagcgcacg agggagcttc caggggggaaa cgcctggtat ctttatagtc ctgtcgggtt      7320
tcgccacctc tgacttgagc gtcgattttt gtgatgctcg tcagggggc ggagcctatg      7380 gaaaaacgcc agcaacgcgg cctttttacg gttcctggcc ttttgctggc cttttgctca      7440
catgttcttt cctgcgttat cccctgattc tgtggataac cgtattaccg cctttgagtg      7500
agctgatacc gctcgccgca gccgaacgac cgagcgcagc gagtcagtga gcgaggaagc      7560
ggaagagcgc ccaatacgca aaccgcctct ccccgcgcgt tggccgattc attaatgcag      7620
ctggcacgac aggtttcccg actggaaagc gggcagtgag cgcaacgcaa ttaatgtgag      7680
ttagctcact cattaggcac cccaggcttt cacttttatg cttccggctc gtatgttgtg      7740
tggaattgtg agcggataac aatttcacac aggaaacagc tatgaccatg attacgccaa      7800
gctcgaaatt aaccctcact aaagggaaca aaagctggag ctccaccgcg gtggcggcct      7860
cgaggtcgag atccggtcga ccagcaacca tagtcccgcc cctaactccg cccatcccgc      7920
ccctaactcc gcccagttcc gcccattctc cgccccatgg ctgactaatt tttttttattt      7980 atgcagaggc cgaggccgcc tcggcctctg agctattcca gaagtagtga ggaggctttt      8040
ttggaggcct aggcttttgc aaaaagcttc gacggtatcg attggctcat gtccaacatt      8100
accgccatgt tgacattgat tattgactag ttattaatag taatcaatta cggggtcatt      8160
agttcatagc ccatatatgg agttccgcgt tacataactt acggtaaatg gcccgcctgg      8220
ctgaccgccc aacgaccccc gcccattgac gtcaataatg acgtatgttc ccatagtaac      8280
gccaataggg actttccatt gacgtcaatg ggtggagtat ttacggtaaa ctgcccactt      8340
ggcagtacat caagtgtatc atatgccaag tacgccccct attgacgtca atgacggtaa      8400
atggcccgcc tggcattatg cccagtacat gaccttatgg gactttccta cttggcagta      8460
catctacgta ttagtcatcg ctattaccat ggtgatgcgg ttttggcagt acatcaatgg      8520
```

```
gcgtggatag cggtttgact cacggggatt tccaagtctc caccccattg acgtcaatgg    8580
gagtttgttt tggcaccaaa atcaacggga ctttccaaaa tgtcgtaaca actccgcccc    8640
attgacgcaa atgggcggta ggcgtgtacg gaattcggag tggcgagccc tcagatcctg    8700
catataagca gctgcttttt gcctgtactg ggtctctctg                          8740
```

<210> SEQ ID NO 13
<211> LENGTH: 8740
<212> TYPE: DNA
<213> ORGANISM: Artificial Sequence
<220> FEATURE:
<223> OTHER INFORMATION: Vector sequence including: IL13zetakine-IgG4
      hinge-CH3-CD28tm/4-1BB-zeta-T2A-EGFRt

<400> SEQUENCE: 13

```
gttagaccag atctgagcct gggagctctc tggctaacta gggaacccac tgcttaagcc     60
tcaataaagc ttgccttgag tgcttcaagt agtgtgtgcc cgtctgttgt gtgactctgg    120
taactagaga tccctcagac cctttttagtc agtgtggaaa atctctagca gtggcgcccg    180
aacagggact tgaaagcgaa agggaaacca gaggagctct ctcgacgcag gactcggctt    240
gctgaagcgc gcacggcaag aggcgagggg cggcgactgg tgagtacgcc aaaaattttg    300
actagcggag gctagaagga gagagatggg tgcgagagcg tcagtattaa gcggggggaga    360 attagatcga tgggaaaaaa ttcggttaag gccagggggga aagaaaaaat ataaattaaa    420
acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca gatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt gggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740 caacgggttt gccgccagaa cacagctggg ctagcgttta aacgggccct ctagagccgc   1800
```

```
caccatgctt ctcctggtga caagccttct gctctgtgag ttaccacacc cagcattcct     1860
cctgatccca ggccctgtgc ctccctctac agccctcagg tacctcattg aggagctggt     1920
caacatcacc cagaaccaga aggctccgct ctgcaatggc agcatggtat ggagcatcaa     1980
cctgacagct ggcatgtact gtgcagccct ggaatccctg atcaacgtgt caggctgcag     2040
tgccatcgag aagacccaga ggatgctgag cggattctgc ccgcacaagg tctcagctgg     2100
gcagttttcc agcttgcatg tccgagacac caaaatcgag gtggcccagt ttgtaaagga     2160
cctgctctta catttaaaga aacttttttcg cgagggacgg ttcaagaatc taagtaccgg     2220
accgccctgc ccccccttgcc ctggccagcc tagagaaccc caggtgtaca ccctgcctcc     2280
cagccaggaa gagatgacca agaaccaggt gtccctgacc tgcctggtca aaggcttcta     2340
ccccagcgat atcgccgtgg aatgggagag caacggccag cccgagaaca actacaagac     2400 cacccccccct gtgctggaca gcgacggcag cttcttcctg tactcccggc tgaccgtgga     2460
caagagccgg tggcaggaag gcaacgtctt cagctgcagc gtgatgcacg aggccctgca     2520
caaccactac acccagaagt ccctgagcct gagcctgggc aagatgttct gggtgctggt     2580
ggtggtcgga ggcgtgctgg cctgctacag cctgctggtc accgtggcct tcatcatctt     2640
ttgggtgaaa cggggcagaa agaaactcct gtatatattc aaacaaccat ttatgagacc     2700
agtacaaact actcaagagg aagatggctg tagctgccga tttccagaag aagaagaagg     2760
aggatgtgaa ctgcgggtga agttcagcag aagcgccgac gccctgcct accagcaggg     2820 ccagaatcag ctgtacaacg agctgaacct gggcagaagg gaagagtacg acgtcctgga     2880
taagcggaga ggccgggacc ctgagatggg cggcaagcct cggcggaaga accccccagga     2940 aggcctgtat aacgaactgc agaaagacaa gatggccgag gcctacagcg agatcggcat     3000
gaagggcgag cggaggcggg gcaagggcca cgacggcctg tatcagggcc tgtccaccgc     3060
caccaaggat acctacgacg ccctgcacat gcaggccctg cccccaaggc tcgagggcgg     3120
cggagagggc agaggaagtc ttctaacatg cggtgacgtg gaggagaatc ccggccctag     3180
gatgcttctc ctggtgacaa gccttctgct ctgtgagtta ccacacccag cattcctcct     3240
gatcccacgc aaagtgtgta acggaatagg tattggtgaa tttaaagact cactctccat     3300
aaatgctacg aatattaaac acttcaaaaa ctgcacctcc atcagtggcg atctccacat     3360
cctgccggtg gcatttaggg gtgactcctt cacacatact cctcctctgg atccacagga     3420
actggatatt ctgaaaaccg taaaggaaat cacagggttt ttgctgattc aggcttggcc     3480
tgaaaacagg acgacctcc atgcctttga gaacctagaa atcatacgcg gcaggaccaa     3540
gcaacatggt cagttttctc ttgcagtcgt cagcctgaac ataacatcct gggattacg     3600 ctccctcaag gagataagtg atggagatgt gataatttca ggaaacaaaa atttgtgcta     3660
tgcaaataca ataaactgga aaaaactgtt tgggacctcc ggtcagaaaa ccaaaattat     3720
aagcaacaga ggtgaaaaca gctgcaaggc cacaggccag gtctgccatg ccttgtgctc     3780
ccccgagggc tgctggggcc cggagcccag ggactgcgtc tcttgccgga atgtcagccg     3840
aggcagggaa tgcgtggaca agtgcaacct tctggagggt gagccaaggg agtttgtgga     3900
gaactctgag tgcatacagt gccacccaga gtgcctgcct caggccatga acatcacctg     3960
cacaggacgg ggaccagaca actgtatcca gtgtgcccac tacattgacg gcccccactg     4020
cgtcaagacc tgcccggcag gagtcatggg agaaaacaac accctggtct ggaagtacgc     4080
agacgccggc catgtgtgcc acctgtgcca tccaaactgc acctacggat gcactgggcc     4140
```

-continued

```
aggtcttgaa ggctgtccaa cgaatgggcc taagatcccg tccatcgcca ctgggatggt   4200
gggggccctc ctcttgctgc tggtggtggc cctggggatc ggcctcttca tgtgagcggc   4260
cgctctagac ccgggctgca ggaattcgat atcaagctta tcgataatca acctctggat   4320
tacaaaattt gtgaaagatt gactggtatt cttaactatg ttgctccttt tacgctatgt   4380
ggatacgctg ctttaatgcc tttgtatcat gctattgctt cccgtatggc tttcattttc   4440
tcctccttgt ataaatcctg gttgctgtct ctttatgagg agttgtggcc cgttgtcagg   4500
caacgtggcg tggtgtgcac tgtgtttgct gacgcaaccc ccactggttg gggcattgcc   4560
accacctgtc agctcctttc cgggactttc gctttccccc tccctattgc cacggcggaa   4620
ctcatcgccg cctgccttgc ccgctgctgg acaggggctc ggctgttggg cactgacaat   4680
tccgtggtgt tgtcggggaa atcatcgtcc tttccttggc tgctcgcctg tgttgccacc   4740
tggattctgc gcgggacgtc cttctgctac gtcccttcgg ccctcaatcc agcggacctt   4800
ccttcccgcg cctgctgccc ggctctgcgg cctcttccgc gtcttcgcct tcgccctcag   4860
acgagtcgga tctccctttg gccgcctccc ccgcatcgat accgtcgact agccgtacct   4920
ttaagaccaa tgacttacaa ggcagctgta gatcttagcc actttttaaa agaaaagggg   4980
ggactggaag ggctaattca ctcccaaaga agacaagatc tgcttttgc ctgtactggg   5040 tctctctggt tagaccagat ctgagcctgg gagctctctg gctaactagg gaacccactg   5100
cttaagcctc aataaagctt gccttgagtg cttcaagtag tgtgtgcccg tctgttgtgt   5160
gactctggta actagagatc cctcagaccc ttttagtcag tgtggaaaat ctctagcaga   5220
attcgatatc aagcttatcg ataccgtcga cctcgagggg gggcccggta ccgagctcgg   5280
atccactagt ccagtgtggt ggaattctgc agatatccag cacagtggcg gccactcaag   5340 tctgagggc acgttaaaac ccgctgatca gcctcgactg tgccttctag ttgccagcca   5400
tctgttgttt gcccctcccc cgtgccttcc ttgaccctgg aaggtgccac tcccactgtc   5460
ctttcctaat aaaatgagga aattgcatcg cattgtctga gtaggtgtca ttctattctg   5520
gggggtgggg tggggcagga cagcaagggg gaggattggg aagacaatag caggcatgct   5580
ggggatgcgg tgggctctat ggcttctact gggcggtttt atggacagca agcgaaccgg   5640
aattgccagc tggggcgccc tctggtaagg ttgggaagcc ctgcaaagta aactggatgg   5700
ctttctcgcc gccaaggatc tgatggcgca ggggatcaag ctctgatcaa gagacaggat   5760
gaggatcgtt tcgcatgatt gaacaagatg gattgcacgc aggttctccg gccgcttggg   5820
tggagaggct attcggctat gactgggcac aacagacaat cggctgctct gatgccgccg   5880
tgttccggct gtcagcgcag gggcgcccgg ttcttttgt caagaccgac ctgtccggtg   5940
ccctgaatga actgcaagac gaggcagcgc ggctatcgtg ctggccacg acgggcgttc   6000 cttgcgcagc tgtgctcgac gttgtcactg aagcgggaag ggactggctg ctattgggcg   6060
aagtgccggg gcaggatctc ctgtcatctc accttgctcc tgccgagaaa gtatccatca   6120
tggctgatgc aatgcggcgg ctgcatacgc ttgatccggc tacctgccca ttcgaccacc   6180
aagcgaaaca tcgcatcgag cgagcacgta ctcggatgga agccggtctt gtcgatcagg   6240
atgatctgga cgaagagcat caggggctcg cgccagccga actgttcgcc aggctcaagg   6300
cgagcatgcc cgacggcgag gatctcgtcg tgacccatgg cgatgcctgc ttgccgaata   6360
tcatggtgga aaatggccgc ttttctggat tcatcgactg tggccggctg ggtgtggcag   6420
accgctatca ggacatagcg ttggctaccc gtgatattgc tgaagagctt ggcggcgaat   6480
gggctgaccg cttcctcgtg ctttacggta tcgccgctcc cgattcgcag cgcatcgcct   6540
```

-continued

```
tctatcgcct tcttgacgag ttcttctgaa ttattaacgc ttacaatttc ctgatgcggt     6600
attttctcct tacgcatctg tgcggtattt cacaccgcat acaggtggca cttttcgggg     6660
aaatgtgcgc ggaacccta tttgtttatt tttctaaata cattcaaata tgtatccgct      6720
catgaccaaa atcccttaac gtgagttttc gttccactga gcgtcagacc ccgtagaaaa     6780
gatcaaagga tcttcttgag atcctttttt tctgcgcgta atctgctgct tgcaaacaaa     6840
aaaaccaccg ctaccagcgg tggtttgttt gccggatcaa gagctaccaa ctcttttttcc    6900 gaaggtaact ggcttcagca gagcgcagat accaaatact gttcttctag tgtagccgta     6960
gttaggccac cacttcaaga actctgtagc accgcctaca tacctcgctc tgctaatcct     7020
gttaccagtg gctgctgcca gtggcgataa gtcgtgtctt accgggttgg actcaagacg     7080
atagttaccg gataaggcgc agcggtcggg ctgaacgggg ggttcgtgca cacagcccag     7140
cttggagcga acgacctaca ccgaactgag atacctacag cgtgagctat gagaaagcgc     7200
cacgcttccc gaagggagaa aggcggacag gtatccggta agcggcaggg tcggaacagg     7260
agagcgcacg agggagcttc caggggggaaa cgcctggtat ctttatagtc ctgtcgggtt    7320
tcgccacctc tgacttgagc gtcgattttt gtgatgctcg tcaggggggc ggagcctatg     7380
gaaaaacgcc agcaacgcgg cctttttacg gttcctggcc ttttgctggc cttttgctca     7440
catgttcttt cctgcgttat cccctgattc tgtggataac cgtattaccg cctttgagtg     7500
agctgatacc gctcgccgca gccgaacgac cgagcgcagc gagtcagtga gcgaggaagc     7560
ggaagagcgc ccaatacgca aaccgcctct ccccgcgcgt tggccgattc attaatgcag     7620
ctggcacgac aggtttcccg actggaaagc gggcagtgag cgcaacgcaa ttaatgtgag     7680
ttagctcact cattaggcac cccaggcttt cactttatg cttccggctc gtatgttgtg     7740
tggaattgtg agcggataac aatttcacac aggaaacagc tatgaccatg attacgccaa     7800
gctcgaaatt aaccctcact aaagggaaca aaagctggag ctccaccgcg gtggcggcct     7860
cgaggtcgag atccggtcga ccagcaacca tagtcccgcc cctaactccg cccatcccgc     7920
ccctaactcc gcccagttcc gcccattctc cgccccatgg ctgactaatt ttttttattt    7980
atgcagaggc cgaggccgcc tcggcctctg agctattcca gaagtagtga ggaggctttt    8040
ttggaggcct aggcttttgc aaaaagcttc gacggtatcg attggctcat gtccaacatt    8100
accgccatgt tgacattgat tattgactag ttattaatag taatcaatta cggggtcatt    8160
agttcatagc ccatatatgg agttccgcgt tacataactt acggtaaatg cccgcctgg      8220 ctgaccgccc aacgaccccc gcccattgac gtcaataatg acgtatgttc ccatagtaac     8280
gccaataggg actttccatt gacgtcaatg ggtggagtat ttacggtaaa ctgcccactt     8340
ggcagtacat caagtgtatc atatgccaag tacgccccct attgacgtca atgacggtaa     8400
atggcccgcc tggcattatg cccagtacat gaccttatgg gactttccta cttggcagta    8460
catctacgta ttagtcatcg ctattaccat ggtgatgcgg ttttggcagt acatcaatgg     8520
gcgtggatag cggtttgact cacggggatt tccaagtctc caccccattg acgtcaatgg     8580
gagtttgttt tggcaccaaa atcaacggga ctttccaaaa tgtcgtaaca actccgcccc     8640
attgacgcaa atgggcggta ggcgtgtacg gaattcggag tggcgagccc tcagatcctg     8700
catataagca gctgcttttt gcctgtactg ggtctctctg                           8740
```

<210> SEQ ID NO 14
<211> LENGTH: 187
<212> TYPE: PRT

US 12,606,603 B2

-continued

<213> ORGANISM: Artificial Sequence
<220> FEATURE:
<223> OTHER INFORMATION: synthesized dihydrofolate reductase double
      mutant (DHFRdm)

<400> SEQUENCE: 14

```
Met Val Gly Ser Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185
```

<210> SEQ ID NO 15
<211> LENGTH: 564
<212> TYPE: DNA
<213> ORGANISM: Artificial Sequence
<220> FEATURE:
<223> OTHER INFORMATION: coding sequence of synthesized dihydrofolate
      reductase double mutant (DHFRdm)

<400> SEQUENCE: 15

```
atggttggtt cgctaaactg catcgtcgct gtgtcccaga acatgggcat cggcaagaac      60
ggggacttcc cctggccacc gctcaggaat gaatccagat atttccagag aatgaccaca     120
acctcttcag tagaaggtaa acagaatctg gtgattatgg gtaagaagac ctggttctcc     180
attcctgaga agaatcgacc tttaaagggt agaattaatt tagttctcag cagagaactc     240
aaggaacctc cacaaggagc tcattttctt tccagaagtc tagatgatgc cttaaaactt     300
actgaacaac agaattagc aaataaagta gacatggtct ggatagttgg tggcagttct     360
gtttataagg aagccatgaa tcacccaggc catcttaaac tatttgtgac aaggatcatg     420
caagactttg aaagtgacac gtttttttcca gaaattgatt tggagaaata taaacttctg     480
ccagaatacc caggtgttct ctctgatgtc caggaggaga aaggcattaa gtacaaattt     540
gaagtatatg agaagaatga ttaa                                            564
```

<210> SEQ ID NO 16
<211> LENGTH: 402
<212> TYPE: DNA
<213> ORGANISM: Artificial Sequence

```
<220> FEATURE:
<223> OTHER INFORMATION: Coding sequence of synthesized IL-13 zetakine

<400> SEQUENCE: 16
atgcttctcc tggtgacaag ccttctgctc tgtgagttac cacacccagc attcctcctg      60
atcccaggcc ctgtgcctcc ctctacagcc ctcaggtacc tcattgagga gctggtcaac     120
atcacccaga accagaaggc tccgctctgc aatggcagca tggtatggag catcaacctg     180
acagctggca tgtactgtgc agccctggaa tccctgatca acgtgtcagg ctgcagtgcc     240
atcgagaaga cccagaggat gctgagcgga ttctgcccgc acaaggtctc agctgggcag     300
ttttccagct tgcatgtccg agacaccaaa atcgaggtgg cccagtttgt aaaggacctg     360
ctcttacatt taaagaaact ttttcgcgag ggacggttca ag                        402

<210> SEQ ID NO 17
<211> LENGTH: 134
<212> TYPE: PRT
<213> ORGANISM: Artificial Sequence
<220> FEATURE:
<223> OTHER INFORMATION: Amino acid sequence of synthesized IL-13
      zetakine

<400> SEQUENCE: 17

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
                20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
        50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Lys
        130

<210> SEQ ID NO 18
<211> LENGTH: 28
<212> TYPE: PRT
<213> ORGANISM: Artificial Sequence
<220> FEATURE:
<223> OTHER INFORMATION: synthesized CD28 transmembrane domain (CD28tm)

<400> SEQUENCE: 18

Met Phe Trp Val Leu Val Val Val Gly Gly Val Leu Ala Cys Tyr Ser
1               5                   10                  15

Leu Leu Val Thr Val Ala Phe Ile Ile Phe Trp Val
                20                  25

<210> SEQ ID NO 19
<211> LENGTH: 66
<212> TYPE: DNA
<213> ORGANISM: Artificial Sequence
<220> FEATURE:
```

<223> OTHER INFORMATION: Coding sequence of synthesized granulocyte
      macrophage colony stimulating factor signal sequence (GMCSFss)
      leader

<400> SEQUENCE: 19
atgcttctcc tggtgacaag ccttctgctc tgtgagttac cacacccagc attcctcctg      60
atccca      66

<210> SEQ ID NO 20
<211> LENGTH: 84
<212> TYPE: DNA
<213> ORGANISM: Artificial Sequence
<220> FEATURE:
<223> OTHER INFORMATION: Coding sequence of synthesized CD28
      transmembrane domain (CD28tm)

<400> SEQUENCE: 20
atgttctggg tgctggtggt ggtcggaggc gtgctggcct gctacagcct gctggtcacc      60
gtggccttca tcatcttttg ggtg      84

<210> SEQ ID NO 21
<211> LENGTH: 126
<212> TYPE: DNA
<213> ORGANISM: Artificial Sequence
<220> FEATURE:
<223> OTHER INFORMATION: Coding sequence of synthesized 4-1BB
      intracellular signaling domain

<400> SEQUENCE: 21
aaacggggca gaaagaaact cctgtatata ttcaaacaac catttatgag accagtacaa      60
actactcaag aggaagatgg ctgtagctgc cgatttccag aagaagaaga aggaggatgt     120
gaactg      126

<210> SEQ ID NO 22
<211> LENGTH: 336
<212> TYPE: DNA
<213> ORGANISM: Artificial Sequence
<220> FEATURE:
<223> OTHER INFORMATION: Coding sequence of synthesized CD3zeta
      intracellular signaling domain

<400> SEQUENCE: 22
cgggtgaagt tcagcagaag cgccgacgcc cctgcctacc agcagggcca gaatcagctg      60
tacaacgagc tgaacctggg cagaagggaa gagtacgacg tcctggataa gcggagaggc     120
cgggaccctg agatgggcgg caagcctcgg cggaagaacc cccaggaagg cctgtataac     180
gaactgcaga agacaagat ggccgaggcc tacagcgaga tcggcatgaa gggcgagcgg     240
aggcggggca agggccacga cggcctgtat cagggcctgt ccaccgccac caaggatacc     300
tacgacgccc tgcacatgca ggccctgccc ccaagg      336

<210> SEQ ID NO 23
<211> LENGTH: 72
<212> TYPE: DNA
<213> ORGANISM: Artificial Sequence
<220> FEATURE:
<223> OTHER INFORMATION: synthesized T2A ribosomal skip sequence

<400> SEQUENCE: 23
ctcgagggcg cggagaggg cagaggaagt cttctaacat gcggtgacgt ggaggagaat      60
cccggcccta gg      72

```
<210> SEQ ID NO 24
<211> LENGTH: 1005
<212> TYPE: DNA
<213> ORGANISM: Artificial Sequence
<220> FEATURE:
<223> OTHER INFORMATION: Coding sequence of synthesized truncated
      epidermal growth factor receptor (EGFRt)

<400> SEQUENCE: 24
cgcaaagtgt gtaacggaat aggtattggt gaatttaaag actcactctc cataaatgct     60
acgaatatta aacacttcaa aaactgcacc tccatcagtg gcgatctcca catcctgccg    120
gtggcattta ggggtgactc cttcacacat actcctcctc tggatccaca ggaactggat    180
attctgaaaa ccgtaaagga aatcacaggg tttttgctga ttcaggcttg gcctgaaaac    240
aggacggacc tccatgcctt tgagaaccta gaaatcatac gcggcaggac caagcaacat    300
ggtcagtttt ctcttgcagt cgtcagcctg aacataacat ccttgggatt acgctccctc    360
aaggagataa gtgatggaga tgtgataatt tcaggaaaca aaaatttgtg ctatgcaaat    420
acaataaact ggaaaaaact gtttgggacc tccggtcaga aaccaaaat tataagcaac     480 agaggtgaaa acagctgcaa ggccacaggc caggtctgcc atgccttgtg tcccccgag     540 ggctgctggg gcccggagcc cagggactgc gtctcttgcc ggaatgtcag ccgaggcagg    600
gaatgcgtgg acaagtgcaa ccttctggag ggtgagccaa gggagtttgt ggagaactct    660
gagtgcatac agtgccaccc agagtgcctg cctcaggcca tgaacatcac ctgcacagga    720
cggggaccag acaactgtat ccagtgtgcc cactacattg acggccccca ctgcgtcaag    780
acctgcccgg caggagtcat gggagaaaac aacaccctgg tctggaagta cgcagacgcc    840
ggccatgtgt gccacctgtg ccatccaaac tgcacctacg gatgcactgg gccaggtctt    900
gaaggctgtc caacgaatgg gcctaagatc ccgtccatcg ccactgggat ggtgggggcc    960
ctcctcttgc tgctggtggt ggccctgggg atcggcctct tcatg               1005

<210> SEQ ID NO 25
<211> LENGTH: 36
<212> TYPE: DNA
<213> ORGANISM: Artificial Sequence
<220> FEATURE:
<223> OTHER INFORMATION: Coding sequence of synthesized S spacer

<400> SEQUENCE: 25
gaatctaagt acggaccgcc ctgcccccct tgccct                              36

<210> SEQ ID NO 26
<211> LENGTH: 357
<212> TYPE: DNA
<213> ORGANISM: Artificial Sequence
<220> FEATURE:
<223> OTHER INFORMATION: Coding sequence of synthesized M spacer

<400> SEQUENCE: 26
gaatctaagt acggaccgcc ctgcccccct tgccctggcc agcctagaga accccaggtg     60
tacaccctgc ctcccagcca ggaagagatg accaagaacc aggtgtccct gacctgcctg    120
gtcaaaggct tctaccccag cgatatcgcc gtggaatggg agagcaacgg ccagcccgag    180
aacaactaca agaccacccc ccctgtgctg gacagcgacg gcagcttctt cctgtactcc    240
cggctgaccg tggacaagag ccggtggcag gaaggcaacg tcttcagctg cagcgtgatg    300
cacgaggccc tgcacaacca ctacacccag aagtccctga gcctgagcct gggcaag       357
```

-continued

```
<210> SEQ ID NO 27
<211> LENGTH: 685
<212> TYPE: DNA
<213> ORGANISM: Artificial Sequence
<220> FEATURE:
<223> OTHER INFORMATION: Coding sequence of synthesized L spacer

<400> SEQUENCE: 27
atctaagtac ggaccgccct gccccccttg ccctgccccc gagttcgacg gcggacccag        60
cgtgttcctg ttccccccca agcccaagga caccctgatg atcagccgga cccccgaggt       120
gacctgcgtg gtggtggacg tgagccagga agatcccgag gtccagttca attggtacgt       180
ggacggcgtg gaagtgcaca acgccaagac caagcccaga gaggaacagt tccagagcac       240
ctaccgggtg gtgtctgtgc tgaccgtgct gcaccaggac tggctgaacg gcaaagaata       300
caagtgcaag gtgtccaaca agggcctgcc cagcagcatc gaaaagacca tcagcaaggc       360
caagggccag cctcgcgagc cccaggtgta caccctgcct ccctcccagg aagagatgac       420
caagaaccag gtgtccctga cctgcctggt gaagggcttc tacccagcg acatcgccgt        480 ggagtgggag agcaacggcc agcctgagaa caactacaag accacccctc ccgtgctgga       540
cagcgacggc agcttcttcc tgtacagccg gctgaccgtg gacaagagcc ggtggcagga       600
aggcaacgtc tttagctgca gcgtgatgca cgaggccctg cacaaccact acacccagaa       660
gagcctgagc ctgtccctgg gcaag                                            685
```

IL-13 RECEPTOR ALPHA 2 TARGETED, ZETAKINE DIRECTED T CELL IMMUNOTHERAPY

CROSS-REFERENCE TO RELATED APPLICATIONS

This application is a U.S. National Phase Application of PCT International Application Number PCT/US2019/021833, filed on Mar. 12, 2019, designating the United States of America and published in the English language, which is an International Application of and claims the benefit of priority to U.S. Provisional Application No. 62/643,139, filed on Mar. 14, 2018. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-179NP.txt, created Sep. 9, 2020, which is approximately 36 Kb in size. The information in the electronic format of the Sequence Listing is hereby expressly incorporated by reference in its entirety.

FIELD OF THE INVENTION

Some embodiments of the methods and compositions provided herein include cells having membrane-tethered, IL13 mutein-directed zetakine receptors, such as those, which specifically bind to the IL-13 receptor alpha 2 (IL13Ra2) at a 50-fold higher affinity than wild-type IL-13, and methods of cell-based immunotherapy targeting cancer cells, such as cells of solid tumors, using these compositions. In some embodiments, the receptors include spacer regions, such as particularly selected spacer regions of defined lengths, which are designed to provide specific desirable features to the receptors.

BACKGROUND OF THE INVENTION

Despite significant advances in the understanding of brain cancer, during the last decade, the mortality rate has remained consistent and new innovative therapies are urgently needed. To date, T cell immunotherapy has emerged as a promising cancer therapy supported by remarkable clinical data reporting complete remission in patients with B cell malignancies after administration of T cell CARs targeting CD19. However, there remains a need for further and improved T cell immunotherapies.

SUMMARY OF THE INVENTION

Some embodiments of the methods and compositions provided herein include a nucleic acid encoding a membrane-tethered IL-13 mutein-directed zetakine receptor, the zetakine receptor comprising: an extracellular domain comprising a mutein of IL-13 and a spacer; a transmembrane domain; and an intracellular signaling region, wherein the spacer is interposed between the mutein and transmembrane domain.

In some embodiments, the mutein of IL-13 comprises an amino acid sequence having at least 90% identity with the amino acid sequence of SEQ ID NO:16. In some embodiments, the mutein of IL-13 comprises the amino acid sequence of SEQ ID NO:16.

In some embodiments, the spacer is a peptide spacer.

In some embodiments, the peptide spacer is 110 amino acids or less but not less than 1 or 2 amino acids, such as 15 amino acids or less but not less than 1 or 2 amino acids.

In some embodiments, the spacer comprises, consists of or consists essentially of an IgG4-hinge spacer(S), IgG4 hinge-CH3 spacer (M) or IgG4 hinge-CH2-CH3 (L) spacer.

In some embodiments, the spacer comprises, consists of or consists essentially of an IgG4 hinge-CH3 spacer (M).

In some embodiments, the spacer comprises, consists of or consists essentially of an IgG4 hinge-CH2-CH3 spacer (L).

In some embodiments, the spacer comprises, consists of or consists essentially of an amino acid sequence having at least 90% identity with the amino acid sequence of SEQ ID NO:10. In some embodiments, the spacer comprises, consists of or consists essentially of the amino acid sequence of SEQ ID NO:10.

In some embodiments, the spacer comprises, consists of or consists essentially of an amino acid sequence having at least 90% identity with the amino acid sequence of SEQ ID NO:11. In some embodiments, the spacer comprises, consists of or consists essentially of the amino acid sequence of SEQ ID NO:11.

In some embodiments, the transmembrane domain comprises a CD28 transmembrane domain (CD28tm).

In some embodiments, the intracellular signaling domain comprises all or a portion of a CD3 zeta domain in combination with a co-stimulatory domain selected from the group consisting of CD27, CD28, 4-1BB, OX-40, CD30, CD40, PD-1, ICOS, LFA-1, CD2, CD7, NKG2C, and B7-H3 or combination thereof. In some embodiments, the intracellular signaling region comprises a signaling functional portion of a CD3 zeta domain and a co-stimulatory functional portion of a 4-1BB domain.

Some embodiments also include a sequence encoding a marker. In some embodiments, the marker comprises a truncated form of a cell surface receptor, optionally EGFRt.

Some embodiments also include a dihydrofolate reductase transgene configured for methotrexate selection. In some embodiments, the dihydrofolate reductase transgene is a dihydrofolate reductase double mutant (DHFRdm). In some embodiments, the dihydrofolate reductase double mutant comprises amino acid mutations of L22F and F31S.

Some embodiments also include a sequence encoding a ribosomal skip sequence.

In some embodiments, the ribosomal skip sequence comprises P2A or T2A.

Some embodiments of the methods and compositions provided herein include an expression vector comprising the nucleic acid of any one of the embodiments provided herein. In some embodiments, the vector is a viral vector. In some embodiments, the vector is a lentiviral or adenoviral vector.

Some embodiments of the methods and compositions provided herein include a chimeric receptor polypeptide encoded by the nucleic acid of any one of of the embodiments provided herein.

Some embodiments of the methods and compositions provided herein include a host cell comprising the nucleic acid of any one of of the embodiments provided herein.

In some embodiments, the host cell is a T cell, or a precursor of a T cell.

In some embodiments, the host cell is a CD8+T cytotoxic lymphocyte cell selected from the group consisting of naïve CD8+ T cells, central memory CD8+ T cells, effector memory CD8+ T cells and bulk CD8+ T cells. In some embodiments, the CD8+ cytotoxic T lymphocyte cell is a central memory T cell and, wherein the central memory T cell is positive for CD45RO+, CD62L+, and CD8+.

In some embodiments, the host cell is a CD4+T helper lymphocyte cell selected from the group consisting of naïve CD4+ T cells, central memory CD4+ T cells, effector memory CD4+ T cells, and bulk CD4+ T cells. In some embodiments, the CD4+ helper lymphocyte cell is a naïve CD4+ T cell and, wherein the naïve CD4+ T cell is positive for CD45RA+, CD62L+ and CD4+ and negative for CD45RO.

In some embodiments, the host cell is a precursor T cell.

In some embodiments, the host cell is a hematopoietic stem cell.

Some embodiments of the methods and compositions provided herein include a composition comprising the host cell of any one of the embodiments provided herein, and a pharmaceutically acceptable excipient.

Some embodiments of the methods and compositions provided herein include a method for preparing a host cell, such as a host cell of any one of of the embodiments provided herein, comprising: introducing a nucleic acid of any one of of the embodiments provided herein into a lymphocyte; culturing the lymphocyte in the presence of anti-CD3 and/or anti CD28 antibodies and at least one homeostatic cytokine; and selecting the lymphocyte with a selection reagent, wherein the selection reagent is configured to selectively enrich cells transduced with the nucleic acid or vector.

In some embodiments, the selection reagent comprises methotrexate.

In some embodiments, the lymphocytes have a CD45RA−, CD45RO+, and CD62L+ phenotype. In some embodiments, the lymphocytes are CD8+ or CD4+.

In some embodiments, the cytokine is IL-15, IL-7 and/or IL-21.

Some embodiments also include introducing a second polynucleotide into the host cell, the second polynucleotide encoding a marker protein. In some embodiments, the marker protein is EGFRt.

Some embodiments of the methods and compositions provided herein include a host cell of any one of of the embodiments provided herein for use in a medicament or for use in the treatment or inhibition of a cancer or a solid tumor expressing an IL-13a2 (IL-13Ra2) receptor. In some embodiments, the cancer is a brain cancer. In some embodiments, the cancer is a IL-13Ra-positive malignancy. In some embodiments, the cancer is a glioblastoma tumor. In some embodiments, the cancer is glioblastoma multiforme (GBM).

Some embodiments of the methods and compositions provided herein include a method of treating, inhibiting, or ameliorating a cancer in a subject, comprising: administering the host cell of any one of of the embodiments provided herein to the subject in need thereof. In some embodiments, the cancer is a IL13Ra-positive malignancy. In some embodiments, the cancer is brain cancer. In some embodiments, the cancer is a glioma or glioblastoma tumor. In some embodiments, the cancer is a glioma. In some embodiments, the cancer is glioblastoma multiforme (GBM). In some embodiments, the subject is mammalian. In some embodiments, the subject is human.

Some embodiments also include administering an additional therapy selected from chemotherapy and radiation therapy. In some embodiments, the chemotherapeutic drug comprises electrochemotherapy, alkylating agent, antimetabolite (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and Thioguanine), anti-tumor antibiotic, topoisomerase inhibitor, mitotic inhibitor, corticosteroid, DNA intercalating agent, or checkpoint inhibitor (checkpoint kinase CHK1, CHK2).

5

6 spacer for expression of CD4, CD8, EGFRt, and zetakine expression (as stained by anti-IL13 antibody).

Figure 6:
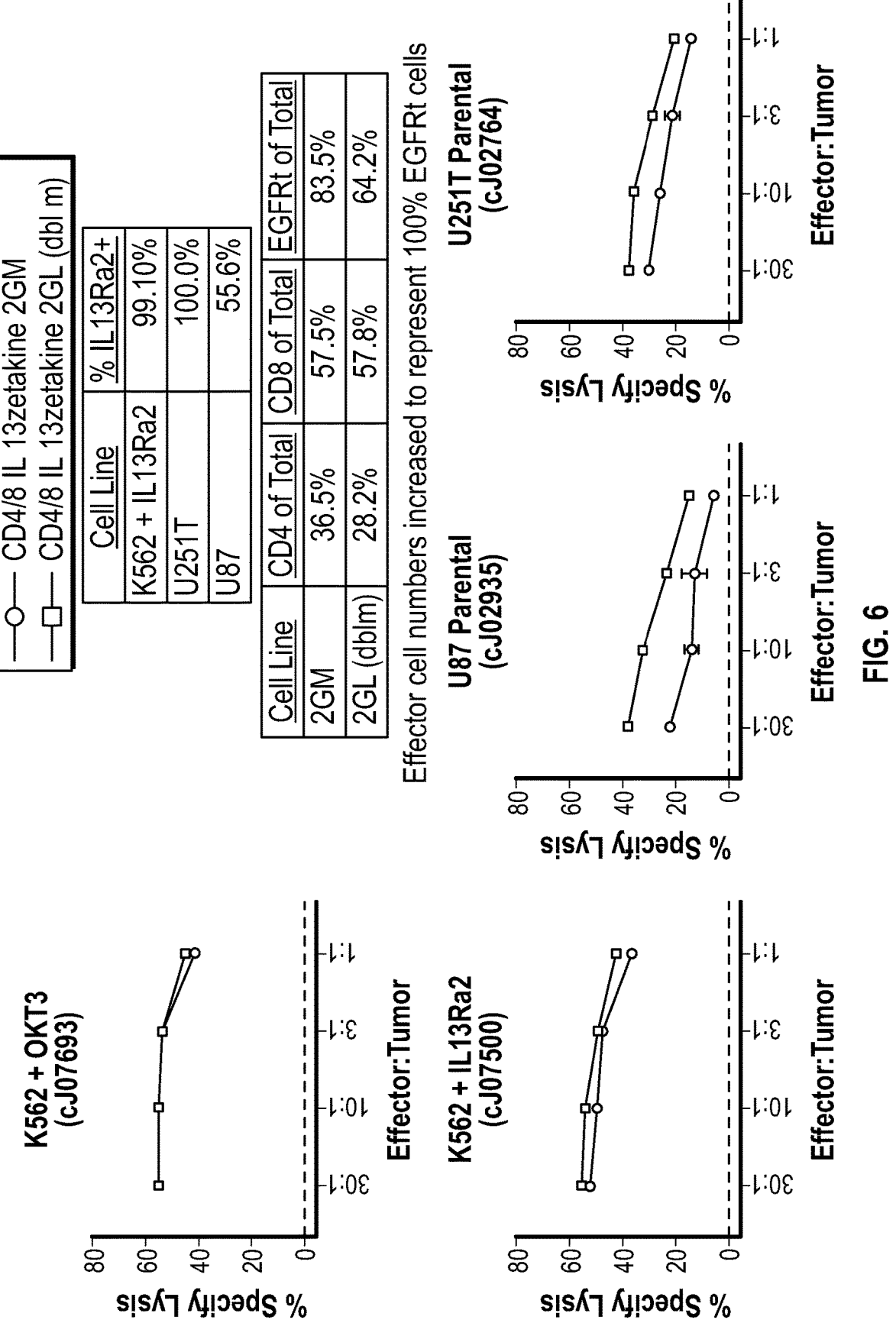

FIG. 6 depicts an analysis for specific lysis of target cells in the presence of effector CD4+/CD8+ T cells containing CARs with either the M or L spacer, at the indicated ratios.

Figure 7:
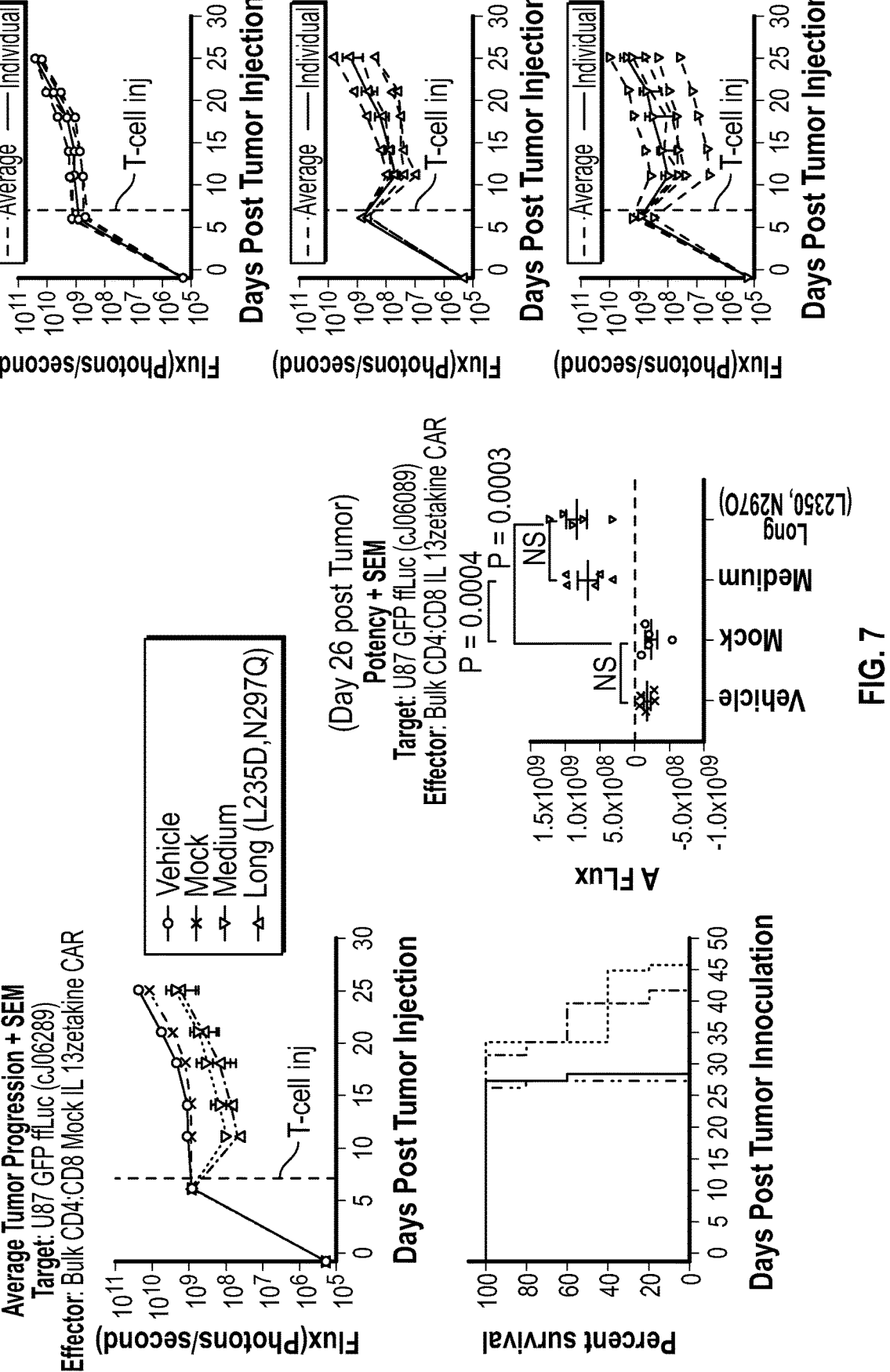

FIG. 7 depicts an analysis for tumor progression in mice as measured by flux, for mice treated with cells containing an IL13-zetakine CAR with either an M spacer or L spacer.

Figure 8:
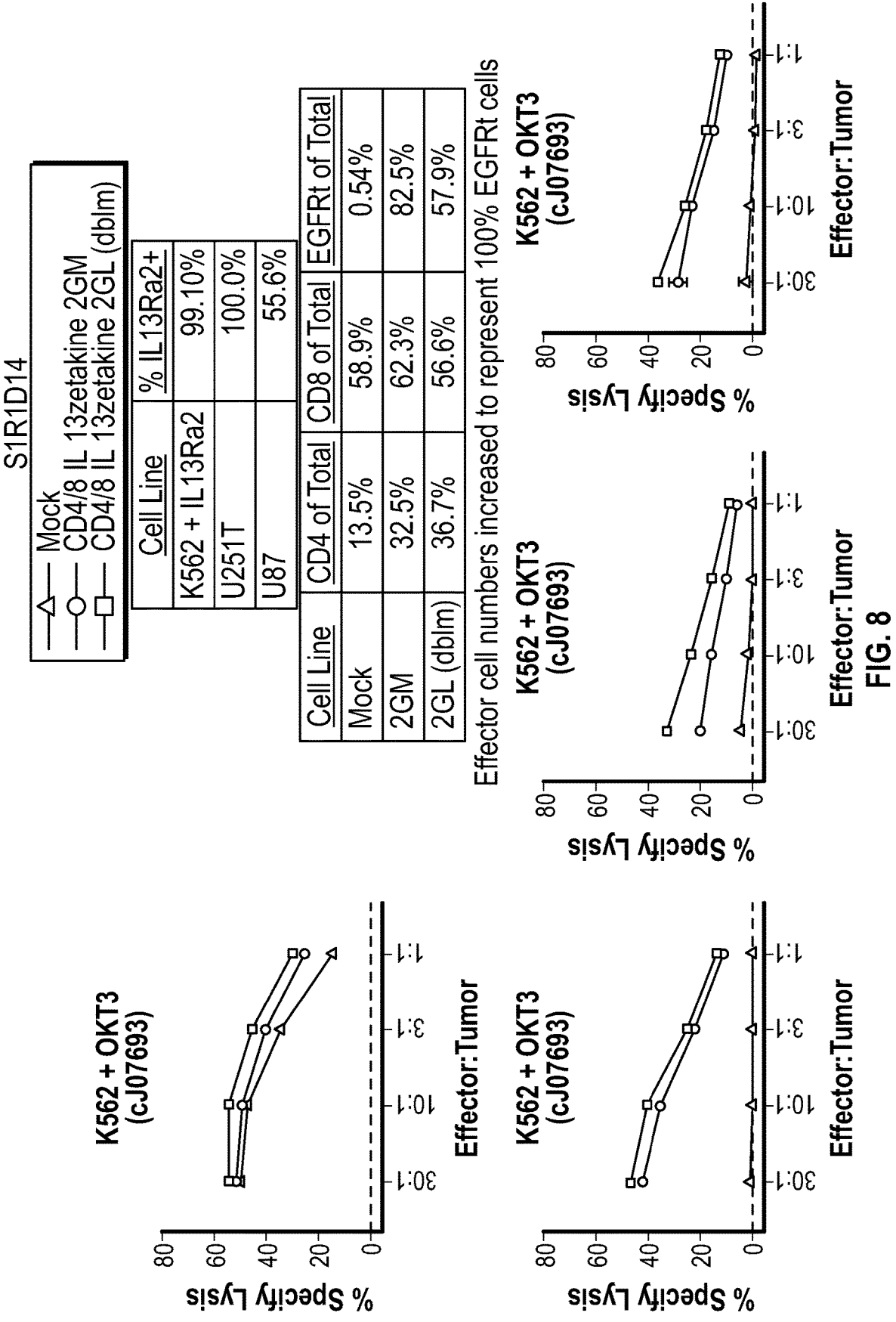

FIG. 8 depicts an analysis for specific lysis of target cells in the presence of effector CD4+/CD8+ T cells containing CARs with either the M, or L spacer, at the indicated ratios.

Figure 9:
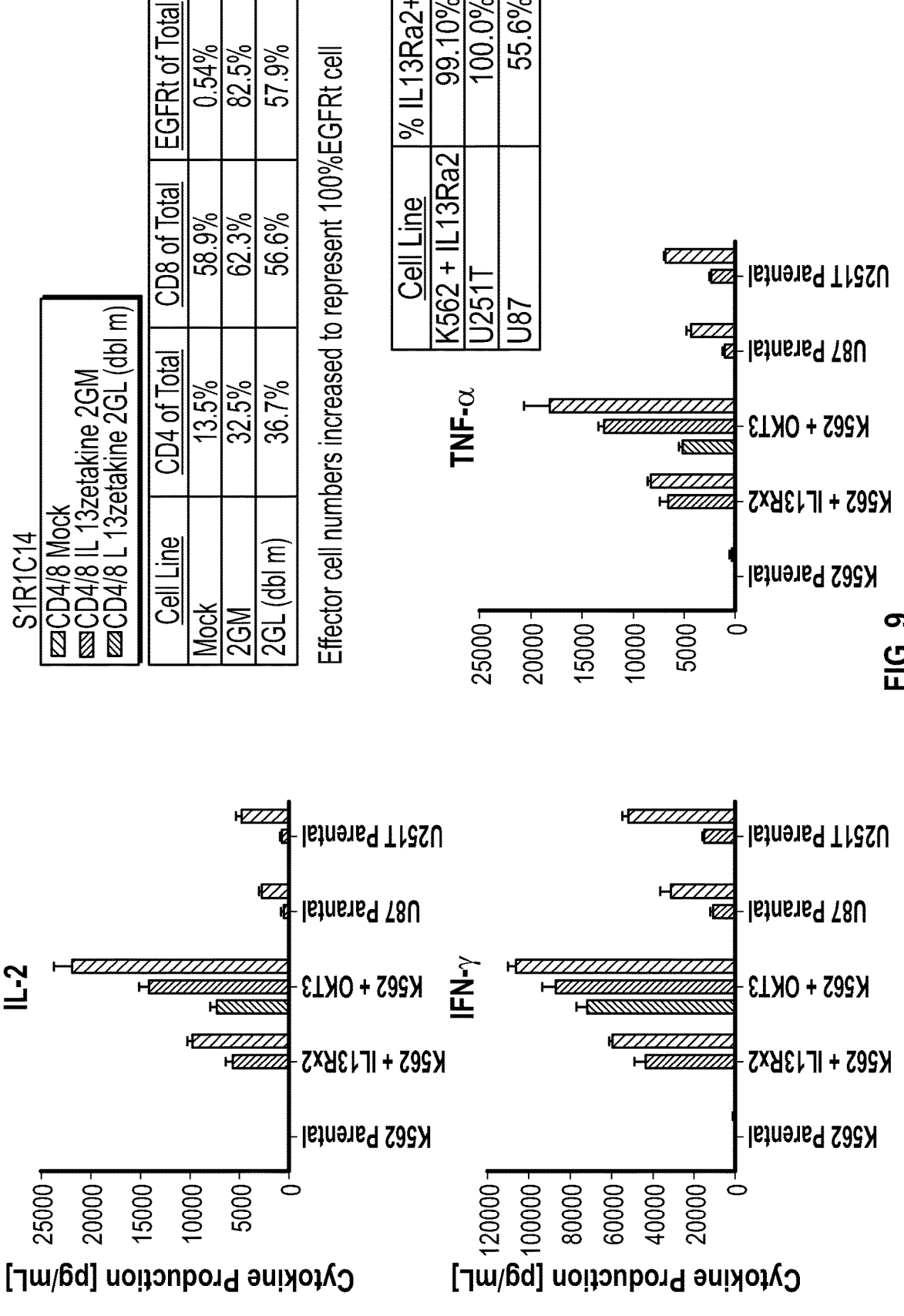

FIG. 9 depicts a cytokine release assay analysis for CD4+/CD8+ T cells containing IL13-zetakine CARs with either the M or L spacer.

DETAILED DESCRIPTION

Some embodiments of the methods and compositions provided herein relate to IL13-zetakine chimeric antigen receptors (CARs) capable of or configured to specifically binding to an interleukin-13 receptor subunit alpha-2 (IL-13Rα2). Some embodiments include nucleic acids encoding such CARs, host cells containing such CARs, and therapeutic methods, which utilize the host cells having these CARs e.g., by providing these cells to subjects in need as a medicament, for instance to treat or inhibit interleukin-13 receptor subunit alpha-2 (IL-13Rα2)-mediated disease or conditions, such as a cancer, for instance IL-13Rα2-positive malignancies including a gliomas and glioblastomas.

IL-13Rα2 was previously found to be abundant in metastatic or late-stage BLBC (Papageorgis et al. Breast Cancer Research, 2015; 17 (1); herein expressly incorporated by reference in its entirety). Based on publicly available data, correlations were made between, likelihood of progression-free survival based and high levels of IL-13Rα2. A subtype of BLBC that tended to spread to the lungs quickly was observed to have high IL-13Rα2 levels. IL-13Rα2 was also found to stimulate human glioma cell growth and metastasis through the Src/PI3K/Akt/mTOR signaling pathway. (Tu et al. Tumour Biol. 2016 November; 37 (11): 14701-14709; herein expressly incorporated by reference in its entirety). IL13Ra2 targeted therapies, such as chimeric receptor-based therapies, have been described (see, e.g., Brown et al Clin Cancer Res 2015; Brown et al N Engl J Med 2016; Brown et al Mol Ther 2017; WO 2014072888-A1, describing anti-IL-13 receptor alpha 2 (IL-13-Ra2) antibodies and antibody-drug conjugates for the treatment of cancer, each herein expressly incorporated by reference in their entirety). Among such therapies are those based on or including mutant IL13 (e.g., E13Y)-based binding or antigen recognition domains, such as zetakines. A desirable target for adaptive T-cell therapy is interleukin-13 receptor alpha chain variant 2 (IL-13Rα2). Specifically, in glioblastoma multiforme (GBM), IL-13Rα2 expression is a prognostic marker for patient survival and is associated with the promotion of tumor progression.

While IL-13Ra2 is expressed on >80% of high grade gliomas, including glioblastoma multiforme, tumors have been shown to evade targeted therapy by the loss of target epitope or general target expression. Accordingly, in some alternatives, to overcome this limitation multitargeted therapeutics are used for the treatment or inhibition of glioma. The combinatorial use of the IL-13-zetakine with other target therapies, such as chimeric antigen receptors, is believed to overcome tumor escape caused by target epitope loss. The alternatives provided herein have been tested in vitro and in a xenograft orthotopic tumor model. In some embodiments, therapies such as IL-13-zetakine directed immunotherapy, will be useful as is or as part of a curative approach for glioblastoma and other IL-13Ra2-positive malignancies or for certain subjects having the same.

Some embodiments provided herein include chimeric receptors, such as zetakines. In some embodiments, a zetakine includes a ligand binding domain, a spacer region, a transmembrane domain and an intracellular signaling region, typically including primary and costimulatory signaling domains. Some embodiments provided herein include second generation IL-13-zetakines such as those that include certain selected or configured spacer regions. In some aspects, zetakines provided herein include those that are capable of exhibiting or configured to exhibit improved therapeutic efficacy or in vivo anti-tumor effects or responses. Some embodiments provided herein are based in some repects on observations described herein, demonstrating that certain zetakines were able to elicit higher levels of cytokine production in response to target antigen, relative to reference chimeric receptors, which were otherwise the same or identical thereto, but differing in the spacer regions selected. Some embodiments provided herein are based in some respects on observations described herein, demonstrating the ability of certain zetakines to control tumor growth for an extended period and significantly increase median survival, such as in an orthotopic xenograft tumor model.

Definitions

As used herein, "nucleic acid" or "nucleic acid molecule" have their plain and ordinary meaning when read in light of the specification, and may include but is not limited to, for example, polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties or in pyrimidine or purine base moieties. Sugar modifications include, for example, replacement of one or more hydroxyl groups with halogens, alkyl groups, amines, or azido groups, or sugars can be functionalized as ethers or esters. Moreover, the entire sugar moiety can be replaced with sterically and electronically similar structures, such as aza-sugars or carbocyclic sugar analogs. Examples of modifications in a base moiety include alkylated purines or pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives, a nucleic acid sequence encoding a protein is provided. In some alternatives, the nucleic acid is RNA or DNA.

As used herein, "vector," "expression vector" or "construct" has its plain and ordinary meaning when read in light of the specification, and may include but is not limited to, for example, a nucleic acid used to introduce heterologous nucleic acids into a cell that has regulatory elements to provide expression of the heterologous nucleic acids in the cell. Vectors include but are not limited to plasmid, mini-circles, yeast, or viral genomes. In some alternatives, the vectors are plasmid, minicircles, or viral genomes. In some alternatives, the vector is a viral vector. In some alternatives, the viral vector is a lentivirus. In some alternatives, the vector is a lentiviral vector. In some alternatives, the vector is a foamy viral vector, adenoviral vectors, retroviral vectors or lentiviral vectors.

In some embodiments, the vectors and sequences provided are modified or optimized, such as by codon optimization, which may include the design process of altering codons to codons known to increase maximum protein expression efficiency in a desired cell, preferably in a human cell. In some alternatives, codon optimization is described, wherein codon optimization can be performed by using algorithms that are known to those skilled in the art to create synthetic genetic transcripts optimized for high protein yield. Programs containing algorithms for codon optimization are known to those skilled in the art. Programs can include, for example, OptimumGene™, or GeneGPS® algorithms, etc. Additionally synthetic codon optimized sequences can be obtained commercially for example from Integrated DNA Technologies and other commercially available DNA sequencing services. In some alternatives, the nucleic acids are described, wherein the genes of the nucleic acid for the complete gene transcript are codon optimized for expression in humans. In some alternatives, the genes are optimized to have selected codons specifically for maximal protein expression in human cells, which can increase the concentration of proteins or CARs of a T cell.

Codon optimization can be performed to reduce the occurrence of secondary structure in a polynucleotide, as well. In some alternatives, codon optimization can also be performed to reduce the total GC/AT ratio. Strict codon optimization can also lead to unwanted secondary structure or an undesirable GC content that leads to secondary structure. As such the secondary structures affect transcriptional efficiency. Programs such as GeneOptimizer can be used after codon usage optimization, for secondary structure avoidance and GC content optimization. These additional programs can be used for further optimization and trouble-shooting after an initial codon optimization to limit secondary structures that may occur after the first round of optimization. Alternative programs for optimization are known to those skilled in the art. In some alternatives, the nucleic acid comprises sequences that are codon optimized for expression in humans and/or to remove secondary structure and/or to reduce the total GC/AT ratio. In some alternatives, the sequences are optimized for secondary structure avoidance. In some alternatives, the sequences are optimized to reduce the total GC/AT ratio.

Some embodiments include polypeptide sequences or conservative variations thereof, such as conservative substitutions in a polypeptide sequence. In some embodiments, "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in TABLE 1.

TABLE 1

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

As used herein, "chimeric antigen receptor" has its plain and ordinary meaning when read in light of the specification, and may include but is not limited to, for example, a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). These receptors can be used to graft the specificity of a monoclonal antibody or binding fragment thereof onto a T cell with transfer of their coding sequence facilitated by viral vectors, such as a retroviral vector or a lentiviral vector. CARs are genetically engineered T cell receptors designed to redirect T cells to target cells that express specific cell-surface antigens. T cells can be removed from a subject and modified so that they can express receptors that can be specific for an antigen by a process called adoptive cell transfer. The T cells are reintroduced into the patient where they can then recognize and target an antigen. These CARs are engineered receptors that can graft an arbitrary specificity onto an immune receptor cell. The term chimeric antigen receptors or "CARs" are also considered by some investigators to include the antibody or antibody fragment, the spacer, signaling domain, and transmembrane region. Due to the surprising effects of modifying the different components or domains of the CARs described herein, such as the epitope binding region (for example, antibody fragment, scFv, or portion thereof), spacer, transmembrane domain, or signaling domain), the components of the CARs are frequently distinguished throughout this disclosure in terms of independent elements. The variation of the different elements of the CARs can, for example, lead to stronger binding affinity for a specific epitope or antigen.

The CARs graft the specificity of a monoclonal antibody or binding fragment thereof or scFv onto a T cell, with the transfer of their coding sequence facilitated by vectors. In order to use CARs as a therapy for a subject in need, a technique called adoptive cell transfer is used in which T cells are removed from a subject and modified so that they can express the CARs that are specific for an antigen. The T cells, which can then recognize and target an antigen, are reintroduced into the patient.

As used herein, "ligand" has its plain and ordinary meaning when read in light of the specification, and may include but is not limited to, for example, a substance that can form a complex with a biomolecule. By way of example and not of limitation, ligands can include substrates, proteins, small molecules, inhibitors, activators, nucleic acids or neu-rotransmitters. Binding can occur through intermolecular forces, for example ionic bonds, hydrogen bonds, or van der walls interactions. Ligand binding to a receptor protein can alter the three dimensional structure and determine its func-tional state. The strength of binding of a ligand is referred to as the binding affinity and can be determined by direct interactions and solvent effects. A ligand can be bound by a "ligand binding domain." A ligand binding domain, for example, can refer to a conserved sequence in a structure that can bind a specific ligand or a specific epitope on a protein. The ligand binding domain or ligand binding por-tion can comprise an antibody or binding fragment thereof or scFv, a receptor ligand or mutants thereof, peptide, and/or polypeptide affinity molecule or binding partner. Without being limiting, a ligand binding domain can be a specific protein domain or an epitope on a protein that is specific for a ligand or ligands.

As used herein, a "single chain variable fragment" or scFv has its plain and ordinary meaning when read in light of the specification, and may include but is not limited to, for example, a fusion protein that comprises the variable regions of the heavy chain (VH) and the light chains (VL) of an immunoglobulin, which are connected to one another with a short linker peptide. Without being limiting, the linker can comprise glycine for flexibility and hydrophilic amino acids, for example serine or threonine for solubility. The linker can connect the N-terminus of the VH with the C-terminus of the VL or it can connect the C-terminus of the VH with the N-terminus of the VL. In some alternatives, the ligand binding domain present on a CAR is a single chain variable fragment (scFv). In some alternatives, the scFv domain present on a CAR is specific for a IL-13 alpha 2 (IL13Rα2) receptor present on a tumor cell.

In some alternatives, the extracellular domain comprises at least one peptide spacer. In some alternatives, the peptide spacer is 15 amino acids or less but not less than 1 or 2 amino acids. In some embodiments, the spacer is a poly-peptide chain. In some aspects, the polypeptide chain may range in length, such as from a length of 3, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. A spacer can com-prise any 20 amino acids, for example, in any order to create a desirable length of polypeptide chain in a chimeric recep-tor, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine or tryptophan. In some alternatives, the spacer resides between the scFv or ligand binding domain and the transmembrane region of the chimeric receptor. A spacer may also be customized, selected, configured for, or optimized for a desired length so as to improve binding of scFv domain or ligand binding domain to the target cell, which may increase cytotoxic efficacy. In some alternatives, the linker or spacer between the scFv domain or ligand binding domain and the transmembrane can be 25 to 55 amino acids in length (e.g., at least, equal to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids or a length within a range defined by any two of the aforementioned lengths). Example spacers include IgG4 hinge alone, IgG4 hinge linked to CH2 and CH3 domains, or IgG4 hinge linked to the CH3 domain. Example spacers include those described in Hudecek et al. (lin. Cancer Res., 19:3153 (2013), international patent appli-cation publication number WO2014031687, U.S. Pat. No. 8,822,647 or published app. No. US2014/0271635 hereby expressly incorporated by reference in their entireties.

In some embodiments, a signaling domain of a CAR, such as primary signaling domain or costimulatory domain, includes an intracellular or cytoplasmic domain of a protein or a receptor protein that interacts with components within the interior of the cells and is capable of relaying or participating in relaying a signal. Such interactions in some aspects can occur through the intracellular domain commu-nicating via specific protein-protein or protein-ligand inter-actions with an effector molecule or an effector protein, which in turn can send the signal along a signal chain to its destination. In some embodiments, the signaling domain includes a co-stimulatory domain. In some aspects, the costimulatory domain includes a signaling moiety that pro-vides to T cells a signal, which in addition to the primary signal provided by for instance the CD3 zeta chain of the TCR/CD3 complex, enhances response such as a T-cell effector response, such as, for example, an immune response, activation, proliferation, differentiation, cytokine secretion, cytolytic activity, perforin or granzyme activity and the like. In some embodiments, the intracellular signal-ing domain and/or the co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, or B7-H3, or a ligand that specifically binds with CD83.

In some embodiments, the compositions, cells and vectors include marker sequences or nucleic acids encoding the same, which may include, for example, a protein that serves as a label for a cell. In some alternatives of the cells described herein, the cells co-express a marker protein for a specific chimeric protein that is expressed. In some alterna-tives of the cells provided herein, the chimeric receptor is co-expressed with a specific marker protein. In some alter-natives of the cells provided herein, the cells comprise a nucleic acid encoding a chimeric receptor. Markers may include a selectable marker sequence, such as a gene intro-duced into a vector or a cell that confers a trait for artificial selection. A selectable marker sequence or marker sequence can be a screenable marker to allow a researcher to distin-guish between wanted and unwanted cells, or to enrich for a specific cell type. In some alternatives, a vector is provided wherein the vector encodes a chimeric receptor comprising a marker sequence, wherein said marker sequence encodes a cell surface selectable marker. In the alternatives described herein, the CARs provided can comprise a marker sequence that can be selected in experiments, such as flow cytometry. In some alternatives, the marker is the protein Her2tG or EGFRt.

As used herein, "methotrexate" (MTX), has its plain and ordinary meaning when read in light of the specification, and may include but is not limited to, for example, an antimetabolite and antifolate drug. It acts by inhibiting the metabolism of folic acid. In some alternatives, a method of generating engineered multiplexed T-cells for adoptive T-cell immunotherapy is provided. In the broadest sense, the method can comprise providing the gene delivery polynucleotide of any of the alternatives described herein, selecting the cells comprising the gene delivery polynucleotide, wherein the selecting comprises adding a selection reagent. In some alternatives described herein, the selection reagent comprises an agent for selection. In some alternatives, the selection reagent is MTX.

As used herein, "dihydrofolate reductase", or DHFR, as described herein, has its plain and ordinary meaning when read in light of the specification, and may include but is not limited to, for example, an enzyme that reduces dihydrofolic acid to tetrahydrofolic acid, using NADPH as electron donor, which can be converted to the kinds of tetrahydrofolate cofactors used in 1-carbon transfer chemistry. In some alternatives described herein, a gene delivery polynucleotide is provided. In some alternatives, the gene delivery polynucleotide comprises at least one selectable marker cassette encoding for a double mutant of dihydrofolate reductase (DHFRdm).

As used herein, a "ribosome skip sequence" as described herein refers to a sequence that during translation, forces the ribosome to "skip" the ribosome skip sequence and translate the region after the ribosome skip sequence without formation of a peptide bond. Several viruses, for example, have ribosome skip sequences that allow sequential translation of several proteins on a single nucleic acid without having the proteins linked via a peptide bond. As described herein, this is the "linker" sequence. In some alternatives of the nucleic acids provided herein, the nucleic acids comprise a ribosome skip sequence between the sequence for the chimeric receptor and the sequence of the marker protein, such that the proteins are co-expressed and not linked by a peptide bond. In some alternatives, the ribosome skip sequence is a P2A, T2A, E2A or F2A sequence. In some alternatives, the ribosome skip sequence is a T2A sequence.

As used herein, a "zetakine" can refer to a certain type of CAR in which a ligand binding domain includes a cytokine, which can specifically bind to a cytokine receptor. In some embodiments, the cytokine can include a human cytoke, such as IL-13. In some embodiments, the IL-13 includes a mutation in the sequence, and has a high affinity for IL-13 receptor α2.

As used herein, "mutein" has its plain and ordinary meaning when read in light of the specification, and may include but is not limited to, for example, a protein arising as a result of a mutation. "IL-13 mutein" may be a IL-13 mutant that may have at least one or at least two amino acid substitutions.

As used herein, "interleukin-13 receptor subunit alpha-2 (IL-13Rα2)", also known as CD213A2 (cluster of differentiation 213A2), has its plain and ordinary meaning when read in light of the specification, and may include but is not limited to, for example, a membrane bound protein that in humans is encoded by the IL-13RA2 gene. IL-13Rα2 is closely related to IL-13Rα1, a subunit of the interleukin-13 receptor complex. IL-13Rα2 generally binds IL-13 with high affinity, but lacks any significant cytoplasmic domain and does not appear to function as a signal mediator. It is, however able to regulate the effects of both IL-13 and IL-4, despite the fact it is unable to bind directly to the latter. It is also reported to play a role in the internalization of IL-13.

As used herein, "T cells" or T lymphocytes in some embodiments may include T cells from any mammalian, preferably primate, species, including monkeys, dogs, or humans. In some alternatives the T cells are allogeneic (from the same species but different donor) as the recipient subject who receives or is to receive the cells, such as in the form of a therapeutic composition; in some alternatives the T cells are autologous (the donor and the recipient are the same); in some alternatives the T cells are syngeneic (the donor and the recipients are different but are identical twins).

As used herein, "cytotoxic T lymphocyte" (CTL), has its plain and ordinary meaning when read in light of the specification, and may include but is not limited to, for example, a T lymphocyte that expresses CD8 on the surface thereof (e.g., a CD8+ T-cell). In some alternatives, such cells are preferably "memory" T cells ($T_M$ cells) that are antigen-experienced. In some alternatives, the cell is a cytotoxic T lymphocyte. "Central memory" T cell (or "$T_{CM}$") as used herein, refers to an antigen experienced CTL that expresses CD62L, CCR-7 and/or CD45RO on the surface thereof, and does not express or has decreased expression of CD45RA, as compared to naive cells. In some alternatives, the cell is a central memory T cell ($T_{CM}$). In some alternatives, the central memory cells are positive for expression of CD62L, CCR7, CD28, CD127, CD45RO, or CD95 or an combination thereof, and may have decreased expression of CD54RA, as compared to naïve cells. "Effector memory" T cell (or "TEM") as used herein refers to an antigen experienced T cell that does not express or has decreased expression of CD62L on the surface thereof, as compared to central memory cells, and does not express or has a decreased expression of CD45RA, as compared to naïve cell. In some alternatives, the cell is an effector memory T cell. In some alternatives, effector memory cells are negative for expression of CD62L and/or CCR7, as compared to naïve cells or central memory cells, and may have variable expression of CD28 and/or CD45RA.

Mature T cells express the surface protein CD4 and are referred to as CD4+ T cells. CD4+ T cells are generally treated as having a pre-defined role as helper T cells within the immune system. For example, when an antigen-presenting cell expresses an antigen on MHC class II, a CD4+ cell will aid those cells through a combination of cell to cell interactions (e.g. CD40 and CD40L) and through cytokines. Nevertheless, there are rare exceptions; for example, subgroups of regulatory T cells, natural killer cells, or cytotoxic T cells express CD4. All of the latter CD4+ expressing T cell groups are not considered T helper cells.

As used herein, "central memory" T cell (or "$T_{CM}$") has its plain and ordinary meaning when read in light of the specification, and may include but is not limited to, for example, an antigen experienced CTL that expresses CD62L or CCR-7 or CD45RO or any combination thereof on the surface thereof, and does not express or has decreased expression of CD45RA as compared to naïve cells. In some alternatives, central memory cells are positive for expression of CD62L, CCR7, CD28, CD127, CD45RO, or CD95 or any combination thereof, and have decreased expression of CD54RA as compared to naïve cells.

As used herein, "effector memory" T-cell (or "TEM") has its plain and ordinary meaning when read in light of the specification, and may include but is not limited to, for example, an antigen experienced T cell that does not express or has decreased expression of CD62L on the surface thereof as compared to central memory cells, and does not express or has decreased expression of CD45RA as compared to naïve cell. In some alternatives, effector memory cells are negative for expression of CD62L or CCR7 or both, as compared to naïve cells or central memory cells, and have variable expression of CD28 or CD45RA or both.

As used herein, "naïve" T cells has its plain and ordinary meaning when read in light of the specification, and may include but is not limited to, for example, a non-antigen experienced T lymphocyte that expresses CD62L or CD45RA or both, or does not express CD45RO− as compared to central or effector memory cells. In some alternatives, naïve CD8+T lymphocytes are characterized by the expression of phenotypic markers of naïve T-cells including CD62L, CCR7, CD28, CD127, or CD45RA or any combination thereof.

As used herein, "effector" "TE" T cells has its plain and ordinary meaning when read in light of the specification, and may include but is not limited to, for example, antigen experienced cytotoxic T lymphocyte cells that do not express or have decreased expression of CD62L, CCR7, or CD28, or are positive for granzyme B or perforin or any combination thereof, as compared to central memory or naïve T cells.

As used herein, "T cell precursors" has its plain and ordinary meaning when read in light of the specification, and may include but is not limited to, for example, lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4$^-$CD8$^-$) cells. As they progress through their development, they become double-positive thymocytes (CD4$^-$CD8$^-$), and finally mature to single-positive (CD4$^-$CD8$^-$ or CD4$^-$CD8$^-$) thymocytes that are then released from the thymus to peripheral tissues.

As used herein, "pharmaceutical excipient," or pharmaceutical vehicle has its plain and ordinary meaning when read in light of the specification, and may include but is not limited to, for example, a carrier or inert medium used as a solvent in which the medicinally active agent or T cells for treatment or therapy is formulated and/or administered. Vehicles can include polymeric micelles, liposomes, lipoprotein-based carriers, nano-particle carriers, or dendrimers, or other vehicles for T cells that are known to one skilled in the art. An ideal vehicle or excipient can be non-toxic, biocompatible, non-immunogenic, biodegradable, or can avoid recognition by the host's defense mechanisms or any combination thereof.

As used herein, "subject" or "patient," as described herein, refers to any organism upon which the alternatives described herein may be used or administered, e.g., for experimental, diagnostic, prophylactic, and/or therapeutic purposes. Subjects or patients include, for example, animals. In some alternatives, the subject is mice, rats, rabbits, non-human primates, or humans. In some alternatives, the subject is a cow, sheep, pig, horse, dog, cat, primate or a human.

High levels of Interleukin 13 receptor alpha 2 (IL-13RA2) are found on a number of cancer cells including pancreatic, breast, and ovarian cancers or malignant gliomas, such as glioblastoma. IL-13RA2 also can be over-expressed in a vast majority of human patients with high-grade astrocytomas (see PLOS One. 2013 Oct. 16; 8 (10):e77719; herein expressly incorporated by reference in its entirety). Additionally, reducing the amount of IL13RA2 expression in cancer cells can significantly slow tumor growth in models (Breast Cancer Research, 2015; 17 (1); herein expressly incorporated by reference in its entirety). It is contemplated that few types of normal tissues express IL-13-RA2 and, in such cases, only at low levels. In the case of the glioblastoma multiforme (GBM), the high expression of IL13Rα2 can be a prognostic marker of tumor progression and poor patient survival.

Some embodiments provided herein include chimeric receptors, such as zetakines, including those directed against solid tumors. In some embodiments, the extracellular domain comprises a binding domain containing a mutant form of IL13 (such as IL13 E13Y), linked to the transmembrane domain of the receptor via a spacer region. In some embodiments, the spacer region generally extends from the binding domain to the transmembrane domain. In some embodiments, the spacer comprises a polypeptide that is greater than or greater than about, or comprises at least at or about, 12, 15, 20, 30, 40, 50, 60, 70, 80, 90, or 100 amino acids in length, such as greater than 50 or 100 amino acids in length, and optionally less than 150, 200, or 220 amino acids in length, such as between 50 and 220 amino acids in length, between 50 and 150 amino acids in length, or at or about 110 amino acids in length. In some embodiments, the transmembrane domain is or comprises a CD28 transdomain (CD28tm), followed by a costimulatory domain(s), such as a costimulatory domain derived from an intracellular segment of human 4-1BB (CD137), and a primary signaling domain such as a signaling domain of CD3-zeta (CD32).

In some embodiments, a nucleic acid encoding the chimeric receptor further includes a sequence encoding a marker, optionally operably linked to the same promoter to which the nucleic acid encoding the receptor is linked. In some aspects, the marker is a truncated version of a cell surface receptor such as a truncated version of the epidermal growth factor receptor (EGFRt), CD19 (CD19t), or HER2 (Her2t) or other receptor. In some aspects, the nucleic acid encoding the marker is separated from that encoding the chimeric receptor by a skip sequence such as a P2A or T2A ribosomal skip sequence, or an IRES. In some aspects, the nucleic acid further includes a dihydrofolate reductase double mutant (DHFRdm) transgene, such as may be added to facilitate methotrexate selection of cells expressing products of the construct, such as in therapeutic T-cell products.

Certain Nucleic Acids

Some embodiments of the methods and compositions provided herein include nucleic acids encoding a membrane-tethered IL-13 mutein-directed zetakine receptor. In some embodiments, a nucleic acid comprises: a) a first polynucleotide encoding an extracellular domain; b) a second polynucleotide encoding a mutein of IL13; c) a third polynucleotide encoding a transmembrane domain; and d) a fourth polynucleotide encoding an intracellular signaling domain. In some embodiments, the nucleic acid further comprises a polynucleotide encoding a marker polypeptide, such as EGFRt. In some embodiments, the nucleic acid further comprises a polynucleotide encoding a selectable marker, such as DHFRdm. In some embodiments the nucleic acid includes a ribosome skip sequence.

In some embodiments, the mutein of IL13 comprises, consists of, or consists essentially of an amino acid sequence having a percentage identity with the amino acid sequence of SEQ ID NO:16. In some such embodiments, the sequence identity to SEQ ID NO: 16 is at least 80%, 85%, 90%, 91%, 92%, 93%, 94%, 95%, 96%, 97%, 98%, 99%, 100%, or a percentage between any two of the foregoing percentages. In some embodiments, the mutein of IL13 comprises, consists of, or consists essentially of the amino acid sequence of SEQ ID NO:16.

In some alternatives, the extracellular domain comprises at least one peptide spacer. In some alternatives, the peptide spacer is 15 amino acids or less but not less than 1 or 2 amino acids. In some embodiments, the spacer is a polypeptide chain. In some alternatives the spacer comprises an IgG4 hinge or portion thereof. In some alternatives, the spacer comprises a hinge region of a human antibody or portion thereof. In some alternatives of the method, the spacer comprises an IgG4 hinge or portion thereof. In some alternatives, the IgG4 hinge region is a modified IgG4 hinge or portion thereof. A "modified IgG4 hinge" as described herein can refer to a hinge region that can have at least 90%, 91%, 92%, 93%, 94%, 95%, 96%, 97%, 98%, 99%, or 100% sequence identity or a sequence identity within a range defined by any two of the aforementioned percentages, with a hinge region of an amino acid sequence as set forth in SEQ ID NO:01, SEQ ID NO:02, SEQ ID NO:03, SEQ ID NO:04, SEQ ID NO: 05, SEQ ID NO:06, SEQ ID NO:07, or SEQ ID NO:08. In some alternatives, the spacer is an S spacer, M spacer or an L spacer. The S spacer comprises a sequence set forth in SEQ ID NO: 09. The M spacer comprises a sequence set forth in SEQ ID NO: 10. The L spacer comprises a sequence set forth in SEQ ID NO: 11.

In some alternatives, the spacer comprises, consists of or consists essentially of an IgG4-hinge spacer(S), an IgG4 hinge-CH3 spacer (M), or an IgG4 hinge-CH2-CH3 spacer. In some alternatives, the spacer comprises an IgG4-CH3 spacer (M).

In some embodiments, the spacer comprises, consists of, or consists essentially of an amino acid sequence having a percentage sequence identity to the amino acid sequence of SEQ ID NO:10. In some such embodiments, the sequence identity to SEQ ID NO: 10 is at least 80%, 85%, 90%, 91%, 92%, 93%, 94%, 95%, 96%, 97%, 98%, 99%, or 100%, or a percentage between any two of the foregoing percentages. In some embodiments, the spacer comprises, consists of, or consists essentially of the amino acid sequence of SEQ ID NO: 10.

In some embodiments, the spacer comprises, consists of, or consists essentially of an amino acid sequence having a sequence percentage identity to the amino acid sequence of SEQ ID NO:11. In some such embodiments, the sequence identity to SEQ ID NO: 11 is at least 80%, 85%, 90%, 91%, 92%, 93%, 94%, 95%, 96%, 97%, 98%, 99%, or 100%, or a percentage between any two of the foregoing percentages. In some embodiments, the spacer comprises, consists of, or consists essentially of the amino acid sequence of SEQ ID NO: 11.

In some embodiments, the spacer has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, and including any integer between the endpoints of any of the listed ranges. In some embodiments, a spacer region has 12 amino acids or less but not zero, 119 amino acids or less but not zero, or 229 amino acids or less but not zero. In some embodiments, the spacer is less than 250 amino acids in length but not zero, less than 200 amino acids in length but not zero, less than 150 amino acids in length but not zero, less than 100 amino acids in length but not zero, less than 75 amino acids in length but not zero, less than 50 amino acids in length but not zero, less than 25 amino acids in length but not zero, less than 20 amino acids in length but not zero, less than 15 amino acids in length but not zero, less than 12 amino acids in length but not zero, or less than 10 amino acids in length but not zero. In some embodiments, the spacer is from or from 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (lin. Cancer Res., 19:3153 (2013), international patent application publication number WO2014031687, U.S. Pat. No. 8,822,647 or published app. No. US2014/0271635 hereby expressly incorporated by reference in their entireties.

In some embodiments, the transmembrane domain is a region of a membrane-spanning protein that is hydrophobic that can reside in the bilayer of a cell to anchor a protein that is embedded to the biological membrane. Without being limiting, the topology of the transmembrane domain can be a transmembrane alpha helix. In some alternatives, the transmembrane domain comprises a CD28 transmembrane sequence or a fragment thereof, such as one that is a length of 10, 11, 12, 13, 14, 15, 16, 17, 18, 19, 20, 21, 22, 23, 24, 25, 26, 27, or 28 amino acids or a length within a range defined by any two of the aforementioned lengths. In some alternatives, the CD28 transmembrane sequence or fragment thereof comprise 28 amino acids in length.

In some alternatives, the intracellular signaling domain comprises all or a portion of a CD3 zeta domain in combination with a co-stimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a signaling functional portion of a CD3 zeta domain and a co-stimulatory functional portion of a 4-1BB domain.

In some alternatives, the nucleic acid further comprises a sequence that encodes a marker sequence. In some aspects, the marker is a truncated version of a cell surface receptor such as a truncated version of the epidermal growth factor receptor (EGFRt), CD19 (CD19t), or HER2 (Her2t) or other receptor. In some alternatives, the marker sequence is a truncated form of a cell surface receptor, optionally EGFRt.

In some alternatives, the nucleic acid further comprises a dihydrofolate reductase transgene configured for methotrexate selection. In some alternatives, the dihydrofolate reductase transgene is a dihydrofolate reductase double mutant (DHFRdm). In some alternatives, the dihydrofolate reductase double mutant comprises amino acid mutations of L22F and F31S.

In some alternatives, the nucleic acid further comprises a sequence encoding a ribosomal skip sequence. In some alternatives, the ribosomal skip sequence comprises P2A or T2A.

In some alternatives, the nucleic acid is modified to reduce the total GC/AT ratio of the nucleic acid. In some alternatives, the nucleic acid is codon optimized for expression in humans.

Some embodiments of the methods and compositions provided herein include an expression vector comprising the nucleic acid of any one of the alternatives herein is provided. In some alternatives, the vector is a viral vector. In some alternatives, the vector is a lentiviral or adenoviral vector. In some alternatives, the zetakine receptor comprises: an extracellular domain comprising a mutein of IL-13 and a spacer; a transmembrane domain; and an intracellular signaling region, wherein the spacer is interposed between the mutein and transmembrane domain.

Certain Chimeric Receptors

Some embodiments of the methods and compositions provided herein include chimeric receptor polypeptides encoded by the nucleic acid of any of the alternatives herein or the vector of any one of the alternatives herein. Some embodiments of the methods and compositions provided herein include membrane-tethered, IL13 mutein-directed zetakine receptors encoded by the nucleic acid of any one of the alternatives herein or the vector of any one of the alternatives herein.

Certain Host Cells

Some embodiments of the methods and compositions provided herein include host cells comprising a nucleic acid of any one of the alternatives herein or an expression vector of any one of the alternatives herein. In some embodiments, the host cell comprises a genetically modified cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell and, wherein the central memory T cell is positive for CD45RO+, CD62L+, and CD8+. In some alternatives, the host cell is a CD4+T helper lymphocyte cell selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell and, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell.

Some embodiments of the methods and compositions provided herein include a host cell of any one of the alternatives herein or the composition of any one of the alternatives herein for use in the treatment or inhibition of a cancer or a solid tumor expressing an IL-13α2 receptor is provided. The composition comprises the host cell of any one of the alternatives herein and a pharmaceutical excipient. In some alternatives, the cancer is a glioblastoma tumor. In some alternatives, the cancer is glioblastoma multiforme (GBM). In some alternatives, the cancer is an IL13Rα-positive malignancy. In some alternatives, the cancer is brain cancer or brain tumors. Accordingly, some embodiments concern the host cell of any of the alternatives described herein for use in a medicament or for use in the treatment or inhibition of a cancer, such as a brain cancer including but not limited to an IL13Rα-positive malignancy, GBM, glioma, or glioblastoma.

Certain Compositions

Some embodiments of the methods and compositions provided herein include compositions comprising a host cell of any one of the alternatives herein, and a pharmaceutically acceptable excipient.

Certain Methods of Preparing Host Cells

Some embodiments of the methods and compositions provided herein include methods for preparing a host cell of any one of the alternatives herein. Some such embodiments include: a) introducing a nucleic acid of any one of the alternatives herein or an expression vector of any one of the alternatives herein into lymphocytes; b) culturing the lymphocytes in the presence of anti-CD3 or anti CD28 antibodies and at least one homeostatic cytokine; and c) selecting the lymphocytes with a selection reagent, wherein the selection reagent is configured to selectively enrich cells transduced with the nucleic acid or vector. In some alternatives, the selection reagent is methotrexate. In some alternatives, the lymphocytes have a CD45RA−, CD45RO+, or CD62L+ phenotype or any combination thereof. In some alternatives, the lymphocytes are CD8+ or CD4+. In some alternatives, the cytokine is IL-15, IL-7 or IL-21 or any combination thereof. In some alternatives, the method further comprises introducing a second nucleic acid into the host cell, the second nucleic acid encoding a marker protein. In some alternatives, the marker protein is EGFRt. In some alternatives, the expression vector comprises the nucleic acid of any one of the alternatives herein is provided. In some alternatives, the vector is a viral vector. In some alternatives, the vector is a lentiviral or adenoviral vector.

In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell and, wherein the central memory T cell is positive for CD45RO+, CD62L+, or CD8+ or any combination thereof. In some alternatives, the host cell is a CD4+T helper lymphocyte cell selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell and, wherein the naïve CD4+ T cell is positive for CD45RA+, CD62L+ or CD4+ or any combination thereof and negative for CD45RO. In some alternatives, the host cell is a precursor T cell. In some alternatives, the host cell is a hematopoietic stem cell.

Certain Methods of Therapy

Some embodiments of the methods and compositions provided herein include uses of a host cell provided herein in therapeutic methods. Some such embodiments include the use of a cell in the treatment, inhibition, or amelioration of a cancer or a solid tumor expressing an IL-13α2 (IL-13Rα2) receptor. In some alternatives, the cancer is a glioblastoma tumor. In some alternatives, the cancer is glioblastoma mutiforme (GBM). In some alternatives, the cancer is a IL-13Rα-positive malignancy. In some alternatives, the cancer is brain cancer or brain tumors.

Some embodiments of the methods and compositions provided herein include methods of performing cellular immunotherapy in a subject having a cancer or a tumor comprising: administering the host cell of anyone of the alternatives herein or the composition of the alternatives herein is provided to the subject. The composition comprises a host cell of any one of the alternatives herein, and a pharmaceutically acceptable excipient is provided. In some alternatives, the cancer is glioblastoma tumor. In some alternatives, the cancer is glioblastoma multiforme (GBM).

In some alternatives, the cancer is an IL13Rα-positive malignancy. In some alternatives, the cancer is brain cancer. In some alternatives, the subject is selected to receive combination therapy. In some alternatives, the combination therapy comprises administering a chemotherapeutic drug. In some alternatives, the combination therapy comprises administering radiation therapy. In some alternatives, the chemotherapeutic drug comprises electochemotherapy, alkylating agents, antimetabolites (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, or Thioguanine), anti-tumor antibiotics, topoisomerase inhibitors, mitotic inhibitors, corticosteroids, DNA intercalating agents, or checkpoint inhibitors (checkpoint kinases CHK1, or CHK2). In some alternatives, the cancer is a glioma.

EXAMPLES

Example 1—Construction of IL-13 (E13Y)-Zetakine CARs

Figure 1:
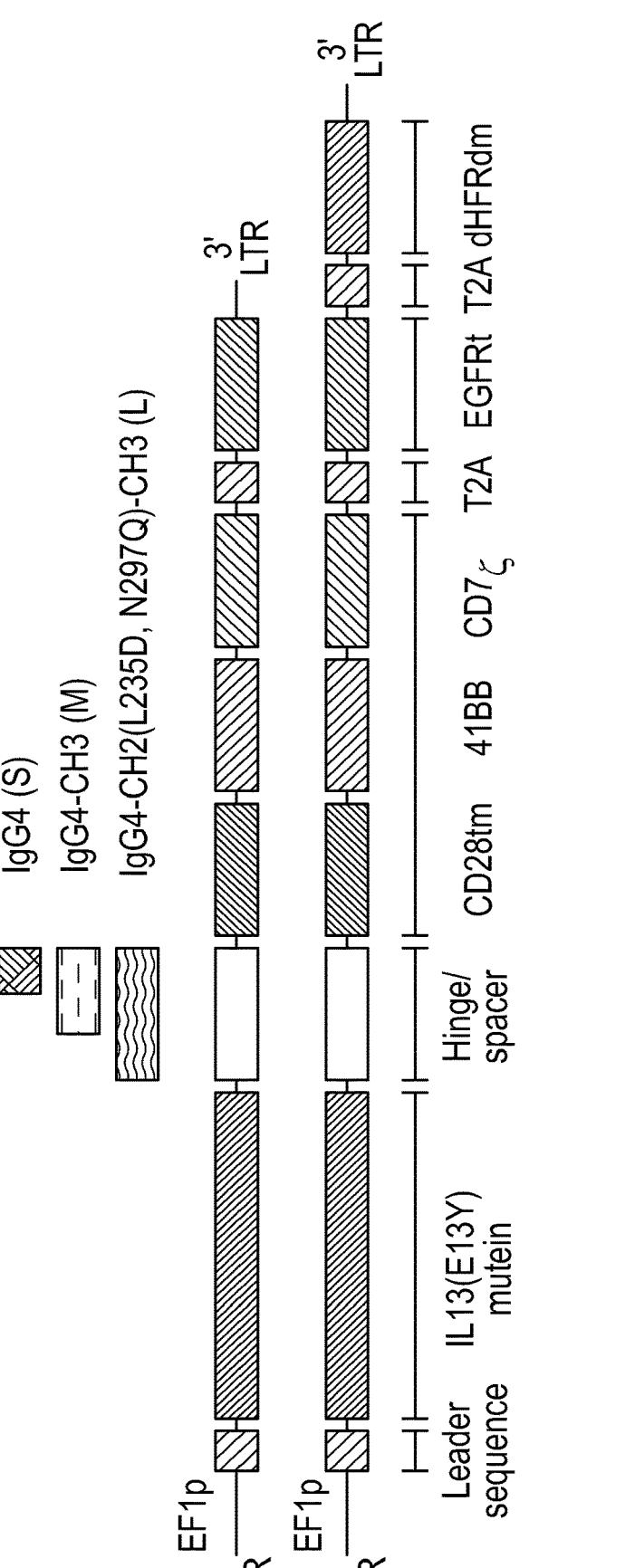
FIG. 1 depicts a schematic of nucleic acids encoding certain IL-13 (E13Y)-zetakine CARs with different spacer regions. The nucleic acids encoding the zetakine CARs included: a leader sequence (EFlp); a polynucleotide encoding an IL-13 (E13Y) mutein; a polynucleotide encoding one of three different spacers; a polynucleotide encoding a CD28tm transmembrane sequence; a polynucleotide encoding a signaling domain including a primary and costimulatory domain, which were a 4-1BB domain, a CD3 zeta domain, respectively. The spacers incuded: a short 'S' spacer, which included a modified IgG4hinge; a medium 'M' spacer, which included a modified IgG4hinge and an immunoglobulin CH3 region (IgG4 hinge-CH3); and a long 'L' spacer, which included a modified IgG4hinge, an immunoglobulin CH2 domain and an immunoglobulin CH3 domain (IgG4 hinge-CH2-CH3). The L spacer contained two mutations in the CH2 domain (L235D, N297Q). Self-cleavable ribosome skip sequence 2A peptide (T2A) were also included. In some constructs, the lentivector also included a dihydrofolate reductase double mutant transgene configured for methotrexate selection (DHFRdm).

Various IL-13 (E13Y)-zetakine CARs with different spacer regions were constructed. As shown in FIG. 1, the nucleic acids encoding the zetakine CARs included: a leader sequence (EF1p); a polynucleotide encoding an IL-13 (E13Y) mutein; a polynucleotide encoding one of three different spacers; a polynucleotide encoding a CD28tm transmembrane sequence; a polynucleotide encoding a signaling domain including a primary and costimulatory domain, which were a 4-1BB domain, a CD3 zeta domain, respectively. The spacers incuded: a short 'S' spacer, which included a modified IgG4hinge; a medium 'M' spacer, which included a modified IgG4hinge and an immunoglobulin CH3 region (IgG4 hinge-CH3); and a long 'L' spacer, which included a modified IgG4hinge, an immunoglobulin CH2 domain and an immunoglobulin CH3 domain (IgG4 hinge-CH2-CH3). The L spacer contained two mutations in the CH2 domain (L235D, N297Q), which can mitigate potential unwanted effects resulting from potential interactions of the receptor with Fc receptors (FcRs). Self-cleavable ribosome skip sequence 2A peptide (T2A) were also included. In some constructs, the lentivector also comprises a dihydrofolate reductase double mutant transgene configured for methotrexate selection (DHFRdm). SEQ ID NO:16 lists the IL-13 mutein. An example sequence of an IL-13 mutein can be found in Kahlon et al. (Kahlon K S et al., Cancer Res. 2004; included by reference in its entirety herein). As described herein, the E13Y mutation confered enhanced selective binding to IL-13Rα2.

Example 2—In Vitro Comparison of CARs Including Different Spacers

Figure 2A:
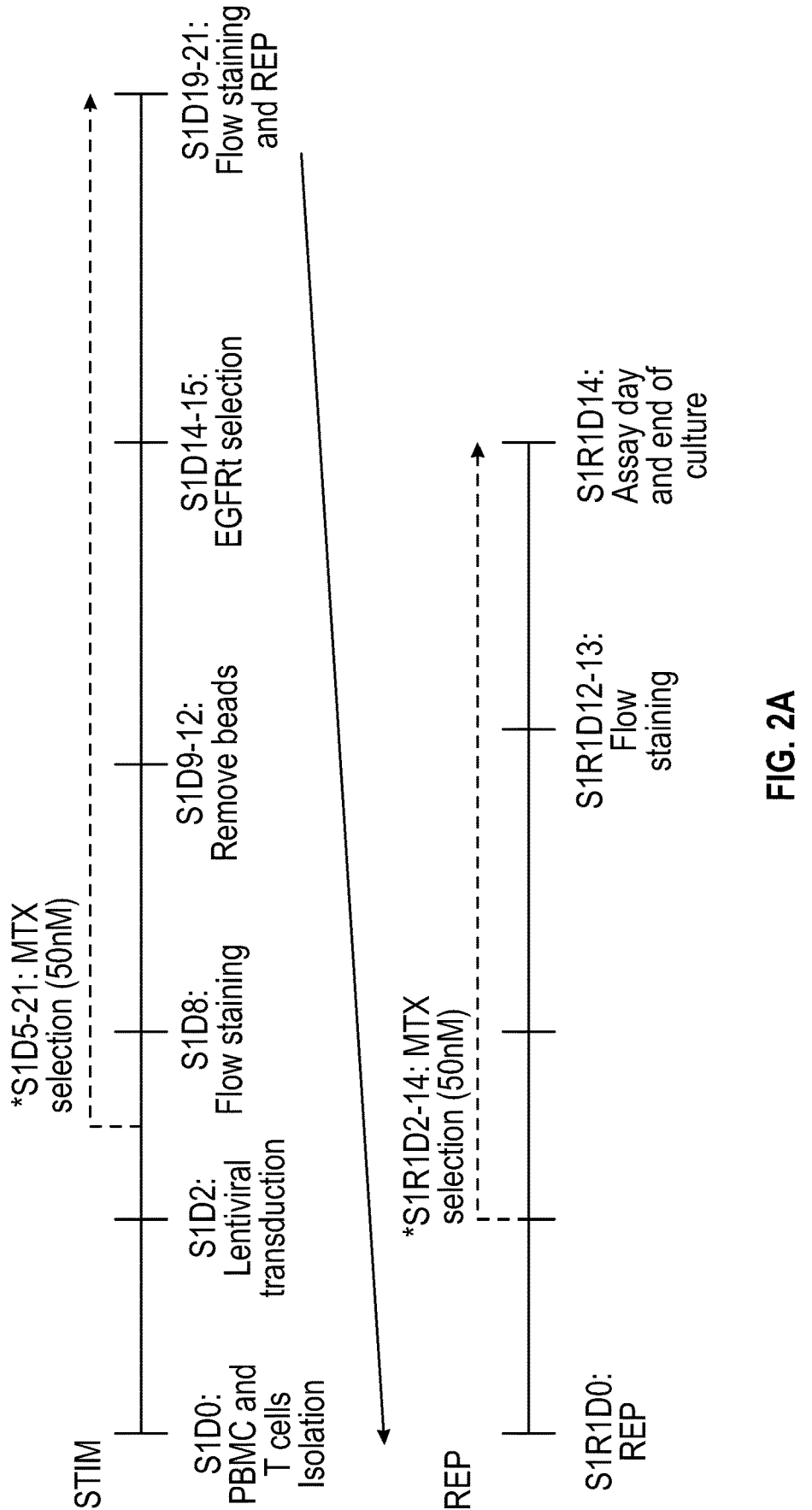
FIG. 2A depicts steps of a method for generating T cells expressing chimeric receptors, including steps for CD8+ selection and culture conditions. CD8 selection and culture conditions. CD8 T-cells were selected from PBMC using CD8 microbeads. Selected cells were stimulated with CD3/CD28 microbeads and then lent virally transduced with the constructs in FIG. 1. In some iterations (*), the CD8 T-cells were transduced with a construct that also contained a T2A-DHFRdm that was in-frame downstream to the EGFRt to allow for co-expression, allowing the selection of MTX-resistant T-cells co-expressing functionally relevant levels of IL13-zetakine CAR.
Figure 2B:
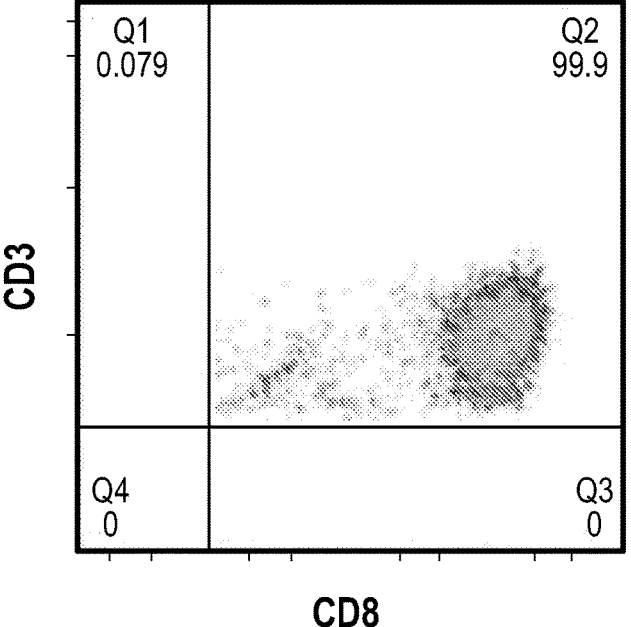
FIG. 2B depicts flow cytometry data for CD8+ T cells containing CARs that included either the S, M, or L spacer, and stained for a surrogate marker expression (EGFRt).
Figure 2B:
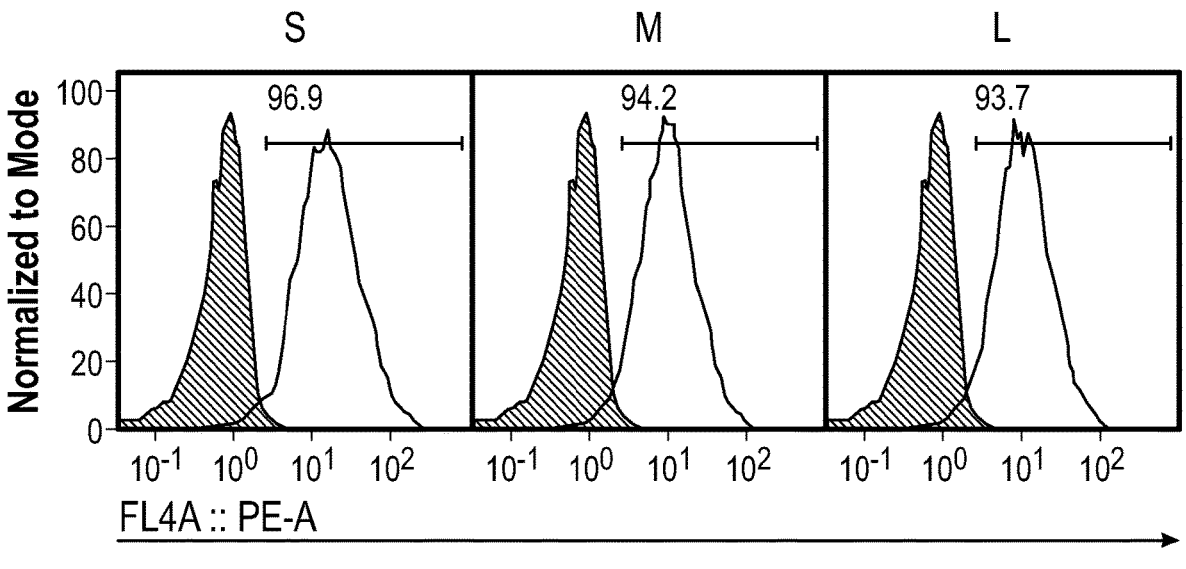

T cells containing the various CARs were generated according to the method depicted in FIG. 2A. CD8+ T-cells were selected from peripheral blood mononucleated cells (PBMCs) using microbeads. Selected cells were stimulated with CD3/CD28 microbeads and then lentivirally transduced with the constructs. In some iterations (*), the CD8 T-cells were transduced with a construct that also contained a T2A-DHFRdm that was in-frame downstream to the EGFRt to allow for co-expression, allowing the selection of MTX-resistant T-cells co-expressing functionally relevant levels of IL13-zetakine CAR. The cells were then subjected to flow staining for identifying cells carrying the zetakine CAR and selected using the EGFRt marker. Representative flow data demonstrated that the CD8+T− cells were efficiently selected and then subsequently enriched or selected (*) to near purity by surrogate marker expression (EGFRt) as shown in FIG. 2B.

Figure 3A:
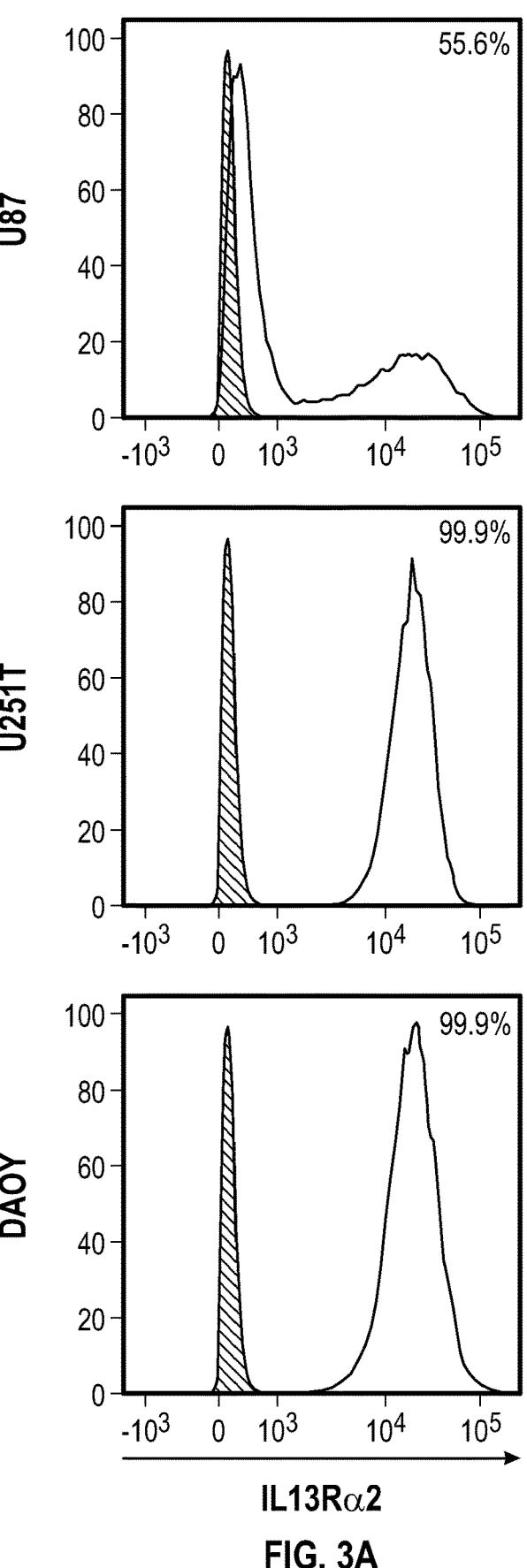
FIG. 3A depicts an IL13Ra2 expression analysis for target U87, U251T and DAOY tumor cell lines.
Figure 3B:
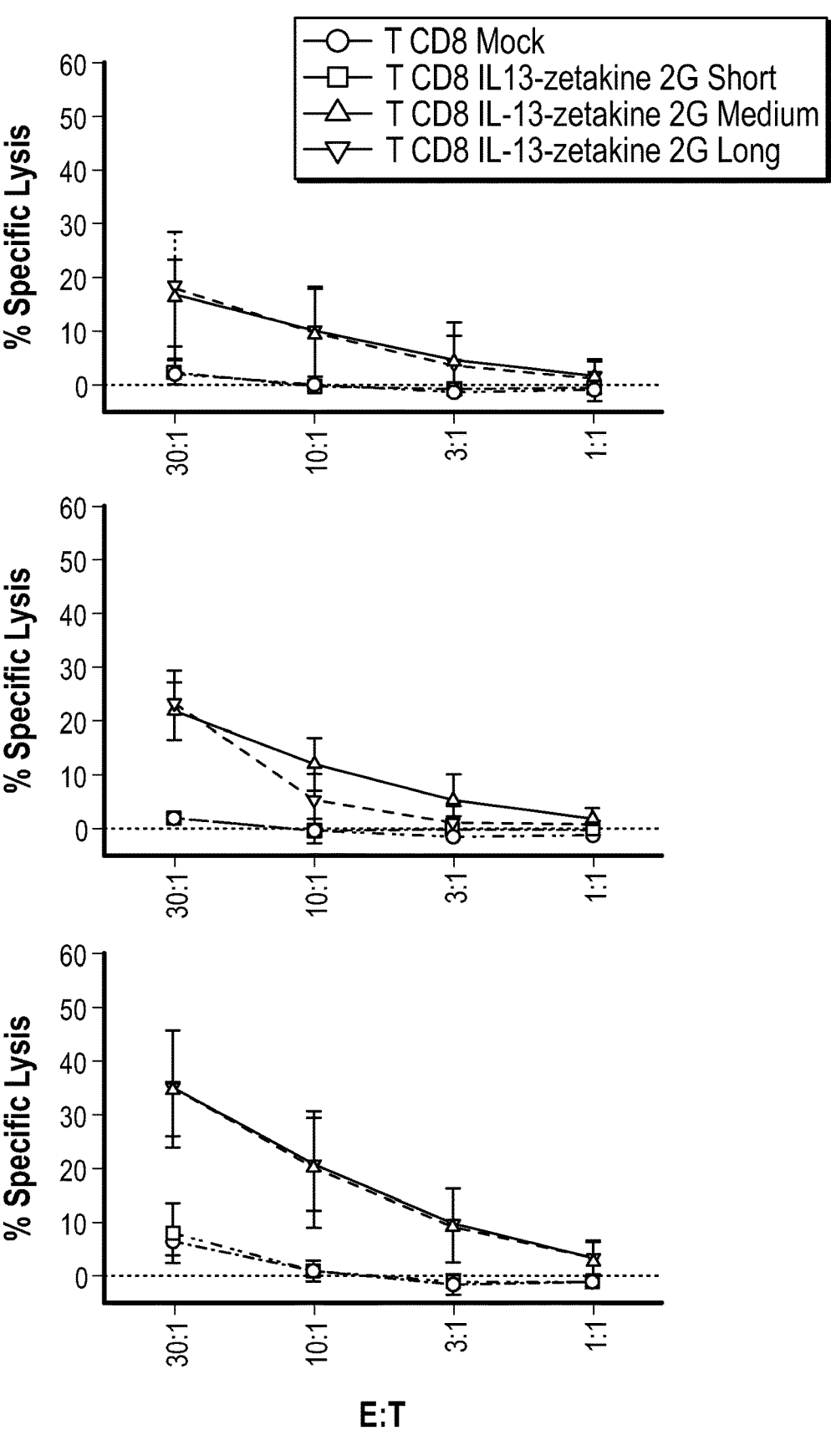
FIG. 3B depicts graphs for specific lysis of target cells (upper panel: U87; middle panel: U251T; and lower panel: DAOY) in the presence of effector CD8+ T cells containing CARs with either a S, M, or L spacer, at the indicated ratios. Data represent mean±SD of 3 different donors.

CD8+ T cells containing the zetakine CARs with either a S, M or L spacer were further characterized for specific lysis of target cells expressing IL13Rα2, and cytokine expression of the CD8+ T cells in the presence of target cells. Target cells U87, U251T and DAOY cells were analyzed for IL13Rα2 (FIG. 3A). In a 4-hr 51Cr cytotoxicity assay, labeled U87, U251T and DAOY tumor cell lines were cocultured with Mock or IL13-zetakine 2nd generation space-variants CAR T-cells (FIG. 3B). Both the M and L spacer IL13-zetakines CAR T-cells elicited specific lysis while the short spacer was unable to efficiently target IL13Rα2. Data represented mean±SD of 3 different donors.

Figure 3C:
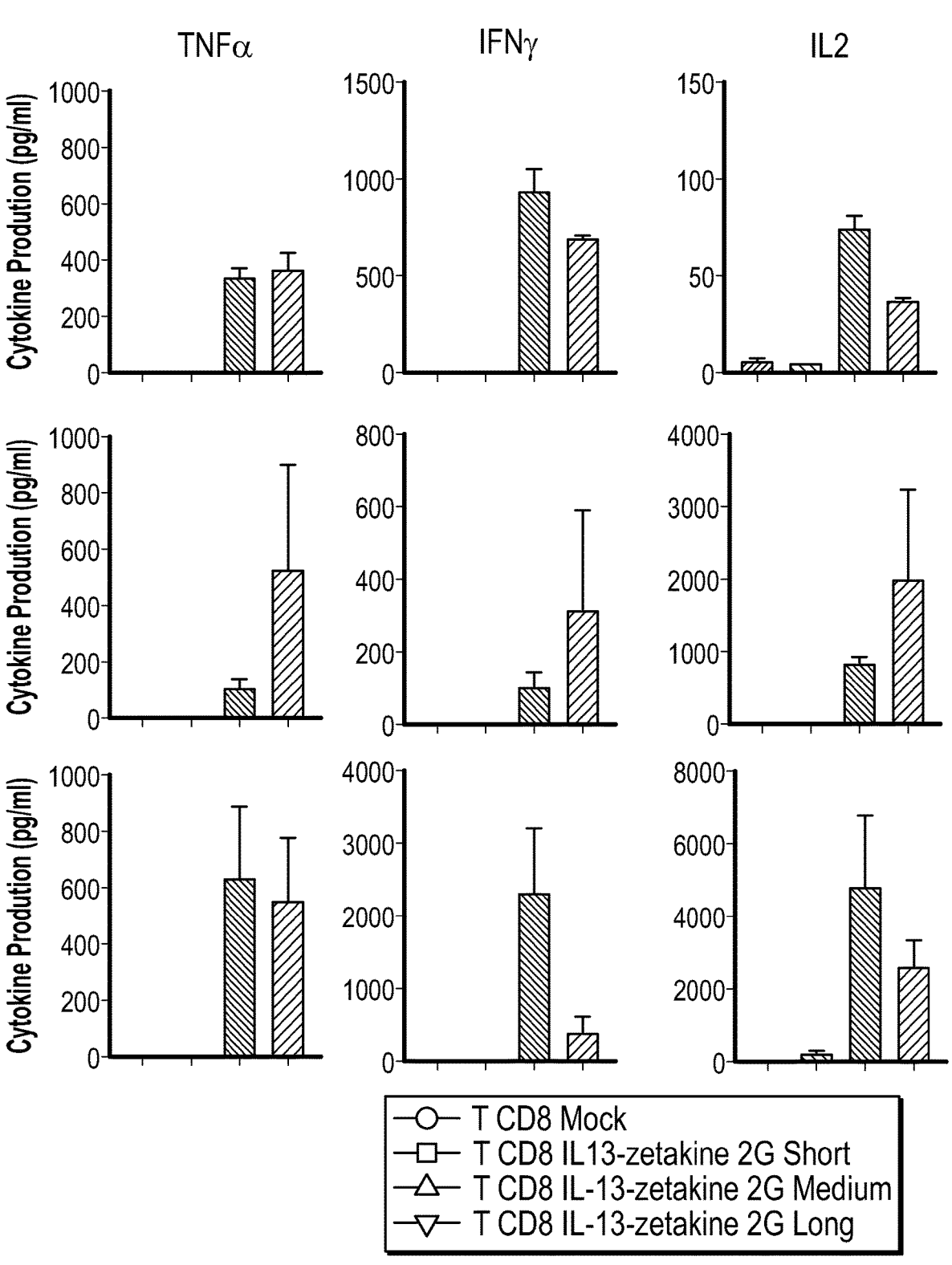
FIG. 3C depicts graphs of cytokine production for CD8+ T cells containing CARs with either a S, M, or L spacer in the presence of target cells (upper row: U87; middle row: U251T; and lower row: DAOY). Bars represent mean+SD.

In a cytokine release assay, T-cells containing the zetakine CARs were cultured with targets over a 24 hr period. Cell-free supernatants were harvested to measure TNFα, IFNγ, and IL-2 secretion. CD8+ T cells containing the zetakine CARs with either the M or L spacer had high levels of cytokine production, whereas the zetakine CAR with an S spacer had substantially no cytokine production (FIG. 3C).

Example 3—In Vivo Anti-Tumor Activity of IL13 Zetakine CARs

In vivo anti-tumor activity of IL13 zetakine CARs containing either the M spacer or the L spacer was tested. U87 glioblastoma cells labelled with ffLuc ($0.2 \times 10^6$) were intracranially injected into the forebrain of NSG mice at day 0. On day 7, mice (n=5 per group) received Mock T-cells or administration with different doses ($2 \times 10^6$, $1 \times 10^6$ T-cells) of IL13-zetakine 2nd generation medium or long spacer transduced CD8+ CAR T-cells.

Figure 4A:
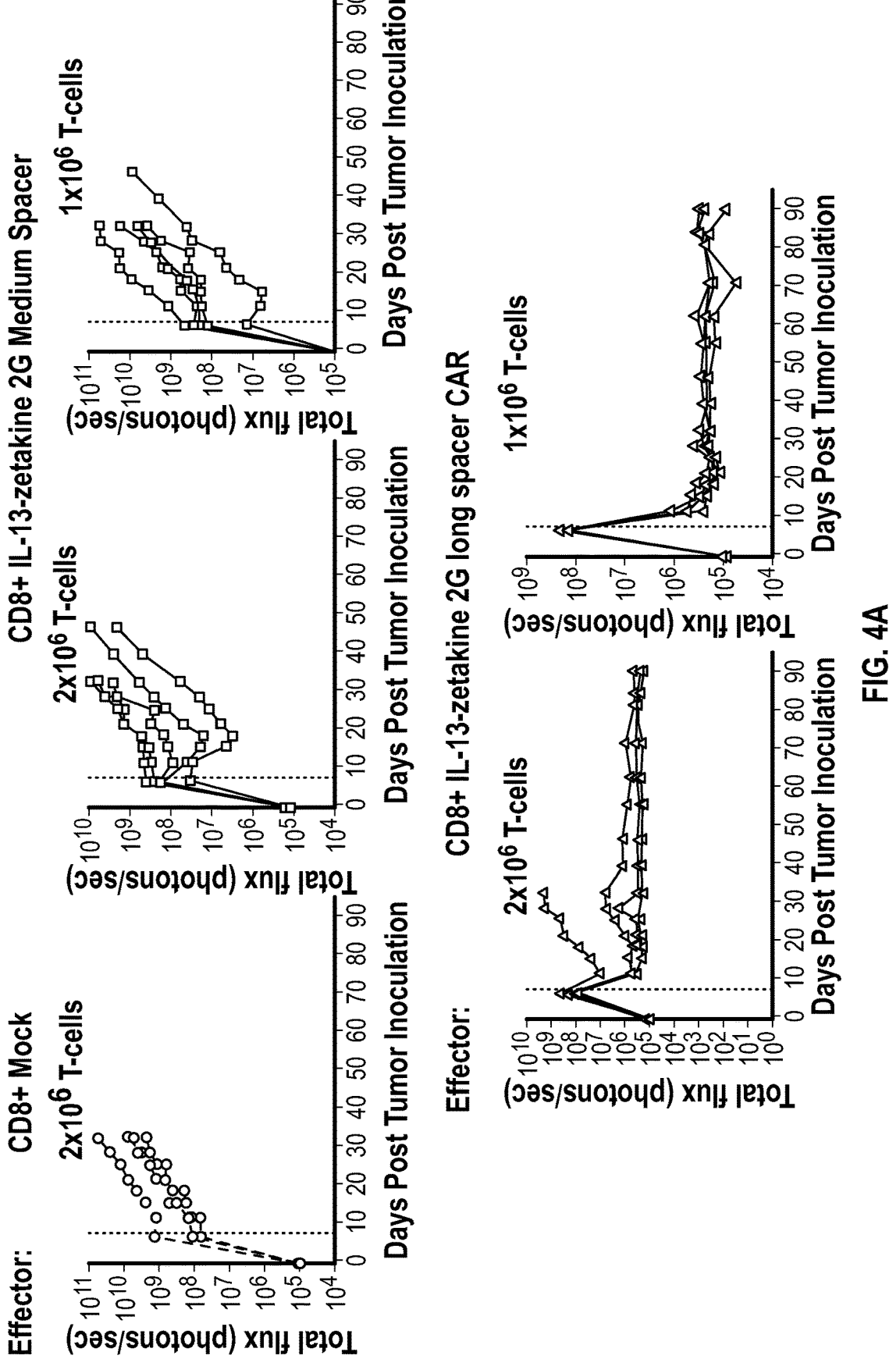
FIG. 4A depicts graphs of flux indicating tumor burden over time for mice injected with different doses of T cells containing IL13-zetakine CARs with either the M or L spacer.
Figure 4B:
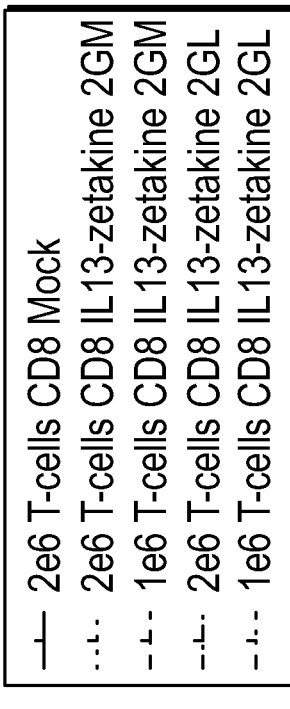
FIG. 4B depicts a Kaplan-Meier survival curve for mice injected with different doses of T cells containing IL13-zetakine CARs with either the M or L spacer.
Figure 4B:
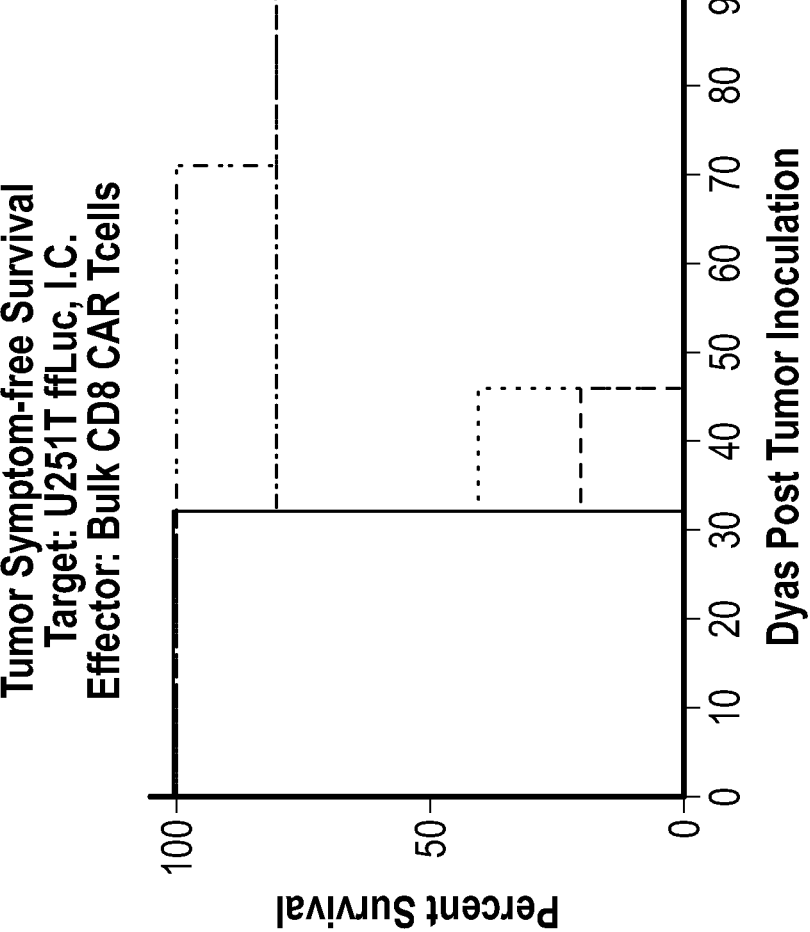

Total flux (photons/sec) from the U87 cells was measured as an indication of tumor burden. As shown in FIG. 4A, tumor burden in mice treated with cells containing the IL13 zetakine CAR containing the L spacer decreased with time, compared to mock treated mice, and mice treated with IL13 zetakine CAR containing the L spacer. A Kaplan-Meier survival curve demonstrated improved survival for mice administered with different doses of cells containing the IL13 zetakine CAR containing the L spacer (FIG. 4B).

Example 4—In Vitro Analysis of IL13 Zetakine CARs

Figure 5A:
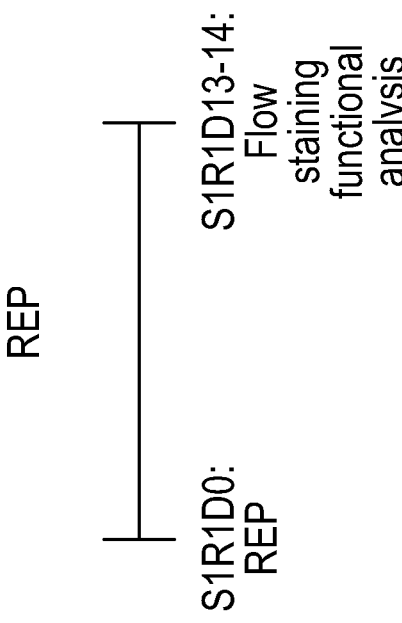
FIG. 5A depicts steps in a method for the preparation and analysis of cells containing IL13-zetakine CARs.
Figure 5A:
Figure 5A:
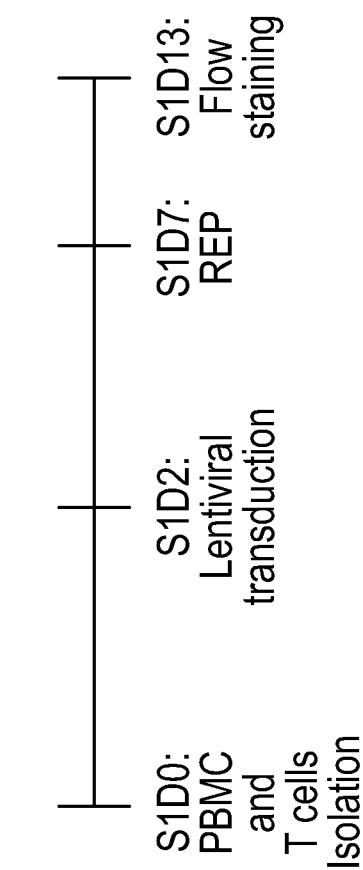
Figure 5B:
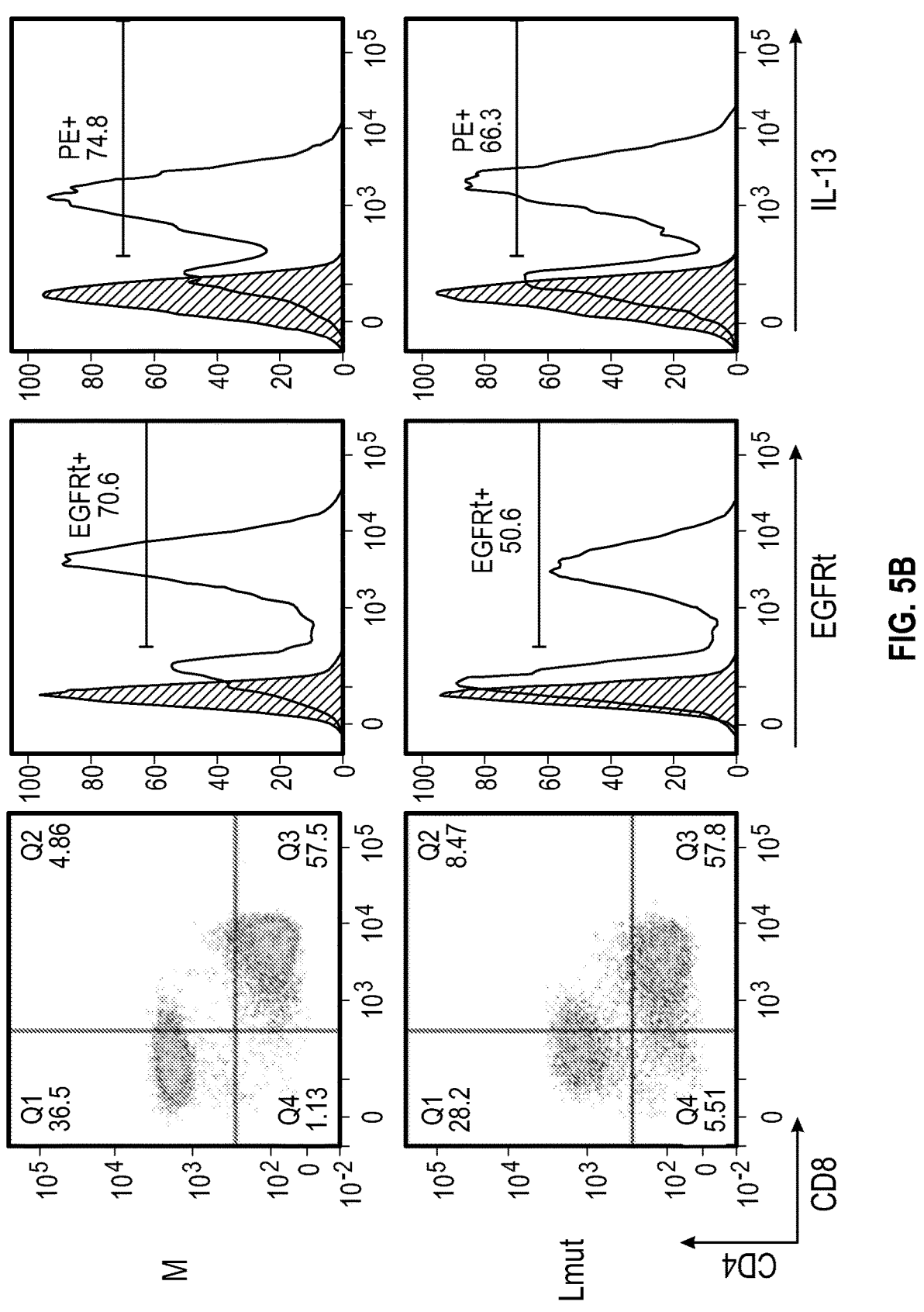
FIG. 5B depicts flow cytometry data with cells containing an IL13-zetakine CAR with either an M spacer or mutant L

Cells containing IL13 zetakine CAR with either the M spacer or the L spacer were prepared according to a method substantially similar to the method depicted in FIG. 5A. Briefly, CD4+ and CD8+ T cells were isolated and co-cultured. Two days later the T-cells were transduced with either the M-spacer IL-13-zetakine or L-spacer IL-13-zetakine. The cells were analyzed at end of stimulation (S1D13) for CD4:CD8 ratios, marker expression, and direct zetakine expression as stained by anti-IL-13 antibody (FIG. 5B).

Cells were tested in an in vitro functional analysis (FIG. 6). IL-13-zetakine directed T cells were subjected to a chromium release assay to assess degree of specific lysis following culture with IL-13Rα2-expressing target cells. In this assay stimulated, day fifteen (S1D15) T cells were co-cultured with different target cell lines at variable effector to target ratios. K562-OKT3 cells were used as a positive control for TCR complex driven T cell activation while the remaining cell lines all express IL-13Rα2 at variable levels (see top table). The bottom table represents the CD4 to CD8 ratio of the T cells and surrogate marker positivity. The assay was performed by normalizing total surrogate marker positive cells. Results demonstrate that both the M-spacer and L-spacer zetakines elicited lysis against IL-13Ra2 positive targets.

Example 5—In Vivo Anti-Tumor Activity of IL13 Zetakine CARs

As shown in FIG. 7, the M spacer and L spacer IL-13-zetakines were observed to inhibit tumor growth in a glioblastoma (GBM) model. Cells from Example 4 and S1D15 cells, were subjected to an orthotopic xenograft tumor model. In this model, U87 GFP: ffluc glioblastoma tumor cells were injected intracranially into NOD-Scid IL2yR-null mice. Seven days later, IL-13-zetakine directed T cells were injected into the same coordinates as the U87 GFP: ffluc tumor. M and L spacer IL-13-zetakine expressing T-cells were observed to inhibit tumor growth, as demonstrated by reduction in tumor burden in vivo, as assessed by flux emitted by the ffluc expressing U87 tumor (FIG. 7). Statistical analysis of delta-flux differences 26-days post tumor inoculation demonstrated that the M-spacer and L-spacer significantly inhibited flux onset relative to Mock (no IL-13-zetakine) T cells.

Example 6-In Vitro Analysis of IL13 Zetakine CARs

IL-13-zetakine directed T cells were subjected to a chromium release assay. In this assay rapidly expanded, day fourteen (S1R1D14) T cells were co-cultured with different target cell lines at variable effector to target ratios. K562-OKT3 were used as a positive control for TCR complex-driven T-cell activation while the remaining cell lines all express IL-13Rα2 at variable levels (see top table). Mock T-cells not transduced to express any of the zetakines were incorporated into this study as a negative control, demonstrating IL-13Rα2-specific lysis. The bottom table represents the CD4 to CD8 ratio of the T-cells and surrogate marker positivity. The assay was performed by normalizing total marker positive cells. Results demonstrated that both the M-spacer and L-spacer zetakines elicited lysis against IL13Rα2 positive targets. (FIG. 8)

In another study, IL-13-zetakine expressing T-cells were co-cultured for 24 hr with different target cell lines at a 2:1 effector-target ratio. Data demonstrated zetakines tested were able to elicit cytokine release upon IL-13Rα2 binding in a target-specific manner (FIG. 9).

TABLE 2 lists certain amino acid and nucleotide sequences for embodiments provided herein.

TABLE 2

| SEQ ID NO: | Feature(s) | Sequence |
|---|---|---|
| SEQ ID NO: 01 | Human IgG1 | EPKSCDKTHTCPPCP |
| SEQ ID NO: 02 | Human IgG2 | ERKCCVECPPCP |
| SEQ ID NO: 03 | Human IgG3 | ELKTPLGDTHTCPRCPEPKSCDTPPPCPRCP EPKSCDTPPPCPRCPEPKSCDTPPPCPRCP |
| SEQ ID NO: 04 | Human IgG4 | ESKYGPPCPSCP |
| SEQ ID NO: 05 | Modified Human IgG4 | ESKYGPPCPPCP |
| SEQ ID NO: 06 | Modified Human IgG4 | YGPPCPPCP |
| SEQ ID NO: 07 | Modified Human IgG4 | KYGPPCPPCP |
| SEQ ID NO: 08 | Modified Human IgG4 | EVVKYGPPCPPCP |
| SEQ ID NO: 09 | S spacer | ESKYGPPCPPCP |
| SEQ ID NO: 10 | M spacer | ESKYGPPCPPCPGQPREPQVYTLPPSQEEMTKNQVSL TCLVKGFYPSDIAVEWESNGQPENNYKTTPPVLDSD GSFFLYSRLTVDKSRWQEGNVFSCSVMHEALHNHY TQKSLSLSLGK |
| SEQ ID NO: 11 | L spacer | ESKYGPPCPPCPAPEFLGGPSVFLFPPKPKDTLMISRT PEVTCVVVDVSQEDPEVQFNWYVDGVEVHNAKTK PREEQFNSTYRVVSVLTVLHQDWLNGKEYKCKVSN KGLPSSIEKTISKAKGQPREPQVYTLPPSQEEMTKNQ VSLTCLVKGFYPSDIAVEWESNGQPENNYKTTPPVL DSDGSFFLYSRLTVDKSRWQEGNVFSCSVMHEALH NHYTQKSLSLSLGK |
| SEQ ID NO: 12 | Vector sequence including: IL13 zetakine-IgG4 hinge-CH3-CD28tm/4-1BB-zeta-T2A- | GTTAGACCAGATCTGAGCCTGGGAGCTCTCTGGCT AACTAGGGAACCCACTGCTTAAGCCTCAATAAAG CTTGCCTTGAGTGCTTCAAGTAGTGTGTGCCCGTC TGTTGTGTGACTCTGGTAACTAGAGATCCCTCAGA CCCTTTTAGTCAGTGTGGAAAATCTCTAGCAGTGG CGCCCGAACAGGGACTTGAAAGCGAAAGGGAAA |

TABLE 2-continued

| SEQ ID NO: | Feature(s) | Sequence |
|---|---|---|
| | EGFRt<br>IL13 zetakine is<br>underlined | CCAGAGGAGCTCTCTCGACGCAGGACTCGGCTTG<br>CTGAAGCGCGCACGGCAAGAGGCGAGGGGCGGC<br>GACTGGTGAGTACGCCAAAAATTTTGACTAGCGG<br>AGGCTAGAAGGAGAGAGATGGGTGCGAGAGCGT<br>CAGTATTAAGCGGGGGAGAATTAGATCGATGGGA<br>AAAAATTCGGTTAAGGCCAGGGGGAAAGAAAAA<br>ATATAAATTAAAACATATAGTATGGGCAAGCAGG<br>GAGCTAGAACGATTCGCAGTTAATCCTGGCCTGTT<br>AGAAACATCAGAAGGCTGTAGACAAATACTGGGA<br>CAGCTACAACCATCCCTTCAGACAGGATCAGAAG<br>AACTTAGATCATTATATAATACAGTAGCAACCCTC<br>TATTGTGTGCATCAAAGGATAGAGATAAAAGACA<br>CCAAGGAAGCTTTAGACAAGATAGAGGAAGAGCA<br>AAACAAAAGTAAGAAAAAAGCACAGCAAGCAGC<br>AGCTGACACAGGACACAGCAATCAGGTCAGCCAA<br>AATTACCCTATAGTGCAGAACATCCAGGGGCAAA<br>TGGTACATCAGGCCATATCACCTAGAACTTTAAAT<br>GCATGGGTAAAAGTAGTAGAAGAGAAGGCTTTCA<br>GCCCAGAAGTGATACCCATGTTTTCAGCATTATCA<br>GAAGGAGCCACCCCACAAGATTTAAACACCATGC<br>TAAACACAGTGGGGGGACATCAAGCAGCCATGCA<br>AATGTTAAAAGAGACCATCAATGAGGAAGCTGCA<br>GGCAAAGAGAAGAGTGGTGCAGAGAGAAAAAAG<br>AGCAGTGGGAATAGGAGCTTTGTTCCTTGGGTTCT<br>TGGGAGCAGCAGGAAGCACTATGGGCGCAGCGTC<br>AATGACGCTGACGGTACAGGCCAGACAATTATTG<br>TCTGGTATAGTGCAGCAGCAGAACAATTTGCTGA<br>GGGCTATTGAGGCGCAACAGCATCTGTTGCAACT<br>CACAGTCTGGGGCATCAAGCAGCTCCAGGCAAGA<br>ATCCTGGCTGTGGAAAGATACCTAAAGGATCAAC<br>AGCTCCTGGGGATTTGGGGTTGCTCTGGAAAACTC<br>ATTTGCACCACTGCTGTGCCTTGGATCTACAAATG<br>GCAGTATTCATCCACAATTTTAAAAGAAAAGGGG<br>GGATTGGGGGGTACAGTGCAGGGGAAAGAATAGT<br>AGACATAATAGCAACAGACATACAAACTAAAGAA<br>TTACAAAAACAAATTACAAAAATTCAAAATTTTC<br>GGGTTTATTACAGGGACAGCAGAGATCCAGTTTG<br>GGGATCAATTGCATGAAGAATCTGCTTAGGGTTA<br>GGCGTTTTGCGCTGCTTCGCGAGGATCTGCGATCG<br>CTCCGGTGCCCGTCAGTGGGCAGAGCGCACATCG<br>CCCACAGTCCCCGAGAAGTTGGGGGGAGGGGTCG<br>GCAATTGAACCGGTGCCTAGAGAAGGTGGCGCGG<br>GGTAAACTGGGAAAGTGATGTCGTGTACTGGCTC<br>CGCCTTTTTCCCGAGGGTGGGGGAGAACCGTATAT<br>AAGTGCAGTAGTCGCCGTGAACGTTCTTTTTCGCA<br>ACGGGTTTGCCGCCAGAACACAGCTGGGCTAGCG<br>TTTAAACGGGCCCTCTAGAGCCGCCACCATGCTTC<br>TCCTGGTGACAAGCCTTCTGCTCTGTGAGTTACCA<br><u>CACCCAGCATTCCTCCTGATCCCAGGCCCTGTGCC</u><br><u>TCCCTCTACAGCCCTCAGGTACCTCATTGAGGAGC</u><br><u>TGGTCAACATCACCCAGAACCAGAAGGCTCCGCT</u><br><u>CTGCAATGGCAGCATGGTATGGAGCATCAACCTG</u><br><u>ACAGCTGGCATGTACTGTGCAGCCCTGGAATCCCT</u><br><u>GATCAACGTGTCAGGCTGCAGTGCCATCGAGAAG</u><br><u>ACCCAGAGGATGCTGAGCGGATTCTGCCCGCACA</u><br><u>AGGTCTCAGCTGGGCAGTTTTCCAGCTTGCATGTC</u><br><u>CGAGACACCAAAATCGAGGTGGCCCAGTTTGTAA</u><br>AGGACCTGCTCTTACATTTAAAGAAACTTTTTCGC<br>GAGGGACGGTTCAAGAATCTAAGTACCGGACCGC<br>CCTGCCCCCCTTGCCCTGGCCAGCCTAGAGAACCC<br>CAGGTGTACACCCTGCCTCCCAGCCAGGAAGAGA<br>TGACCAAGAACCAGGTGTCCCTGACCTGCCTGGTC<br>AAAGGCTTCTACCCCAGCGATATCGCCGTGGAAT<br>GGGAGAGCAACGGCCAGCCCGAGAACAACTACA<br>AGACCACCCCCCCTGTGCTGGACAGCGACGGCAG<br>CTTCTTCCTGTACTCCCGGCTGACCGTGGACAAGA<br>GCCGGTGGCAGGAAGGCAACGTCTTCAGCTGCAG<br>CGTGATGCACGAGGCCCTGCACAACCACTACACC<br>CAGAAGTCCCTGAGCCTGAGCCTGGGCAAGATGT<br>TCTGGGTGCTGGTGGTGGTCGGAGGCGTGCTGGC<br>CTGCTACAGCCTGCTGGTCACCGTGGCCTTCATCA<br>TCTTTTGGGTGAAACGGGGCAGAAAGAAACTCCT<br>GTATATATTCAAACAACCATTTATGAGACCAGTAC<br>AAACTACTCAAGAGGAAGATGGCTGTAGCTGCCG<br>ATTTCCAGAAGAAGAAGAAGGAGGATGTGAACTG<br>CGGGTGAAGTTCAGCAGAAGCGCCGACGCCCCTG<br>CCTACCAGCAGGGCCAGAATCAGCTGTACAACGA<br>GCTGAACCTGGGCAGAAGGGAAGAGTACGACGTC |

TABLE 2-continued

| SEQ ID NO: | Feature(s) | Sequence |
|---|---|---|
| | | CTGGATAAGCGGAGAGGCCGGGACCCTGAGATGG |
| | | GCGGCAAGCCTCGGCGGAAGAACCCCCAGGAAGG |
| | | CCTGTATAACGAACTGCAGAAAGACAAGATGGCC |
| | | GAGGCCTACAGCGAGATCGGCATGAAGGGCGAGC |
| | | GGAGGCGGGGCAAGGGCCACGACGGCCTGTATCA |
| | | GGGCCTGTCCACCGCCACCAAGGATACCTACGAC |
| | | GCCCTGCACATGCAGGCCCTGCCCCCAAGGCTCG |
| | | AGGGCGGCGGAGAGGGCAGAGGAAGTCTTCTAAC |
| | | ATGCGGTGACGTGGAGGAGAATCCCGGCCCTAGG |
| | | ATGCTTCTCCTGGTGACAAGCCTTCTGCTCTGTGA |
| | | GTTACCACACCCAGCATTCCTCCTGATCCCACGCA |
| | | AAGTGTGTAACGGAATAGGTATTGGTGAATTTAA |
| | | AGACTCACTCTCCATAAATGCTACGAATATTAAAC |
| | | ACTTCAAAAACTGCACCTCCATCAGTGGCGATCTC |
| | | CACATCCTGCCGGTGGCATTTAGGGGTGACTCCTT |
| | | CACACATACTCCTCCTCTGGATCCACAGGAACTGG |
| | | ATATTCTGAAAACCGTAAAGGAAATCACAGGGTT |
| | | TTTGCTGATTCAGGCTTGGCCTGAAAACAGGACG |
| | | GACCTCCATGCCTTTGAGAACCTAGAAATCATACG |
| | | CGGCAGGACCAAGCAACATGGTCAGTTTTCTCTTG |
| | | CAGTCGTCAGCCTGAACATAACATCCTTGGGATTA |
| | | CGCTCCCTCAAGGAGATAAGTGATGGAGATGTGA |
| | | TAATTTCAGGAAACAAAAATTTGTGCTATGCAAAT |
| | | ACAATAAACTGGAAAAAACTGTTTGGGACCTCCG |
| | | GTCAGAAAACCAAAATTATAAGCAACAGAGGTGA |
| | | AAACAGCTGCAAGGCCACAGGCCAGGTCTGCCAT |
| | | GCCTTGTGCTCCCCGAGGGCTGCTGGGGCCCGG |
| | | AGCCCAGGGACTGCGTCTCTTGCCGGAATGTCAG |
| | | CCGAGGCAGGGAATGCGTGGACAAGTGCAACCTT |
| | | CTGGAGGGTGAGCCAAGGGAGTTTGTGGAGAACT |
| | | CTGAGTGCATACAGTGCCACCCAGAGTGCCTGCCT |
| | | CAGGCCATGAACATCACCTGCACAGGACGGGGAC |
| | | CAGACAACTGTATCCAGTGTGCCCACTACATTGAC |
| | | GGCCCCCACTGCGTCAAGACCTGCCCGGCAGGAG |
| | | TCATGGGAGAAAACAACACCCTGGTCTGGAAGTA |
| | | CGCAGACGCCGGCCATGTGTGCCACCTGTGCCATC |
| | | CAAACTGCACCTACGGATGCACTGGGCCAGGTCT |
| | | TGAAGGCTGTCCAACGAATGGGCCTAAGATCCCG |
| | | TCCATCGCCACTGGGATGGTGGGGGCCCTCCTCTT |
| | | GCTGCTGGTGGTGGCCCTGGGGATCGGCCTCTTCA |
| | | TGTGAGCGGCCGCTCTAGACCCGGGCTGCAGGAA |
| | | TTCGATATCAAGCTTATCGATAATCAACCTCTGGA |
| | | TTACAAAATTTGTGAAAGATTGACTGGTATTCTTA |
| | | ACTATGTTGCTCCTTTTACGCTATGTGGATACGCT |
| | | GCTTTAATGCCTTTGTATCATGCTATTGCTTCCCGT |
| | | ATGGCTTTCATTTTCTCCTCCTTGTATAAATCCTGG |
| | | TTGCTGTCTCTTTATGAGGAGTTGTGGCCCGTTGT |
| | | CAGGCAACGTGGCGTGGTGTGCACTGTGTTTGCTG |
| | | ACGCAACCCCCACTGGTTGGGGCATTGCCACCAC |
| | | CTGTCAGCTCCTTTCCGGGACTTTCGCTTTCCCCCT |
| | | CCCTATTGCCACGGCGGAACTCATCGCCGCCTGCC |
| | | TTGCCCGCTGCTGGACAGGGGCTCGGCTGTTGGGC |
| | | ACTGACAATTCCGTGGTGTTGTCGGGGAAATCATC |
| | | GTCCTTTCCTTGGCTGCTCGCCTGTGTTGCCACCTG |
| | | GATTCTGCGCGGGACGTCCTTCTGCTACGTCCCTT |
| | | CGGCCCTCAATCCAGCGGACCTTCCTTCCCGCGGC |
| | | CTGCTGCCGGCTCTGCGGCCTCTTCCGCGTCTTCG |
| | | CCTTCGCCCTCAGACGAGTCGGATCTCCCTTTGGG |
| | | CCGCCTCCCCGCATCGATACCGTCGACTAGCCGTA |
| | | CCTTTAAGACCAATGACTTACAAGGCAGCTGTAG |
| | | ATCTTAGCCACTTTTTAAAAGAAAAGGGGGGACT |
| | | GGAAGGGCTAATTCACTCCCAAAGAAGACAAGAT |
| | | CTGCTTTTTGCCTGTACTGGGTCTCTCTGGTTAGAC |
| | | CAGATCTGAGCCTGGGAGCTCTCTGGCTAACTAG |
| | | GGAACCCACTGCTTAAGCCTCAATAAAGCTTGCCT |
| | | TGAGTGCTTCAAGTAGTGTGTGCCCGTCTGTTGTG |
| | | TGACTCTGGTAACTAGAGATCCCTCAGACCCTTTT |
| | | AGTCAGTGTGGAAAATCTCTAGCAGAATTCGATA |
| | | TCAAGCTTATCGATACCGTCGACCTCGAGGGGGG |
| | | GCCCGGTACCGAGCTCGGATCCACTAGTCCAGTGT |
| | | GGTGGAATTCTGCAGATATCCAGCACAGTGGCGG |
| | | CCACTCAAGTCTGGAGGGCACGTTAAAACCCGCT |
| | | GATCAGCCTCGACTGTGCCTTCTAGTTGCCAGCCA |
| | | TCTGTTGTTTGCCCCTCCCCCGTGCCTTCCTTGACC |
| | | CTGGAAGGTGCCACTCCCACTGTCCTTTCCTAATA |
| | | AAATGAGGAAATTGCATCGCATTGTCTGAGTAGG |
| | | TGTCATTCTATTCTGGGGGGTGGGGTGGGGCAGG |
| | | ACAGCAAGGGGGAGGATTGGGAAGACAATAGCA |

TABLE 2-continued

| SEQ ID NO: | Feature(s) | Sequence |
|---|---|---|
| | | GGCATGCTGGGGATGCGGTGGGCTCTATGGCTTCT |
| | | ACTGGGCGGTTTTATGGACAGCAAGCGAACCGGA |
| | | ATTGCCAGCTGGGGCGCCCTCTGGTAAGGTTGGG |
| | | AAGCCCTGCAAAGTAAACTGGATGGCTTTCTCGCC |
| | | GCCAAGGATCTGATGGCGCAGGGGATCAAGCTCT |
| | | GATCAAGAGACAGGATGAGGATCGTTTCGCATGA |
| | | TTGAACAAGATGGATTGCACGCAGGTTCTCCGGC |
| | | CGCTTGGGTGGAGAGGCTATTCGGCTATGACTGG |
| | | GCACAACAGACAATCGGCTGCTCTGATGCCGCCG |
| | | TGTTCCGGCTGTCAGCGCAGGGGCGCCCGGTTCTT |
| | | TTTGTCAAGACCGACCTGTCCGGTGCCCTGAATGA |
| | | ACTGCAAGACGAGGCAGCGCGGCTATCGTGGCTG |
| | | GCCACGACGGGCGTTCCTTGCGCAGCTGTGCTCGA |
| | | CGTTGTCACTGAAGCGGGAAGGGACTGGCTGCTA |
| | | TTGGGCGAAGTGCCGGGGCAGGATCTCCTGTCAT |
| | | CTCACCTTGCTCCTGCCGAGAAAGTATCCATCATG |
| | | GCTGATGCAATGCGGCGGCTGCATACGCTTGATCC |
| | | GGCTACCTGCCCATTCGACCACCAAGCGAAACAT |
| | | CGCATCGAGCGAGCACGTACTCGGATGGAAGCCG |
| | | GTCTTGTCGATCAGGATGATCTGGACGAAGAGCA |
| | | TCAGGGGCTCGCGCCAGCCGAACTGTTCGCCAGG |
| | | CTCAAGGCGAGCATGCCCGACGGCGAGGATCTCG |
| | | TCGTGACCCATGGCGATGCCTGCTTGCCGAATATC |
| | | ATGGTGGAAAATGGCCGCTTTTCTGGATTCATCGA |
| | | CTGTGGCCGGCTGGGTGTGGCAGACCGCTATCAG |
| | | GACATAGCGTTGGCTACCCGTGATATTGCTGAAG |
| | | AGCTTGGCGGCGAATGGGCTGACCGCTTCCTCGTG |
| | | CTTTACGGTATCGCCGCTCCCGATTCGCAGCGCAT |
| | | CGCCTTCTATCGCCTTCTTGACGAGTTCTTCTGAAT |
| | | TATTAACGCTTACAATTTCCTGATGCGGTATTTTCT |
| | | CCTTACGCATCTGTGCGGTATTTCACACCGCATAC |
| | | AGGTGGCACTTTTCGGGGAAATGTGCGCGGAACC |
| | | CCTATTTGTTTATTTTTCTAAATACATTCAAATATG |
| | | TATCCGCTCATGACCAAAATCCCTTAACGTGAGTT |
| | | TTCGTTCCACTGAGCGTCAGACCCCGTAGAAAAG |
| | | ATCAAAGGATCTTCTTGAGATCCTTTTTTTCTGCG |
| | | CGTAATCTGCTGCTTGCAAACAAAAAAACCACCG |
| | | CTACCAGCGGTGGTTTGTTTGCCGGATCAAGAGCT |
| | | ACCAACTCTTTTTCCGAAGGTAACTGGCTTCAGCA |
| | | GAGCGCAGATACCAAATACTGTTCTTCTAGTGTAG |
| | | CCGTAGTTAGGCCACCACTTCAAGAACTCTGTAGC |
| | | ACCGCCTACATACCTCGCTCTGCTAATCCTGTTAC |
| | | CAGTGGCTGCTGCCAGTGGCGATAAGTCGTGTCTT |
| | | ACCGGGTTGGACTCAAGACGATAGTTACCGGATA |
| | | AGGCGCAGCGGTCGGGCTGAACGGGGGGTTCGTG |
| | | CACACAGCCCAGCTTGGAGCGAACGACCTACACC |
| | | GAACTGAGATACCTACAGCGTGAGCTATGAGAAA |
| | | GCGCCACGCTTCCCGAAGGGAGAAAGGCGGACAG |
| | | GTATCCGGTAAGCGGCAGGGTCGGAACAGGAGAG |
| | | CGCACGAGGGAGCTTCCAGGGGGAAACGCCTGGT |
| | | ATCTTTATAGTCCTGTCGGGTTTCGCCACCTCTGA |
| | | CTTGAGCGTCGATTTTTGTGATGCTCGTCAGGGGG |
| | | GCGGAGCCTATGGAAAAACGCCAGCAACGCGGCC |
| | | TTTTTACGGTTCCTGGCCTTTTGCTGGCCTTTTGCT |
| | | CACATGTTCTTTCCTGCGTTATCCCCTGATTCTGTG |
| | | GATAACCGTATTACCGCCTTTGAGTGAGCTGATAC |
| | | CGCTCGCCGCAGCCGAACGACCGAGCGCAGCGAG |
| | | TCAGTGAGCGAGGAAGCGGAAGAGCGCCCAATAC |
| | | GCAAACCGCCTCTCCCCGCGCGTTGGCCGATTCAT |
| | | TAATGCAGCTGGCACGACAGGTTTCCCGACTGGA |
| | | AAGCGGGCAGTGAGCGCAACGCAATTAATGTGAG |
| | | TTAGCTCACTCATTAGGCACCCCAGGCTTTACACT |
| | | TTATGCTTCCGGCTCGTATGTTGTGTGGAATTGTG |
| | | AGCGGATAACAATTTCACACAGGAAACAGCTATG |
| | | ACCATGATTACGCCAAGCTCGAAATTAACCCTCAC |
| | | TAAAGGGAACAAAAGCTGGAGCTCCACCGCGGTG |
| | | GCGGCCTCGAGGTCGAGATCCGGTCGACCAGCAA |
| | | CCATAGTCCCGCCCCTAACTCCGCCCATCCCGCCC |
| | | CTAACTCCGCCCAGTTCCGCCCATTCTCCGCCCCA |
| | | TGGCTGACTAATTTTTTTTATTTATGCAGAGGCCG |
| | | AGGCCGCCTCGGCCTCTGAGCTATTCCAGAAGTA |
| | | GTGAGGAGGCTTTTTTGGAGGCCTAGGCTTTTGCA |
| | | AAAAGCTTCGACGGTATCGATTGGCTCATGTCCAA |
| | | CATTACCGCCATGTTGACATTGATTATTGACTAGT |
| | | TATTAATAGTAATCAATTACGGGGTCATTAGTTCA |
| | | TAGCCCATATATGGAGTTCCGCGTTACATAACTTA |
| | | CGGTAAATGGCCCGCCTGGCTGACCGCCCAACGA |
| | | CCCCCGCCCATTGACGTCAATAATGACGTATGTTC |

TABLE 2-continued

| SEQ ID NO: | Feature(s) | Sequence |
|---|---|---|
| | | CCATAGTAACGCCAATAGGGACTTTCCATTGACGT |
| | | CAATGGGTGGAGTATTTACGGTAAACTGCCCACTT |
| | | GGCAGTACATCAAGTGTATCATATGCCAAGTACG |
| | | CCCCCTATTGACGTCAATGACGGTAAATGGCCCGC |
| | | CTGGCATTATGCCCAGTACATGACCTTATGGGACT |
| | | TTCCTACTTGGCAGTACATCTACGTATTAGTCATC |
| | | GCTATTACCATGGTGATGCGGTTTTGGCAGTACAT |
| | | CAATGGGCGTGGATAGCGGTTTGACTCACGGGGA |
| | | TTTCCAAGTCTCCACCCCATTGACGTCAATGGGAG |
| | | TTTGTTTTGGCACCAAAATCAACGGGACTTTCCAA |
| | | AATGTCGTAACAACTCCGCCCCATTGACGCAAAT |
| | | GGGCGGTAGGCGTGTACGGAATTCGGAGTGGCGA |
| | | GCCCTCAGATCCTGCATATAAGCAGCTGCTTTTTG |
| | | CCTGTACTGGGTCTCTCTG |
| SEQ ID NO: 13 | Vector sequence including: IL13 zetakine-IgG4 hinge-CH3-CD28tm/4-1BB-zeta-T2A-EGFRt IL13 zetakine is underlined | GTTAGACCAGATCTGAGCCTGGGAGCTCTCTGGCT |
| | | AACTAGGGAACCCACTGCTTAAGCCTCAATAAAG |
| | | CTTGCCTTGAGTGCTTCAAGTAGTGTGTGCCCGTC |
| | | TGTTGTGTGACTCTGGTAACTAGAGATCCCTCAGA |
| | | CCCTTTTAGTCAGTGTGGAAAATCTCTAGCAGTGG |
| | | CGCCCGAACAGGGACTTGAAAGCGAAAGGGAAA |
| | | CCAGAGGAGCTCTCTCGACGCAGGACTCGGCTTG |
| | | CTGAAGCGCGCACGGCAAGAGGCGAGGGGCGGC |
| | | GACTGGTGAGTACGCCAAAAATTTTGACTAGCGG |
| | | AGGCTAGAAGGAGAGAGATGGGTGCGAGAGCGT |
| | | CAGTATTAAGCGGGGGAGAATTAGATCGATGGGA |
| | | AAAAATTCGGTTAAGGCCAGGGGGAAAGAAAAA |
| | | ATATAAATTAAAACATATAGTATGGGCAAGCAGG |
| | | GAGCTAGAACGATTCGCAGTTAATCCTGGCCTGTT |
| | | AGAAACATCAGAAGGCTGTAGACAAATACTGGGA |
| | | CAGCTACAACCATCCCTTCAGACAGGATCAGAAG |
| | | AACTTAGATCATTATATAATACAGTAGCAACCCTC |
| | | TATTGTGTGCATCAAAGGATAGAGATAAAAGACA |
| | | CCAAGGAAGCTTTAGACAAGATAGAGGAAGAGCA |
| | | AAACAAAAGTAAGAAAAAAGCACAGCAAGCAGC |
| | | AGCTGACACAGGACACAGCAATCAGGTCAGCCAA |
| | | AATTACCCTATAGTGCAGAACATCCAGGGGCAAA |
| | | TGGTACATCAGGCCATATCACCTAGAACTTTAAAT |
| | | GCATGGGTAAAAGTAGTAGAAGAGAAGGCTTTCA |
| | | GCCCAGAAGTGATACCCATGTTTTCAGCATTATCA |
| | | GAAGGAGCCACCCCACAAGATTTAAACACCATGC |
| | | TAAACACAGTGGGGGGACATCAAGCAGCCATGCA |
| | | AATGTTAAAAGAGACCATCAATGAGGAAGCTGCA |
| | | GGCAAAGAGAAGAGTGGTGCAGAGAGAAAAAAG |
| | | AGCAGTGGGAATAGGAGCTTTGTTCCTTGGGTTCT |
| | | TGGGAGCAGCAGGAAGCACTATGGGCGCAGCGTC |
| | | AATGACGCTGACGGTACAGGCCAGACAATTATTG |
| | | TCTGGTATAGTGCAGCAGCAGAACAATTTGCTGA |
| | | GGGCTATTGAGGCGCAACAGCATCTGTTGCAACT |
| | | CACAGTCTGGGGCATCAAGCAGCTCCAGGCAAGA |
| | | ATCCTGGCTGTGGAAAGATACCTAAAGGATCAAC |
| | | AGCTCCTGGGGATTTGGGGTTGCTCTGGAAAACTC |
| | | ATTTGCACCACTGCTGTGCCTTGGATCTACAAATG |
| | | GCAGTATTCATCCACAATTTTAAAAGAAAAGGGG |
| | | GGATTGGGGGGTACAGTGCAGGGGAAAGAATAGT |
| | | AGACATAATAGCAACAGACATACAAACTAAAGAA |
| | | TTACAAAAACAAATTACAAAAATTCAAAATTTTC |
| | | GGGTTTATTACAGGGACAGCAGAGATCCAGTTTG |
| | | GGGATCAATTGCATGAAGAATCTGCTTAGGGTTA |
| | | GGCGTTTTGCGCTGCTTCGCGAGGATCTGCGATCG |
| | | CTCCGGTGCCCGTCAGTGGGCAGAGCGCACATCG |
| | | CCCACAGTCCCCGAGAAGTTGGGGGGAGGGGTCG |
| | | GCAATTGAACCGGTGCCTAGAGAAGGTGGCGCGG |
| | | GGTAAACTGGGAAAGTGATGTCGTGTACTGGCTC |
| | | CGCCTTTTTCCCGAGGGTGGGGGAGAACCGTATAT |
| | | AAGTGCAGTAGTCGCCGTGAACGTTCTTTTTCGCA |
| | | ACGGGTTTGCCGCCAGAACACAGCTGGGCTAGCG |
| | | TTTAAACGGGCCCTCTAGAGCCGCCACC<u>ATGCTTC</u> |
| | | <u>TCCTGGTGACAAGCCTTCTGCTCTGTGAGTTACCA</u> |
| | | <u>CACCCAGCATTCCTCCTGATCCCAGGCCCTGTGCC</u> |
| | | <u>TCCCTCTACAGCCCTCAGGTACCTCATTGAGGAGC</u> |
| | | <u>TGGTCAACATCACCCAGAACCAGAAGGCTCCGCT</u> |
| | | <u>CTGCAATGGCAGCATGGTATGGAGCATCAACCTG</u> |
| | | <u>ACAGCTGGCATGTACTGTGCAGCCCTGGAATCCCT</u> |
| | | <u>GATCAACGTGTCAGGCTGCAGTGCCATCGAGAAG</u> |
| | | <u>ACCCAGAGGATGCTGAGCGGATTCTGCCCGCACA</u> |
| | | <u>AGGTCTCAGCTGGGCAGTTTTCCAGCTTGCATGTC</u> |
| | | <u>CGAGACACCAAAATCGAGGTGGCCCAGTTTGTAA</u> |

TABLE 2-continued

| SEQ ID NO: | Feature(s) | Sequence |
|---|---|---|

AGGACCTGCTCTTACATTTAAAGAAACTTTTTCGC
GAGGGACGGTTCAAGAATCTAAGTACCGGACCGC
CCTGCCCCCCTTGCCCTGGCCAGCCTAGAGAACCC
CAGGTGTACACCCTGCCTCCCAGCCAGGAAGAGA
TGACCAAGAACCAGGTGTCCCTGACCTGCCTGGTC
AAAGGCTTCTACCCCAGCGATATCGCCGTGGAAT
GGGAGAGCAACGGCCAGCCCGAGAACAACTACA
AGACCACCCCCCCTGTGCTGGACAGCGACGGCAG
CTTCTTCCTGTACTCCCGGCTGACCGTGGACAAGA
GCCGGTGGCAGGAAGGCAACGTCTTCAGCTGCAG
CGTGATGCACGAGGCCCTGCACAACCACTACACC
CAGAAGTCCCTGAGCCTGAGCCTGGGCAAGATGT
TCTGGGTGCTGGTGGTGGTCGGAGGCGTGCTGGC
CTGCTACAGCCTGCTGGTCACCGTGGCCTTCATCA
TCTTTTGGGTGAAACGGGGCAGAAAGAAACTCCT
GTATATATTCAAACAACCATTTATGAGACCAGTAC
AAACTACTCAAGAGGAAGATGGCTGTAGCTGCCG
ATTTCCAGAAGAAGAAGAAGGAGGATGTGAACTG
CGGGTGAAGTTCAGCAGAAGCGCCGACGCCCCTG
CCTACCAGCAGGGCCAGAATCAGCTGTACAACGA
GCTGAACCTGGGCAGAAGGGAAGAGTACGACGTC
CTGGATAAGCGGAGAGGCCGGGACCCTGAGATGG
GCGGCAAGCCTCGGCGGAAGAACCCCCAGGAAGG
CCTGTATAACGAACTGCAGAAAGACAAGATGGCC
GAGGCCTACAGCGAGATCGGCATGAAGGGCGAGC
GGAGGCGGGGCAAGGGCCACGACGGCCTGTATCA
GGGCCTGTCCACCGCCACCAAGGATACCTACGAC
GCCCTGCACATGCAGGCCCTGCCCCCAAGGCTCG
AGGGCGGCGGAGAGGGCAGAGGAAGTCTTCTAAC
ATGCGGTGACGTGGAGGAGAATCCCGGCCCTAGG
ATGCTTCTCCTGGTGACAAGCCTTCTGCTCTGTGA
GTTACCACACCCAGCATTCCTCCTGATCCCACGCA
AAGTGTGTAACGGAATAGGTATTGGTGAATTTAA
AGACTCACTCTCCATAAATGCTACGAATATTAAAC
ACTTCAAAAACTGCACCTCCATCAGTGGCGATCTC
CACATCCTGCCGGTGGCATTTAGGGGTGACTCCTT
CACACATACTCCTCCTCTGGATCCACAGGAACTGG
ATATTCTGAAAACCGTAAAGGAAATCACAGGGTT
TTTGCTGATTCAGGCTTGGCCTGAAAACAGGACG
GACCTCCATGCCTTTGAGAACCTAGAAATCATACG
CGGCAGGACCAAGCAACATGGTCAGTTTTCTCTTG
CAGTCGTCAGCCTGAACATAACATCCTTGGGATTA
CGCTCCCTCAAGGAGATAAGTGATGGAGATGTGA
TAATTTCAGGAAACAAAAATTTGTGCTATGCAAAT
ACAATAAACTGGAAAAAACTGTTTGGGACCTCCG
GTCAGAAAACCAAAATTATAAGCAACAGAGGTGA
AAACAGCTGCAAGGCCACAGGCCAGGTCTGCCAT
GCCTTGTGCTCCCCGAGGGCTGCTGGGGCCCGG
AGCCCAGGGACTGCGTCTCTTGCCGGAATGTCAG
CCGAGGCAGGGAATGCGTGGACAAGTGCAACCTT
CTGGAGGGTGAGCCAAGGGAGTTTGTGGAGAACT
CTGAGTGCATACAGTGCCACCCAGAGTGCCTGCCT
CAGGCCATGAACATCACCTGCACAGGACGGGGAC
CAGACAACTGTATCCAGTGTGCCCACTACATTGAC
GGCCCCCACTGCGTCAAGACCTGCCCGGCAGGAG
TCATGGGAGAAAACAACACCCTGGTCTGGAAGTA
CGCAGACGCCGGCCATGTGTGCCACCTGTGCCATC
CAAACTGCACCTACGGATGCACTGGGCCAGGTCT
TGAAGGCTGTCCAACGAATGGGCCTAAGATCCCG
TCCATCGCCACTGGGATGGTGGGGGCCCTCCTCTT
GCTGCTGGTGGTGGCCCTGGGGATCGGCCTCTTCA
TGTGAGCGGCCGCTCTAGACCCGGGCTGCAGGAA
TTCGATATCAAGCTTATCGATAATCAACCTCTGGA
TTACAAAATTTGTGAAAGATTGACTGGTATTCTTA
ACTATGTTGCTCCTTTTACGCTATGTGGATACGCT
GCTTTAATGCCTTTGTATCATGCTATTGCTTCCCGT
ATGGCTTTCATTTTCTCCTCCTTGTATAAATCCTGG
TTGCTGTCTCTTTATGAGGAGTTGTGGCCCGTTGT
CAGGCAACGTGGCGTGGTGTGCACTGTGTTTGCTG
ACGCAACCCCCACTGGTTGGGGCATTGCCACCAC
CTGTCAGCTCCTTTCCGGGACTTTCGCTTTCCCCCT
CCCTATTGCCACGGCGGAACTCATCGCCGCCTGCC
TTGCCCGCTGCTGGACAGGGGCTCGGCTGTTGGGC
ACTGACAATTCCGTGGTGTTGTCGGGGAAATCATC
GTCCTTTCCTTGGCTGCTCGCCTGTGTTGCCACCTG
GATTCTGCGCGGGACGTCCTTCTGCTACGTCCCTT
CGGCCCTCAATCCAGCGGACCTTCCTTCCCGCGGC
CTGCTGCCGGCTCTGCGGCCTCTTCCGCGTCTTCG

TABLE 2-continued

| SEQ ID NO: | Feature(s) | Sequence |
|---|---|---|
| | | CCTTCGCCCTCAGACGAGTCGGATCTCCCTTTGGG |
| | | CCGCCTCCCCGCATCGATACCGTCGACTAGCCGTA |
| | | CCTTTAAGACCAATGACTTACAAGGCAGCTGTAG |
| | | ATCTTAGCCACTTTTTAAAAGAAAAGGGGGGACT |
| | | GGAAGGGCTAATTCACTCCCAAAGAAGACAAGAT |
| | | CTGCTTTTTGCCTGTACTGGGTCTCTCTGGTTAGAC |
| | | CAGATCTGAGCCTGGGAGCTCTCTGGCTAACTAG |
| | | GGAACCCACTGCTTAAGCCTCAATAAAGCTTGCCT |
| | | TGAGTGCTTCAAGTAGTGTGTGCCCGTCTGTTGTG |
| | | TGACTCTGGTAACTAGAGATCCCTCAGACCCTTTT |
| | | AGTCAGTGTGGAAAATCTCTAGCAGAATTCGATA |
| | | TCAAGCTTATCGATACCGTCGACCTCGAGGGGGG |
| | | GCCCGGTACCGAGCTCGGATCCACTAGTCCAGTGT |
| | | GGTGGAATTCTGCAGATATCCAGCACAGTGGCGG |
| | | CCACTCAAGTCTGGAGGGCACGTTAAAACCCGCT |
| | | GATCAGCCTCGACTGTGCCTTCTAGTTGCCAGCCA |
| | | TCTGTTGTTTGCCCCTCCCCCGTGCCTTCCTTGACC |
| | | CTGGAAGGTGCCACTCCCACTGTCCTTTCCTAATA |
| | | AAATGAGGAAATTGCATCGCATTGTCTGAGTAGG |
| | | TGTCATTCTATTCTGGGGGGTGGGGTGGGGCAGG |
| | | ACAGCAAGGGGGAGGATTGGGAAGACAATAGCA |
| | | GGCATGCTGGGGATGCGGTGGGCTCTATGGCTTCT |
| | | ACTGGGCGGTTTTATGGACAGCAAGCGAACCGGA |
| | | ATTGCCAGCTGGGGCGCCCTCTGGTAAGGTTGGG |
| | | AAGCCCTGCAAAGTAAACTGGATGGCTTTCTCGCC |
| | | GCCAAGGATCTGATGGCGCAGGGGATCAAGCTCT |
| | | GATCAAGAGACAGGATGAGGATCGTTTCGCATGA |
| | | TTGAACAAGATGGATTGCACGCAGGTTCTCCGGC |
| | | CGCTTGGGTGGAGAGGCTATTCGGCTATGACTGG |
| | | GCACAACAGACAATCGGCTGCTCTGATGCCGCCG |
| | | TGTTCCGGCTGTCAGCGCAGGGGCGCCCGGTTCTT |
| | | TTTGTCAAGACCGACCTGTCCGGTGCCCTGAATGA |
| | | ACTGCAAGACGAGGCAGCGCGGCTATCGTGGCTG |
| | | GCCACGACGGGCGTTCCTTGCGCAGCTGTGCTCGA |
| | | CGTTGTCACTGAAGCGGGAAGGGACTGGCTGCTA |
| | | TTGGGCGAAGTGCCGGGGCAGGATCTCCTGTCAT |
| | | CTCACCTTGCTCCTGCCGAGAAAGTATCCATCATG |
| | | GCTGATGCAATGCGGCGGCTGCATACGCTTGATCC |
| | | GGCTACCTGCCCATTCGACCACCAAGCGAAACAT |
| | | CGCATCGAGCGAGCACGTACTCGGATGGAAGCCG |
| | | GTCTTGTCGATCAGGATGATCTGGACGAAGAGCA |
| | | TCAGGGGCTCGCGCCAGCCGAACTGTTCGCCAGG |
| | | CTCAAGGCGAGCATGCCCGACGGCGAGGATCTCG |
| | | TCGTGACCCATGGCGATGCCTGCTTGCCGAATATC |
| | | ATGGTGGAAAATGGCCGCTTTTCTGGATTCATCGA |
| | | CTGTGGCCGGCTGGGTGTGGCAGACCGCTATCAG |
| | | GACATAGCGTTGGCTACCCGTGATATTGCTGAAG |
| | | AGCTTGGCGGCGAATGGGCTGACCGCTTCCTCGTG |
| | | CTTTACGGTATCGCCGCTCCCGATTCGCAGCGCAT |
| | | CGCCTTCTATCGCCTTCTTGACGAGTTCTTCTGAAT |
| | | TATTAACGCTTACAATTTCCTGATGCGGTATTTTCT |
| | | CCTTACGCATCTGTGCGGTATTTCACACCGCATAC |
| | | AGGTGGCACTTTTCGGGGAAATGTGCGCGGAACC |
| | | CCTATTTGTTTATTTTTCTAAATACATTCAAATATG |
| | | TATCCGCTCATGACCAAAATCCCTTAACGTGAGTT |
| | | TTCGTTCCACTGAGCGTCAGACCCCGTAGAAAAG |
| | | ATCAAAGGATCTTCTTGAGATCCTTTTTTTCTGCG |
| | | CGTAATCTGCTGCTTGCAAACAAAAAAACCACCG |
| | | CTACCAGCGGTGGTTTGTTTGCCGGATCAAGAGCT |
| | | ACCAACTCTTTTTCCGAAGGTAACTGGCTTCAGCA |
| | | GAGCGCAGATACCAAATACTGTTCTTCTAGTGTAG |
| | | CCGTAGTTAGGCCACCACTTCAAGAACTCTGTAGC |
| | | ACCGCCTACATACCTCGCTCTGCTAATCCTGTTAC |
| | | CAGTGGCTGCTGCCAGTGGCGATAAGTCGTGTCTT |
| | | ACCGGGTTGGACTCAAGACGATAGTTACCGGATA |
| | | AGGCGCAGCGGTCGGGCTGAACGGGGGGTTCGTG |
| | | CACACAGCCCAGCTTGGAGCGAACGACCTACACC |
| | | GAACTGAGATACCTACAGCGTGAGCTATGAGAAA |
| | | GCGCCACGCTTCCCGAAGGGAGAAAGGCGGACAG |
| | | GTATCCGGTAAGCGGCAGGGTCGGAACAGGAGAG |
| | | CGCACGAGGGAGCTTCCAGGGGGAAACGCCTGGT |
| | | ATCTTTATAGTCCTGTCGGGTTTCGCCACCTCTGA |
| | | CTTGAGCGTCGATTTTTGTGATGCTCGTCAGGGGG |
| | | GCGGAGCCTATGGAAAAACGCCAGCAACGCGGCC |
| | | TTTTTACGGTTCCTGGCCTTTTTGCTGGCCTTTTGCT |
| | | CACATGTTCTTTCCTGCGTTATCCCCTGATTCTGTG |
| | | GATAACCGTATTACCGCCTTTGAGTGAGCTGATAC |
| | | CGCTCGCCGCAGCCGAACGACCGAGCGCAGCGAG |

TABLE 2-continued

| SEQ ID NO: | Feature(s) | Sequence |
|---|---|---|
| | | TCAGTGAGCGAGGAAGCGGAAGAGCGCCCAATAC |
| | | GCAAACCGCCTCTCCCCGCGCGTTGGCCGATTCAT |
| | | TAATGCAGCTGGCACGACAGGTTTCCCGACTGGA |
| | | AAGCGGGCAGTGAGCGCAACGCAATTAATGTGAG |
| | | TTAGCTCACTCATTAGGCACCCCAGGCTTTACACT |
| | | TTATGCTTCCGGCTCGTATGTTGTGTGGAATTGTG |
| | | AGCGGATAACAATTTCACACAGGAAACAGCTATG |
| | | ACCATGATTACGCCAAGCTCGAAATTAACCCTCAC |
| | | TAAAGGGAACAAAAGCTGGAGCTCCACCGCGGTG |
| | | GCGGCCTCGAGGTCGAGATCCGGTCGACCAGCAA |
| | | CCATAGTCCCGCCCCTAACTCCGCCCATCCCGCCC |
| | | CTAACTCCGCCCAGTTCCGCCCATTCTCCGCCCCA |
| | | TGGCTGACTAATTTTTTTTATTTATGCAGAGGCCG |
| | | AGGCCGCCTCGGCCTCTGAGCTATTCCAGAAGTA |
| | | GTGAGGAGGCTTTTTTGGAGGCCTAGGCTTTTGCA |
| | | AAAAGCTTCGACGGTATCGATTGGCTCATGTCCAA |
| | | CATTACCGCCATGTTGACATTGATTATTGACTAGT |
| | | TATTAATAGTAATCAATTACGGGGTCATTAGTTCA |
| | | TAGCCCATATATGGAGTTCCGCGTTACATAACTTA |
| | | CGGTAAATGGCCCGCCTGGCTGACCGCCCAACGA |
| | | CCCCCGCCCATTGACGTCAATAATGACGTATGTTC |
| | | CCATAGTAACGCCAATAGGGACTTTCCATTGACGT |
| | | CAATGGGTGGAGTATTTACGGTAAACTGCCCACTT |
| | | GGCAGTACATCAAGTGTATCATATGCCAAGTACG |
| | | CCCCCTATTGACGTCAATGACGGTAAATGGCCCGC |
| | | CTGGCATTATGCCCAGTACATGACCTTATGGGACT |
| | | TTCCTACTTGGCAGTACATCTACGTATTAGTCATC |
| | | GCTATTACCATGGTGATGCGGTTTTGGCAGTACAT |
| | | CAATGGGCGTGGATAGCGGTTTGACTCACGGGGA |
| | | TTTCCAAGTCTCCACCCCATTGACGTCAATGGGAG |
| | | TTTGTTTTGGCACCAAAATCAACGGGACTTTCCAA |
| | | AATGTCGTAACAACTCCGCCCCATTGACGCAAAT |
| | | GGGCGGTAGGCGTGTACGGAATTCGGAGTGGCGA |
| | | GCCCTCAGATCCTGCATATAAGCAGCTGCTTTTTG |
| | | CCTGTACTGGGTCTCTCTG |
| SEQ ID NO: 14 | DHFRdm | MVGSLNCIVAVSQNMGIGKNGDFPWPPLRNESRYF |
| | | QRMTTTSSVEGKQNLVIMGKKTWFSIPEKNRPLKGR |
| | | INLVLSRELKEPPQGAHFLSRSLDDALKLIEQPELAN |
| | | KVDMVWIVGGSSVYKEAMNHPGHLKLFVTRIMQD |
| | | FESDTFFPEIDLEKYKLLPEYPGVLSDVQEEKGIKYK |
| | | FEVYEKND |
| SEQ ID NO: 15 | DHFRdm | ATGGTTGGTTCGCTAAACTGCATCGTCGCTGTGTC |
| | | CCAGAACATGGGCATCGGCAAGAACGGGGACTTC |
| | | CCCTGGCCACCGCTCAGGAATGAATCCAGATATTT |
| | | CCAGAGAATGACCACAACCTCTTCAGTAGAAGGT |
| | | AAACAGAATCTGGTGATTATGGGTAAGAAGACCT |
| | | GGTTCTCCATTCCTGAGAAGAATCGACCTTTAAAG |
| | | GGTAGAATTAATTTAGTTCTCAGCAGAGAACTCA |
| | | AGGAACCTCCACAAGGAGCTCATTTTCTTTCCAGA |
| | | AGTCTAGATGATGCCTTAAAACTTACTGAACAACC |
| | | AGAATTAGCAAATAAAGTAGACATGGTCTGGATA |
| | | GTTGGTGGCAGTTCTGTTTATAAGGAAGCCATGAA |
| | | TCACCCAGGCCATCTTAAACTATTTGTGACAAGGA |
| | | TCATGCAAGACTTTGAAAGTGACACGTTTTTTCCA |
| | | GAAATTGATTTGGAGAAATATAAACTTCTGCCAG |
| | | AATACCCAGGTGTTCTCTCTGATGTCCAGGAGGAG |
| | | AAAGGCATTAAGTACAAATTTGAAGTATATGAGA |
| | | AGAATGATTAA |
| SEQ ID NO: 16 | IL-13 zetakine | ATGCTTCTCCTGGTGACAAGCCTTCTGCTCTGTGA |
| | | GTTACCACACCCAGCATTCCTCCTGATCCCAGGCC |
| | | CTGTGCCTCCCTCTACAGCCCTCAGGTACCTCATT |
| | | GAGGAGCTGGTCAACATCACCCAGAACCAGAAGG |
| | | CTCCGCTCTGCAATGGCAGCATGGTATGGAGCATC |
| | | AACCTGACAGCTGGCATGTACTGTGCAGCCCTGG |
| | | AATCCCTGATCAACGTGTCAGGCTGCAGTGCCATC |
| | | GAGAAGACCCAGAGGATGCTGAGCGGATTCTGCC |
| | | CGCACAAGGTCTCAGCTGGGCAGTTTTCCAGCTTG |
| | | CATGTCCGAGACACCAAAATCGAGGTGGCCCAGT |
| | | TTGTAAAGGACCTGCTCTTACATTTAAAGAAACTT |
| | | TTTCGCGAGGGACGGTTCAAG |
| SEQ ID NO: 17 | IL-13 zetakine | MLLLVTSLLLCELPHPAFLLIPGPVPPSTALRYLIEEL |
| | | VNITQNQKAPLCNGSMVWSINLTAGMYCAALESLIN |
| | | VSGCSAIEKTQRMLSGFCPEIKVSAGQFSSLHVRDTKI |
| | | EVAQFVKDLLLHLKKLFREGRFK |

TABLE 2-continued

| SEQ ID NO: | Feature(s) | Sequence |
|---|---|---|
| SEQ ID NO: 18 | CD28tm | MFWVLVVVGGVLACYSLLVTVAFIIFWV |
| SEQ ID NO: 19 | GMCSFss Leader | ATGCTTCTCCTGGTGACAAGCCTTCTGCTCTGTGA GTTACCACACCCAGCATTCCTCCTGATCCCA |
| SEQ ID NO: 20 | CD28tm | ATGTTCTGGGTGCTGGTGGTGGTCGGAGGCGTGCT GGCCTGCTACAGCCTGCTGGTCACCGTGGCCTTCA TCATCTTTTGGGTG |
| SEQ ID NO: 21 | 41-BB | AAACGGGGCAGAAAGAAACTCCTGTATATATTCA AACAACCATTTATGAGACCAGTACAAACTACTCA AGAGGAAGATGGCTGTAGCTGCCGATTTCCAGAA GAAGAAGAAGGAGGATGTGAACTG |
| SEQ ID NO: 22 | CD3ζ | CGGGTGAAGTTCAGCAGAAGCGCCGACGCCCCTG CCTACCAGCAGGGCCAGAATCAGCTGTACAACGA GCTGAACCTGGGCAGAAGGGAAGAGTACGACGTC CTGGATAAGCGGAGAGGCCGGGACCCTGAGATGG GCGGCAAGCCTCGGCGGAAGAACCCCCAGGAAGG CCTGTATAACGAACTGCAGAAAGACAAGATGGCC GAGGCCTACAGCGAGATCGGCATGAAGGGCGAGC GGAGGCGGGGCAAGGGCCACGACGGCCTGTATCA GGGCCTGTCCACCGCCACCAAGGATACCTACGAC GCCCTGCACATGCAGGCCCTGCCCCCCAAGG |
| SEQ ID NO: 23 | T2A | CTCGAGGGCGGCGGAGAGGGCAGAGGAAGTCTTC TAACATGCGGTGACGTGGAGGAGAATCCCGGCCCC TAGG |
| SEQ ID NO: 24 | EGFRt | CGCAAAGTGTGTAACGGAATAGGTATTGGTGAAT TTAAAGACTCACTCTCCATAAATGCTACGAATATT AAACACTTCAAAAACTGCACCTCCATCAGTGGCG ATCTCCACATCCTGCCGGTGGCATTTAGGGGTGAC TCCTTCACACATACTCCTCCTCTGGATCCACAGGA ACTGGATATTCTGAAAACCGTAAAGGAAATCACA GGGTTTTTTGCTGATTCAGGCTTGGCCTGAAAACAG GACGGACCTCCATGCCTTTGAGAACCTAGAAATC ATACGCGGCAGGACCAAGCAACATGGTCAGTTTT CTCTTGCAGTCGTCAGCCTGAACATAACATCCTTG GGATTACGCTCCCTCAAGGAGATAAGTGATGGAG ATGTGATAATTTCAGGAAACAAAAATTTGTGCTAT GCAAATACAATAAACTGGAAAAAACTGTTTGGGA CCTCCGGTCAGAAAACCAAAATTATAAGCAACAG AGGTGAAAACAGCTGCAAGGCCACAGGCCAGGTC TGCCATGCCTTGTGCTCCCCCGAGGGCTGCTGGGG CCCGGAGCCCAGGGACTGCGTCTCTTGCCGGAAT GTCAGCCGAGGCAGGGAATGCGTGGACAAGTGCA ACCTTCTGGAGGGTGAGCCAAGGGAGTTTGTGGA GAACTCTGAGTGCATACAGTGCCACCCAGAGTGC CTGCCTCAGGCCATGAACATCACCTGCACAGGAC GGGGACCAGACAACTGTATCCAGTGTGCCCACTA CATTGACGGCCCCCACTGCGTCAAGACCTGCCCG GCAGGAGTCATGGGAGAAAACAACACCCTGGTCT GGAAGTACGCAGACGCCGGCCATGTGTGCCACCT GTGCCATCCAAACTGCACCTACGGATGCACTGGG CCAGGTCTTGAAGGCTGTCCAACGAATGGGCCTA AGATCCCGTCCATCGCCACTGGGATGGTGGGGGC CCTCCTCTTGCTGCTGGTGGTGGCCCTGGGGATCG GCCTCTTCATG |
| SEQ ID NO: 25 | S spacer | GAATCTAAGTACGGACCGCCCTGCCCCCCTTGCCC T |
| SEQ ID NO: 26 | M spacer | GAATCTAAGTACGGACCGCCCTGCCCCCCTTGCCC TGGCCAGCCTAGAGAACCCCAGGTGTACACCCTG CCTCCCAGCCAGGAAGAGATGACCAAGAACCAGG TGTCCCTGACCTGCCTGGTCAAAGGCTTCTACCCC AGCGATATCGCCGTGGAATGGGAGAGCAACGGCC AGCCCGAGAACAACTACAAGACCACCCCCCCTGT GCTGGACAGCGACGGCAGCTTCTTCCTGTACTCCC GGCTGACCGTGGACAAGAGCCGGTGGCAGGAAGG CAACGTCTTCAGCTGCAGCGTGATGCACGAGGCC CTGCACAACCACTACACCCAGAAGTCCCTGAGCC TGAGCCTGGGCAAG |
| SEQ ID NO: 27 | L spacer | ATCTAAGTACGGACCGCCCTGCCCCCCTTGCCCTG CCCCCGAGTTCGACGGCGGACCCAGCGTGTTCCTG |

TABLE 2-continued

| SEQ ID NO: | Feature(s) | Sequence |
|---|---|---|
| | | TTCCCCCCCAAGCCCAAGGACACCCTGATGATCA |
| | | GCCGGACCCCCGAGGTGACCTGCGTGGTGGTGGA |
| | | CGTGAGCCAGGAAGATCCCGAGGTCCAGTTCAAT |
| | | TGGTACGTGGACGGCGTGGAAGTGCACAACGCCA |
| | | AGACCAAGCCCAGAGAGGAACAGTTCCAGAGCAC |
| | | CTACCGGGTGGTGTCTGTGCTGACCGTGCTGCACC |
| | | AGGACTGGCTGAACGGCAAAGAATACAAGTGCAA |
| | | GGTGTCCAACAAGGGCCTGCCCAGCAGCATCGAA |
| | | AAGACCATCAGCAAGGCCAAGGGCCAGCCTCGCG |
| | | AGCCCCAGGTGTACACCCTGCCTCCCTCCCAGGAA |
| | | GAGATGACCAAGAACCAGGTGTCCCTGACCTGCC |
| | | TGGTGAAGGGCTTCTACCCCAGCGACATCGCCGT |
| | | GGAGTGGGAGAGCAACGGCCAGCCTGAGAACAA |
| | | CTACAAGACCACCCCTCCCGTGCTGGACAGCGAC |
| | | GGCAGCTTCTTCCTGTACAGCCGGCTGACCGTGGA |
| | | CAAGAGCCGGTGGCAGGAAGGCAACGTCTTTAGC |
| | | TGCAGCGTGATGCACGAGGCCCTGCACAACCACT |
| | | ACACCCAGAAGAGCCTGAGCCTGTCCCTGGGCAA |
| | | G |

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A nucleic acid encoding an IL-13 mutein-directed zetakine receptor, the zetakine receptor comprising:
- an extracellular domain comprising a mutein of IL-13;
- a spacer
  - consisting of an IgG4 hinge-CH3 having 119 amino acids in length and having at least 90% sequence identity with the amino acid sequence set forth in SEQ ID NO: 10 or
    - comprising an IgG4 hinge-CH2-CH3 comprising L235D and N297Q mutations;
- a transmembrane domain; and
- an intracellular signaling region,
- wherein the spacer links the mutein to the transmembrane domain, and
- wherein the transmembrane domain is linked to the intracellular signaling region.

2. The nucleic acid of claim 1, wherein the mutein has an amino acid sequence having at least 90% identity with the amino acid sequence set forth in SEQ ID NO: 17.

3. The nucleic acid of claim 1, wherein the mutein has an amino acid sequence set forth in SEQ ID NO:17.

4. The nucleic acid of claim 1, wherein the spacer has the amino acid sequence set forth in SEQ ID NO: 10.

5. The nucleic acid of claim 1, wherein the spacer has the amino acid sequence encoded by SEQ ID NO:27.

6. The nucleic acid of claim 1, wherein the spacer has the amino acid sequence set forth in SEQ ID NO: 11 with a leucine to aspartate mutation at amino acid 17 and an asparagine to glutamine mutation at amino acid 79.

7. The nucleic acid of claim 1, wherein the transmembrane domain comprises a CD28 transmembrane domain.

8. The nucleic acid of claim 1, wherein the intracellular signaling region comprises all or a portion of a CD3 zeta domain in combination with a co-stimulatory domain selected from the group consisting of CD27, CD28, 4-1BB, OX-40, CD30, CD40, PD-1, ICOS, LFA-1, CD2, CD7, NKG2C, B7-H3, and a combination thereof.

9. The nucleic acid of claim 1, wherein the intracellular signaling region comprises a portion of a CD3 zeta domain and a co-stimulatory portion of a 4-1BB domain.

10. The nucleic acid of claim 1, further comprising a sequence encoding a marker.

11. The nucleic acid of claim 10, wherein the marker comprises a truncated epidermal growth factor receptor or a dihydrofolate reductase (DHFR).

12. The nucleic acid of claim 11, wherein the DHFR is a DHFR double mutant (DHFRdm).

13. The nucleic acid of claim 12, wherein the DHFRdm comprises amino acid mutations L22F and F31S.

14. The nucleic acid of claim 1, further comprising a ribosomal skip sequence.

15. The nucleic acid of claim 14, wherein the ribosomal skip sequence comprises P2A or T2A.

* * * * *